United States Patent [19]

Horvath et al.

[11] 4,381,447
[45] Apr. 26, 1983

[54] METHOD AND APPARATUS FOR EVALUATING AND SORTING SHEETS IN A HIGH SPEED MANNER

[75] Inventors: Stephen J. Horvath, Bensalem, Pa.; Steven R. Wilcox, Mount Laurel, N.J.

[73] Assignee: Brandt, Inc., Bensalem, Pa.

[21] Appl. No.: 188,891

[22] Filed: Sep. 19, 1980

[51] Int. Cl.³ .............................................. G01V 9/04
[52] U.S. Cl. ................................. 250/223 R; 364/552
[58] Field of Search .................. 250/223 R, 562, 563, 250/571, 572, 561; 356/71; 209/524, 528, 532; 364/551, 552, 507

[56] References Cited

U.S. PATENT DOCUMENTS

| | | | |
|---|---|---|---|
| 2,526,916 | 10/1950 | Turrall | 271/64 |
| 2,563,498 | 8/1951 | Skinner | 271/64 |
| 3,166,313 | 1/1965 | Rehm | 271/86 |
| 3,205,741 | 9/1965 | Haselow | 83/106 |
| 3,265,208 | 8/1966 | Reniker et al. | 209/111.8 |
| 3,327,850 | 6/1967 | Simmons | 209/111.7 |
| 3,472,506 | 10/1969 | Rabinow et al. | 271/64 |
| 3,987,902 | 10/1976 | Burgess et al. | 250/223 R |
| 4,025,420 | 5/1977 | Horino | 250/562 |
| 4,237,539 | 12/1980 | Piovoso et al. | 364/552 |

*Primary Examiner*—David C. Nelms
*Attorney, Agent, or Firm*—Weinstein & Sutton

[57] ABSTRACT

Electronic solid state circuitry incorporating the microprocessor for automatically controlling document handling apparatus. Sheets are advanced from a stack of sheets arranged in an infeed stacker and are moved one at a time at high speed through an examining location where sensors examine the sheets to determine their condition. The microprocessor periodically initiates an adjustment in the brightness level and gain control level of the lamps and sensor elements employed in the sensor array; tracks each sheet as it moves through the document handling apparatus; and evaluates the outputs developed by the sensors to determine the fitness of each sheet. A gating roller assembly, under control of the microprocessor, is operated to divert each sheet toward one of a plurality of output stackers according to the results of the evaluation performed by the microprocessor. Timing of the electronic circuitry is controlled by timing signals derived from the document handling apparatus to synchronise the electronic circuitry with the document handling apparatus. The sheets are tested during their high speed movement for a variety of conditions which are operator selectable and which conditions are operator adjustable.

12 Claims, 36 Drawing Figures

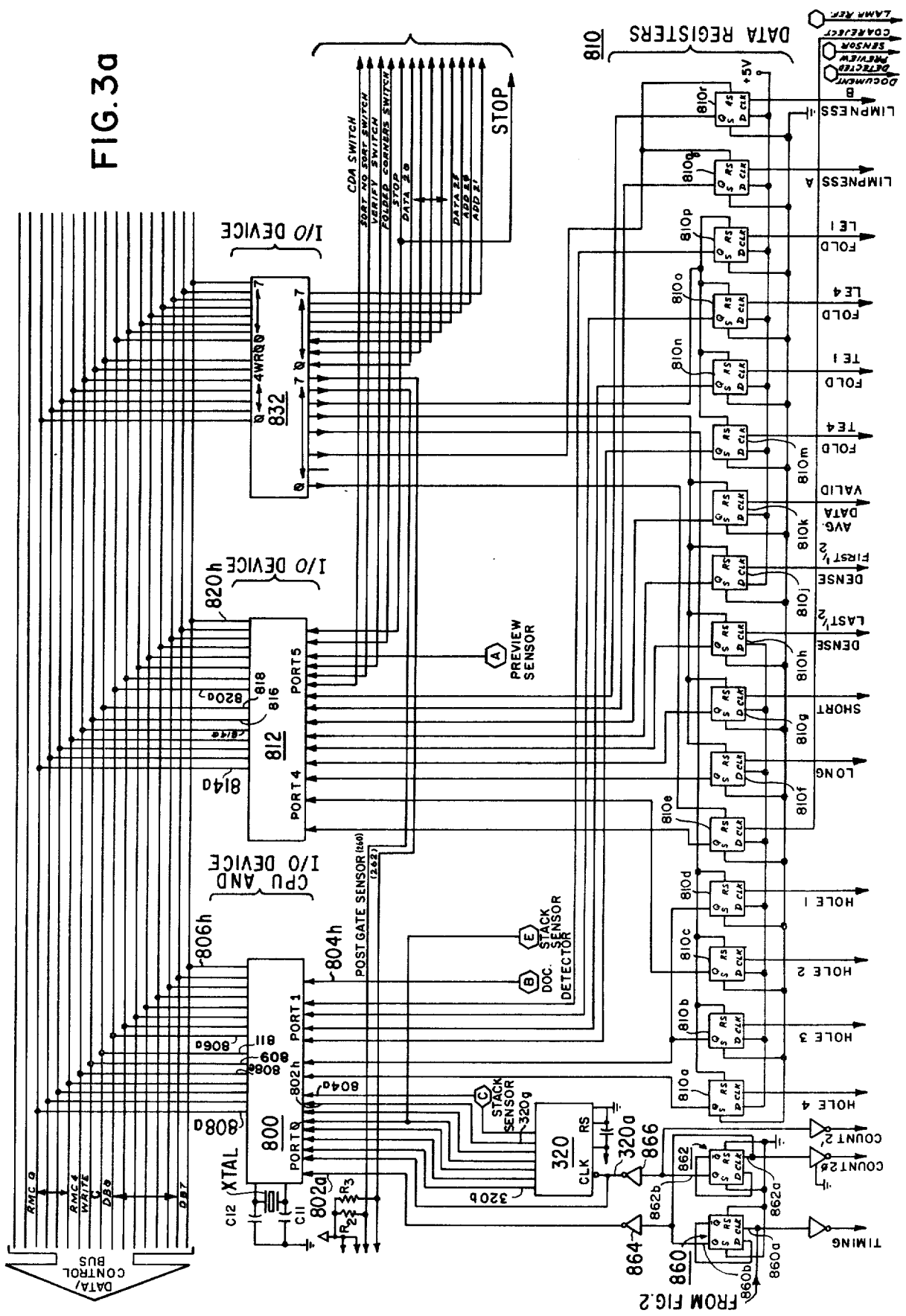

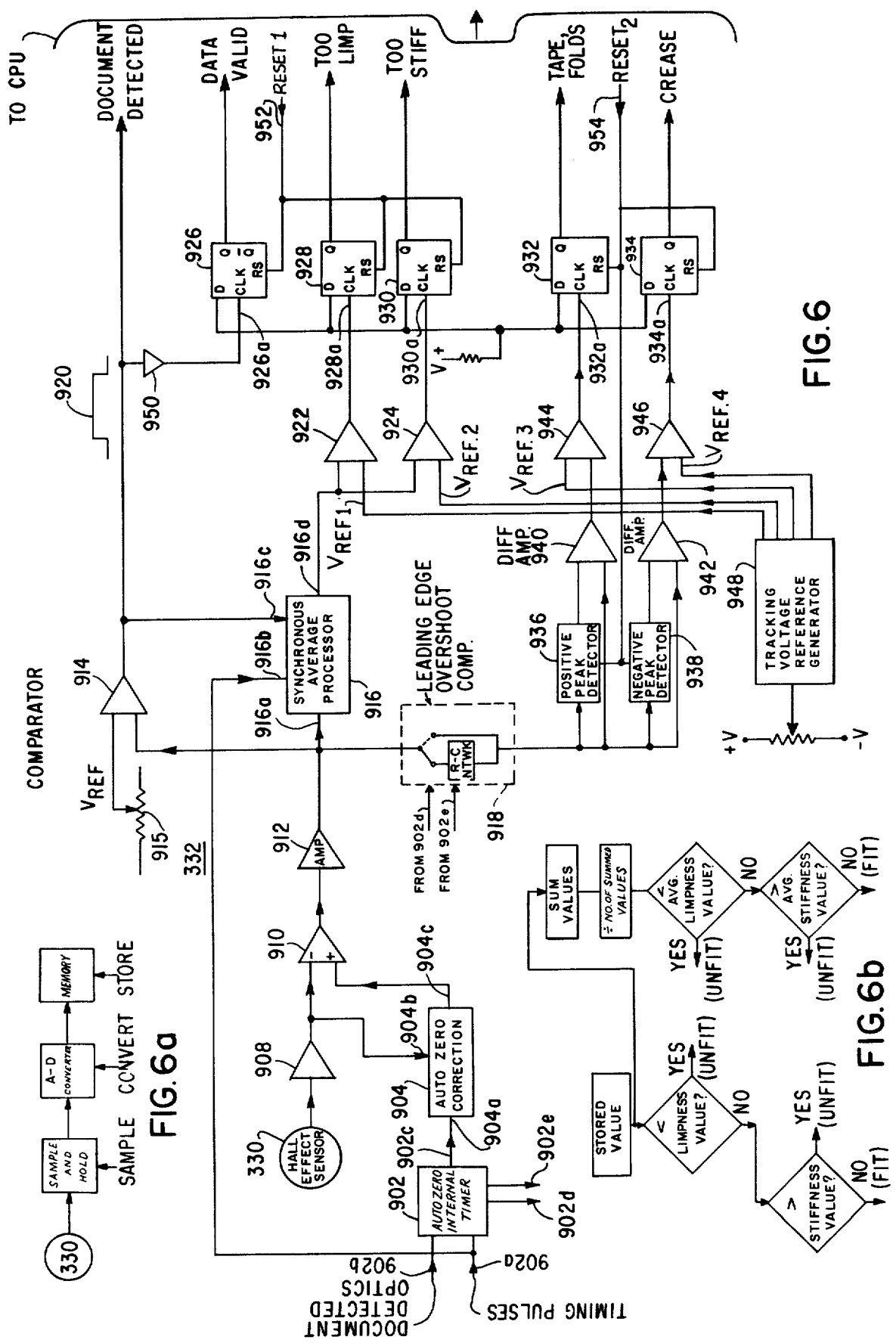

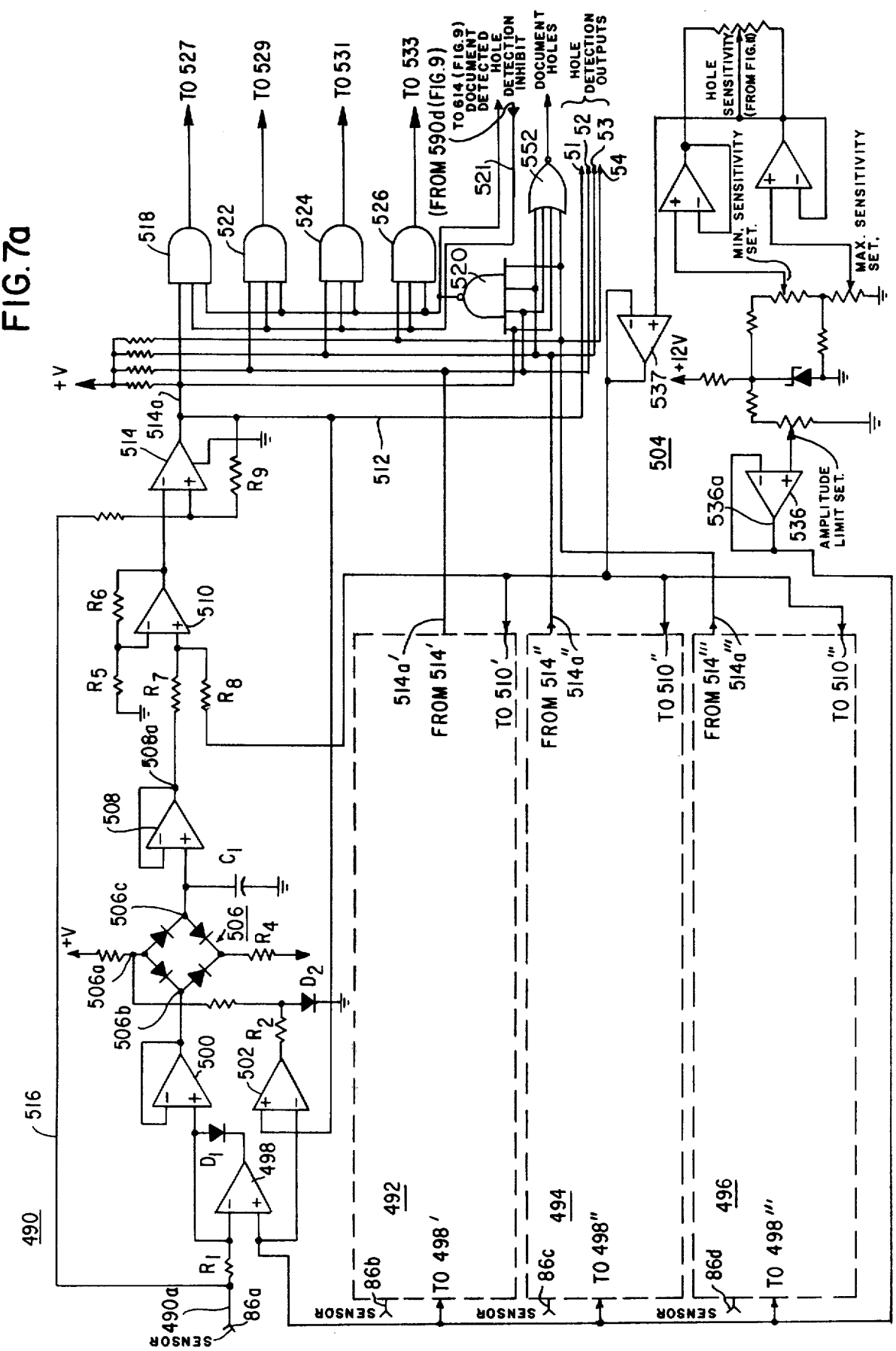

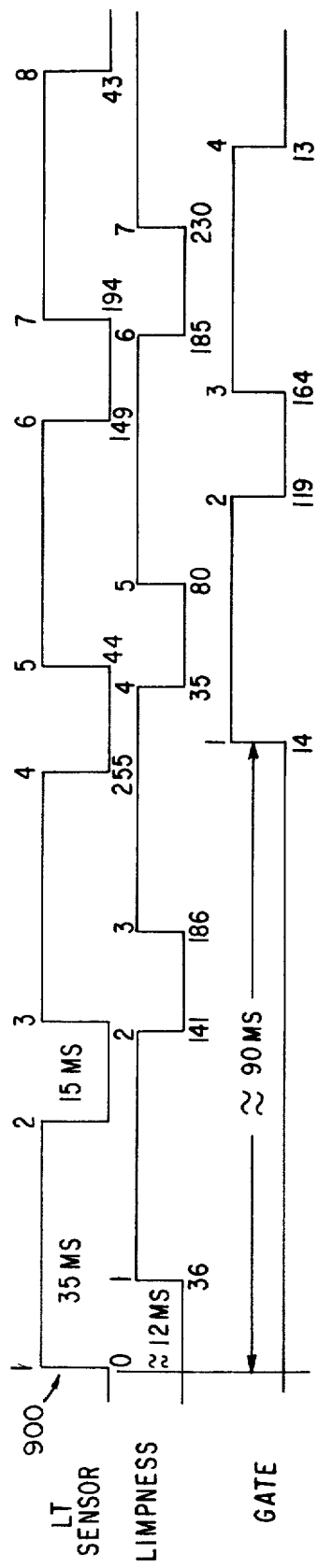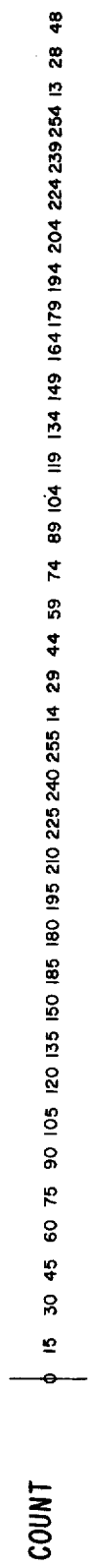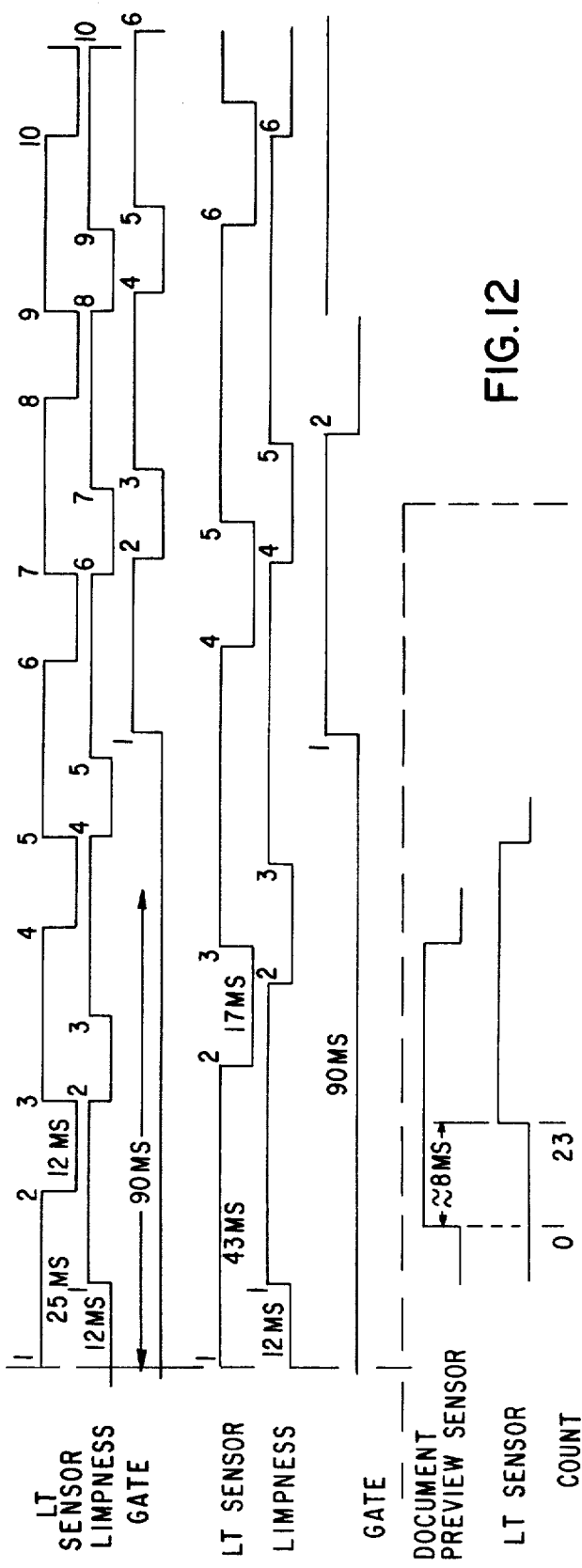
FIG.12

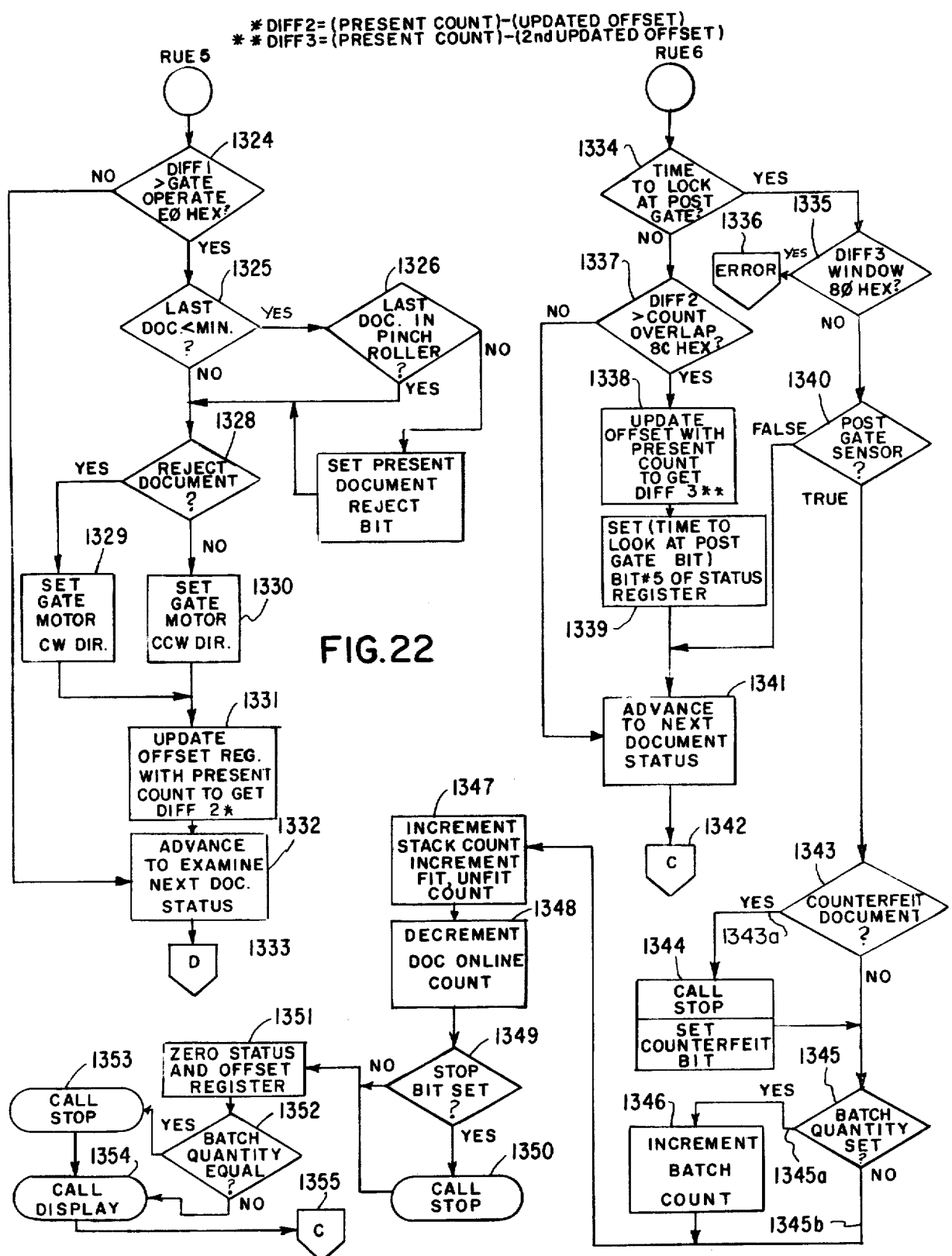

METHOD AND APPARATUS FOR EVALUATING AND SORTING SHEETS IN A HIGH SPEED MANNER

FIELD OF THE INVENTION

The present invention relates to document handling apparatus and more particularly to electronic circuitry for high speed automatic control of document handling apparatus to examine sheets as they move one at a time at high speed through said apparatus and to control delivery of the sheets to one of a plurality of output stackers according to the results of the evaluation and at no reduction in handling speed.

BACKGROUND OF THE INVENTION

A document handling apparatus is utilized for handling sheets such as, but not limited to, checks, paper currency, food and premium coupons and other like documents. There are a number of applications in which it is desired to be able to handle such sheets at high speed, to evaluate said sheets to ascertain whether they meet or fail to meet certain criteria and to divert the evaluated sheets to an output path associated with the results of the evaluation. For example, in the handling of paper currency, it is extremely desirable to be able to sort paper currency in accordance with certain criteria. Many banks and other like institutions utilize automated facilities sometimes referred to as 24-hour banking equipment, in which it is possible to withdraw money at any hour of the day or night simply by inserting a plastic card into an appropriate slot and manipulating certain buttons upon a control panel for the purpose of withdrawing money, such as paper currency, for example. Such automated banking equipment has been found to operate successfully only with the use of new or nearly new paper currency, since paper currency which is worn or has any tears or folded corners will not be properly fed by the automatic teller equipment and will, in fact, cause it to jam. Since new or nearly new paper currency is often difficult to obtain on a regular basis from the Federal Reserve, one of the best techniques of obtaining new or nearly new paper currency which will meet all of the criteria necessary for use in automatic banking equipment, is to examine paper currency taken in by the bank and sort out all new or nearly new paper currency for use in the automatic teller equipment. This technique is presently being done manually which constitutes an extremely tedious and time-consuming procedure.

Other operations which banks and other similar institutions are interested in performing at high speed are evaluation of paper currency for purposes of sorting unfit paper currency from fit paper currency, in order to withdraw unfit paper currency from circulation and return same to the Federal Reserve for subsequent destruction. Paper currency which, although it may not quite meet the stringent criteria which must be met for use in automated teller equipment, may nevertheless be in satisfactory condition for use by the bank or other similar institutions in normal day-to-day transactions. It thus becomes desirable to sort otherwise fit paper currency from unfit paper currency in order to provide tellers with paper currency acceptable for continuing circulation and to remove unfit paper currency from circulation and for return to the Federal Reserve. Operations of this nature are also being performed manually. It is thus extremely desirable to be able to perform such operations in an automatic, high-speed manner and to be able to evaluate sheets such as paper currency to determine whether they are too stiff or too limp; too light or too dark; ripped, torn, perforated or otherwise damaged; have torn and/or folded corners and even evaluate such sheets to determine or aid in a determination of their authenticity.

BRIEF DESCRIPTION OF THE INVENTION

The present invention is characterized by comprising document handling apparatus and method and apparatus for controlling document handling apparatus at a high speed in order to perform all of the above-mentioned examinations, to evaluate the results of the examinations, and to sort sheets in accordance with said results in a substantially uninterrupted manner, wherein the examination and control means enables such operations to be performed at no reduction in system operating speed.

The document handling apparatus of the present invention comprises an infeed stacker for receiving a large stack of sheets to be evaluated. The mechanism delivers sheets from the stack on a one-at-a-time basis and at high speed through an examination station where the sheets are examined to develop signals representative of their condition. These signals are evaluated by the electronic circuitry, which incorporates a microprocessor, to determine whether the sheets meet certain criteria which, to increase the versatility of the equipment, are operator selectable.

The microprocessor utlizes signals from the sensor array to track each sheet as it moves through the document handling apparatus in order to control gating apparatus to gate sheets to appropriate output stacker locations depending upon whether the sheets have met or failed to meet the criteria for fit documents.

The document handling apparatus is capable of having several sheets at varioius locations within the path of movement of the document handling and counting apparatus. The microprocessor is capable of tracking each such sheet, receiving data for each sheet and storing said data in addresses allocated to the associated sheet, all of said operations being performed accurately and at high operating speeds. The microprocessor evaluates the sensor signals for each sheet and controls gating means to divert sheets to the appropriate output stacker location in accordance with the results of the evaluation.

A variety of sensing means are provided to produce signals which assure that the gating means have operated properly. These signals are evaluated by the microprocessor to assure proper operation or, in the alternative, to take appropriate action to halt the document handling apparatus, or portions thereof, to prevent the equipment from being damaged in the event of any improper or erroneous operation.

The sensing apparatus utilizes solid state electronic circuits which assure the provision of highly sensitive and precision sensing signals to facilitate highly accurate evaluation of the sheets to be assured that they meet the desired operator adjustable criteria.

Novel digital type sample and hold circuitry is employed for retaining signal conditions over long time intervals and especially in the event that the document handling apparatus is halted, for example, for batching purposes.

The aforesaid type circuitry is further employed in conjunction with the sensing arrays in order to continuously monitor signal levels of the sensor devices and lamp sources used in cooperation therewith to provide constantly updated compensation for any abrupt and/or gradual changes in components of the sensor array due to aging, accumulation of dust or dirt or for any other reason.

The sensing circuitry is utilized for counting and length measuring purposes as well as the criteria mentioned hereinabove to add still further versatility to the system.

The document handling apparatus utilizes a plurality of motors whose operation is controlled by the microprocessor. Timing means associated with the output of one of said motors generates timing pulses utilized to synchronize the electronics of the system with the mechanical document handling apparatus. The signals are used in each of the detection circuits.

The microprocessor controls a lamp source which is utilized as the light source for the sensor array. A lamp regulator circuit is employed to exert control over the operating voltage level of the supply source to assure that the lamp source is operated within tight voltage tolerances to control its output brightness level to achieve a long, useful operating life.

The sensors cooperating with the light source are coupled to amplifying means having automatic gain control circuitry for automatically and constantly updating the output levels of the amplifying means to be assured that any changes in output level which may be due to accumulation of dust or dirt, component aging, or other causes, is automatically fully compensated for in order to prevent erroneous operation of the detection circuits.

Limpness detection is performed by a limpness detector assembly which converts physical displacement of a movable detector member within the limpness detector assembly into an electrical signal. The signal is compared against adjustable reference levels for detecting the presence of sheets which may be either too limp or too stiff. A comparator output signal is presented to the microprocessor to indicate the condition of the bill, i.e., either too limp, too stiff or neither of the above.

The sensing signals, after undergoing the aforementioned automatic gain control, are simultaneously applied to the hole detection circuitry, folded corner detection circuitry and average density and length detection circuitry.

The hole detection circuitry, which is operator adjustable, is designed to indicate the presence of holes and/or tears within the sheet and further to indicate the portion or portions of the sheet in which the hole or tear is present. The sensor array utilizes a plurality of sensors arranged in side-by-side fashion, each designed to sense an associated "strip" of the sheet. The absence of light from all of said sensors is interpreted as the presence of a document, which information is utilized for document counting purposes. The presence of a hole or tear by any one or less than all of the sensors causes the detecting sensor or sensors to abruptly generate a pulse of large magnitude. The entire waveform undergoes slew rate limiting and an offset adjustment. The resultant signal is compared against the original unaltered signal, whereupon any portion of the unaltered signal exceeding the altered signal, which functions as a dynamic threshold level, causes a pulse or pulses to be generated at such time, which pulse is interpreted as the presence of a hole or tear. The duration of the pulse represents the size of the hole or tear measured in the direction of movement of the sheet and is utilized to control the accumulation of pulses by a digital sample and hold circuit whose output is compared against an adjustable threshold in order to detect the presence of a hole or tear greater than a predetermined size, the adjustable threshold enabling the size of the hole or tear to be ignored being operator selectable. The results of the evaluation for each sensor is stored within a bistable flip-flop for subsequent examination by the microprocessor.

The folded corner detection circuitry derives signals from the sensors in the sensor array which scan the sheets. The signals developed by the sensors are examined to determine the delayed occurrence of the corners of the leading edge of a sheet relative to the central portion of the leading edge of the sheet and the early occurrence of a corner of the trailing edge of the sheet relative to the central portion of the trailing edge of the sheet to detect the presence of a missing leading and/or trailing edge corner due to the fact that the corner is either torn or folded. These signals are stored for use by the microprocessor for subsequent evaluation.

A combined average density and length detection circuit utilizes the document detected signal developed by the hole detection circuit to initate the accumulation of timing pulses in a digital sample and hold circuit. The occurrence of the trailing edge of a sheet terminates the count, which is present in analog form to comparator means which provide signals representing either the presence or absence of a sheet which is too short or too long.

An average density signal is developed by accumulating timing pulses when the sheet is either too light or too dark, which thresholds are selected by operator adjustable controls. The count is compared against a density reference level to develop a signal when the document is darker (or lighter) than a machine adjustable threshold. Density readings are taken during each half of the sheet which serves to increase the sensitivity of the detection circuitry and which further serves as a means for aiding in the detection of the possible feeding of overlapping sheets. These signals are temporarily stored in bistable circuits pending their examination by the microprocessor.

Paper currency is examined for genuineness and the results of these tests are also made available to the microprocessor, which abruptly halts the apparatus so that the suspect sheet is the last sheet to be delivered to the unfit output location when the apparatus is turned off.

The microprocessor exerts control over all of the electronic circuits, energizing the lamp source employed as part of the sensor array assembly upon the occurrence of initial set-up conditions; initiates automatic gain control adjustments for the sensor adjustable amplifiers only upon the occurrence of intervals during which sheets are absent; collects the signals representative of the conditions observed by the sensor array for further processing; and controls the various motors and brake means based upon the observed conditions.

The timing signals for the electronic circuitry are derived from the document handling apparatus and applied to a timing counter which is repetitively stepped to a full count, automatically reset and subsequently stepped to a full count so long as the document handling apparatus is in operation.

As soon as a sheet passes a predetermined point within the document handling apparatus, this condition is detected by sensor means causing the microprocessor to store the count, hereinafter referred to as a status count, in the aforesaid timing counter at that instant, which status count is stored in a memory location assigned to that sheet, said count being unique to the last mentioned sheet. A second artificially generated offset count is simultaneously stored in a second memory location associated with the last mentioned sheet. The offset count is periodically updated by comparing the status count against the count in the counter which is continuously incremented by the timing pulses. Each updated offset count represents the advancement of the sheet to a particular location in the document handling apparatus. The microprocessor periodically examines the offset count and executes a sub-routine comprised of a plurality of steps to be performed at the time that the sheet reaches the locations in the document handling apparatus associated with the present offset count. As the next sheet comes "on line", the status and off-set counts previously stored in the memory locations assigned to the first sheet to come "on line" are transferred to a second pair of memory locations utilized to store the status and offset counts representative of a sheet which is moved a predetermined distance downstream from the "on line" location. The status and offset count for the sheet just coming "on line" are then stored in the first-mentioned pair of memory locations. This operation is repeated for several sheets wherein the document handling apparatus is capable of keeping track of as few as one and up to five sheets each moving at spaced intervals through the document handling apparatus between the infeed hopper and the outfeed stackers.

When certain counts are developed within the offset counters of each of the sheets in process within the document handling apparatus, said counts trigger the microprocessor to sample certain of the conditions being observed. The states of the signals are examined by the microprocessor which controls the gating roller to divert sheets toward the appropriate output stackers in accordance with the observed conditions. In one preferred embodiment, output stackers for fit and unfit documents are provided and sheets are selectively diverted thereto in accordance with the observed conditions. Detector means are provided along each of the alternate output paths and their conditions are sampled and observed by the microprocessor to be assured that sheets have, in fact, been diverted to the proper output stacker. In the absence of the condition which is anticipated to be present based upon the control signal applied to the gating roller, the microprocessor halts all but the stacker motor to prevent the document handling apparatus from being damaged.

The microprocessor also interfaces with visual display means and a control panel for exerting control over the adjustable thresholds of the detection circuits and the display means in accordance with operator selections undertaken through manipulation of the panel controls.

The detection circuits are adapted to retain any count developed therein during the examination of a sheet or sheets in the event that the document handling apparatus is temporarily halted, for example, during a batching operation. When the machine is restarted, the counts pick up precisely where they left off, assuring that the observed conditions are accurate and in accordance with the sensitivity adjustments selected by the operator.

The microprocessor also cooperates with sensor means to prevent the lamp from being illuminated when no sheets are present in the infeed stacker and also to turn off the lamp and the motors of the document handling apparatus when all the sheets in the infeed hopper have been processed through the document handling apparatus.

In the event that the operator controls are manipulated to perform a counterfeit detection operation, the microprocessor, in the presence of a signal representing a "suspect" document, causes the "suspect" sheet to be the last sheet to be transferred to the "unfit" output stacker, whereupon the document handling apparatus is abruptly halted. A display indication alerts the operator to the "suspect" condition enabling the suspect document to be removed for subsequent observation.

The system may be employed for document counting or may be employed for document counting and sorting whereupon one, more than one, or all of the aforementioned conditions may be sensed depending upon the desires of the operator.

OBJECTS OF THE INVENTION AND BRIEF DESCRIPTION OF THE FIGURES

It is, therefore, one object of the present invention to provide a novel, high-speed document handling apparatus and cooperating electronic solid state control means therefor to provide for high speed handling, examination and sorting of sheets in accordance with one or more operator selectable criteria.

Another object of the present invention is to provide novel detection circuits for use in conjunction with document handling apparatus for detecting certain conditions of the examined sheet and for comparing said conditions against adjustably selectable thresholds to ascertain the relative fitness or unfitness of the sheet in accordance with preselected criteria.

Still another object of the present invention is to provide novel, solid state electronic detection circuits for use with document handling and examining apparatus and incorporating novel, adjustable amplifier means provided to compensate for changes in signal levels of the sensors due to the accumulation of dust or dirt, aging of circuit components and the like, said adjustment being made during operation but at a time when gaps between sheets are passing the sensors.

Still another object of the present invention is to provide novel, electronic solid state detection circuits responsive to signals of a sensor array to determine the fitness of a sheet with respect to certain preselected criteria, and which incorporate digital sample and hold circuits capable of indefinitely storing the count of an accumulated condition during an interruption in the operation of the document handling apparatus, for example, due to batching.

Still another object of the present invention is to provide a novel document handling apparatus incorporating solid state electronic control means utilizing a microprocessor for monitoring and controlling all of the operations of the document handling apparatus, evaluating the signals developed by the detection circuits and diverting examined sheets to an appropriate one of plural outfeed stackers in accordance with the examined conditions.

Still another object of the present invention is to provide document handling apparatus incorporating a microprocessor and related electronic circuits wherein sheets passing through the document handling apparatus are automatically tracked by the microprocessor to assure performance of all operations of the document handling apparatus in accordance with the location and condition of each of the examined sheets.

The above as well as other objects of the present invention will become apparent when reading the accompanying description and drawings in which:

FIG. 1a shows a simplified plan view of the cooperating light source and sensor array of FIG. 1.

FIGS. 3a and 3b show a detailed block diagram of the central processor unit employed in the control system of FIG. 2 and embodying a microprocessor.

FIG. 6 is a schematic diagram showing the limpness detection circuit of FIG. 2 in greater detail.

FIGS. 6a and 6b are diagrams showing an alternative arrangement for detecting for limpness.

Figure 2:
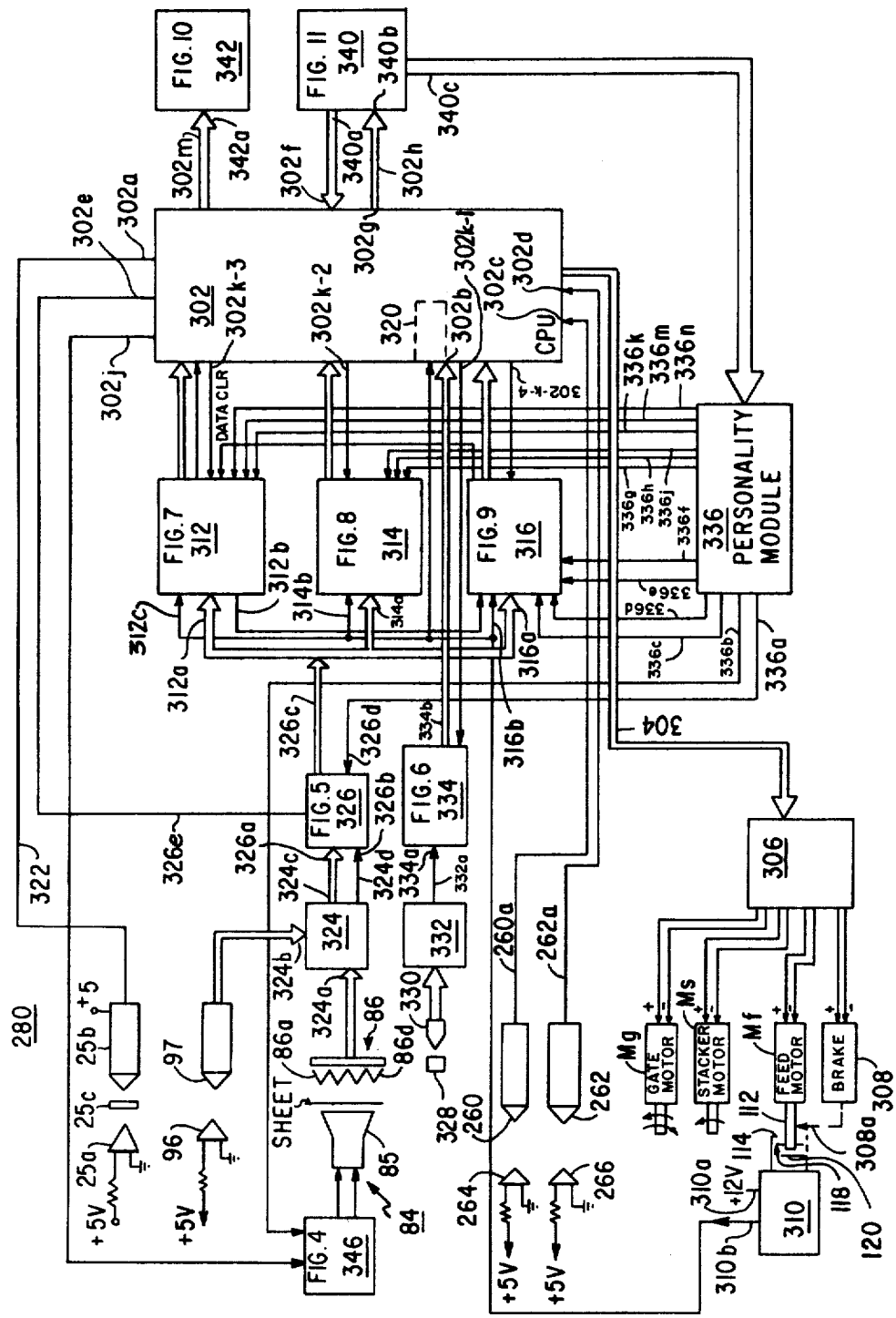
FIG. 2 shows a block diagram of the electronic control means for controlling the document handling apparatus of FIG. 1.
Figure 7B:
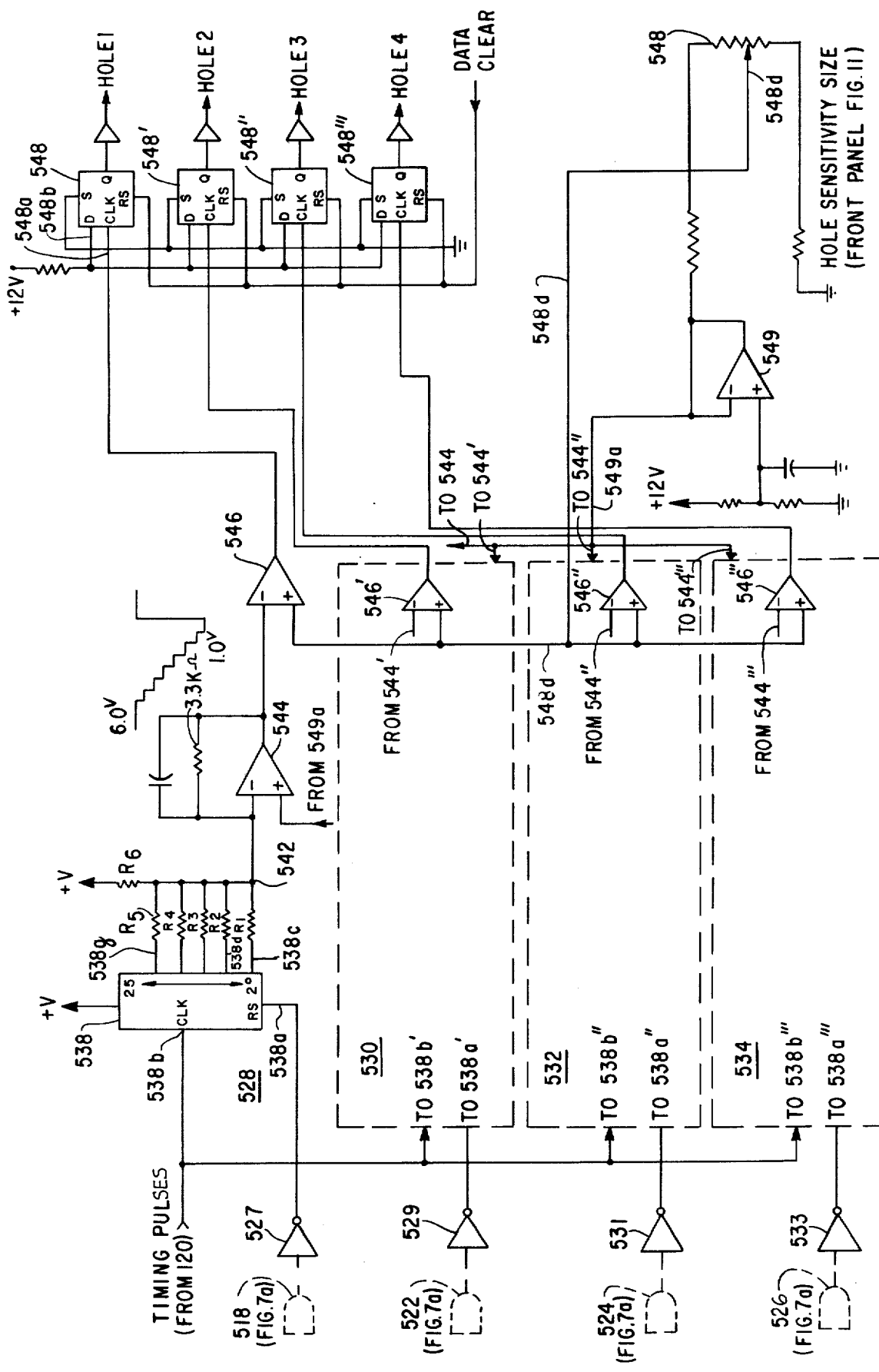

FIGS. 7a and 7b together comprise a schematic diagram showing the hole detection circuit of FIG. 2 in greater detail.

FIGS. 7c through 7g show waveforms useful in describing the operation of the hole detection circuit of FIG. 7.

Figure 8:
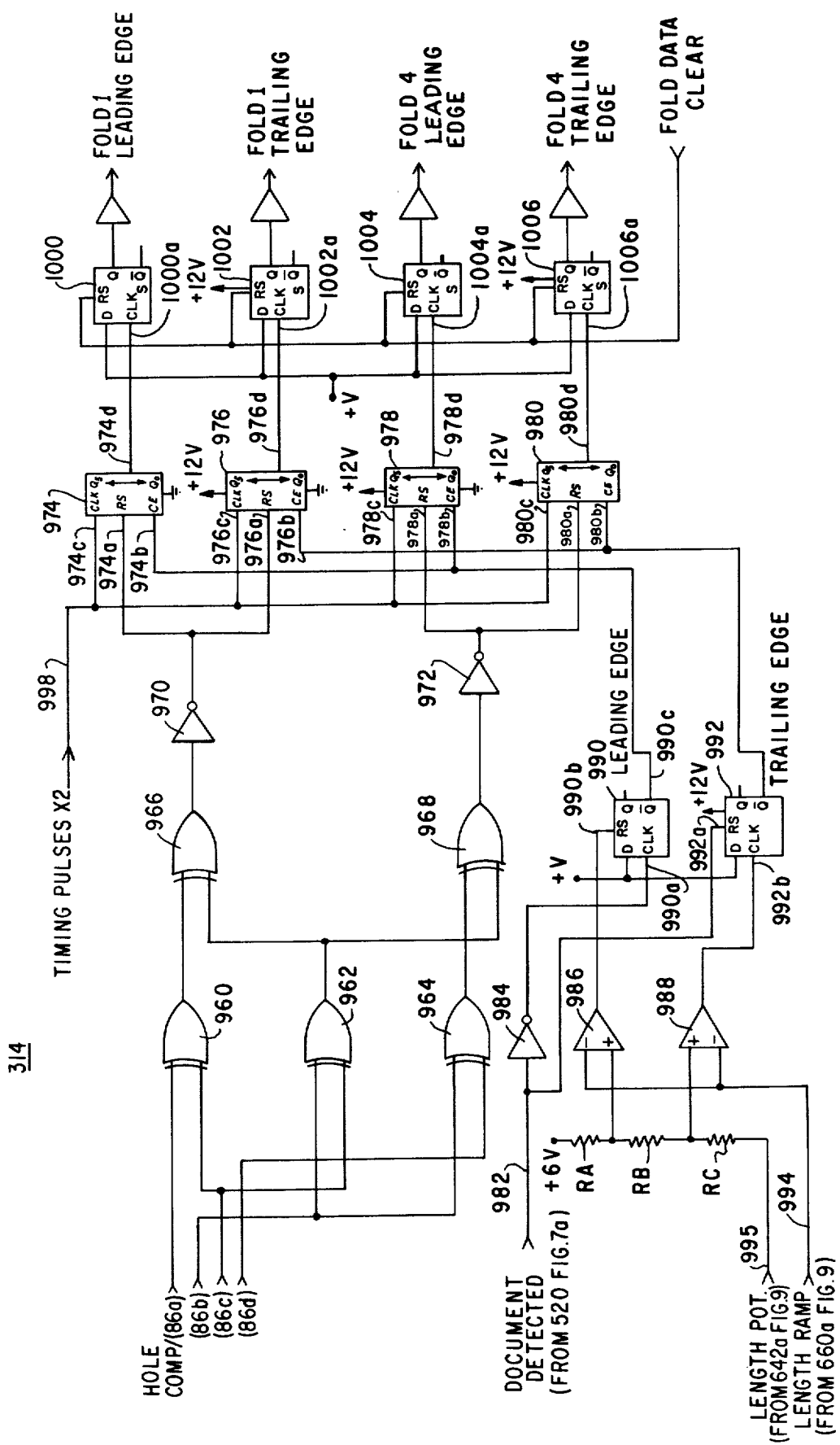

FIG. 8 is a schematic diagram showing the folded and/or missing corner detection circuit of FIG. 2 in greater detail.

Figure 9:
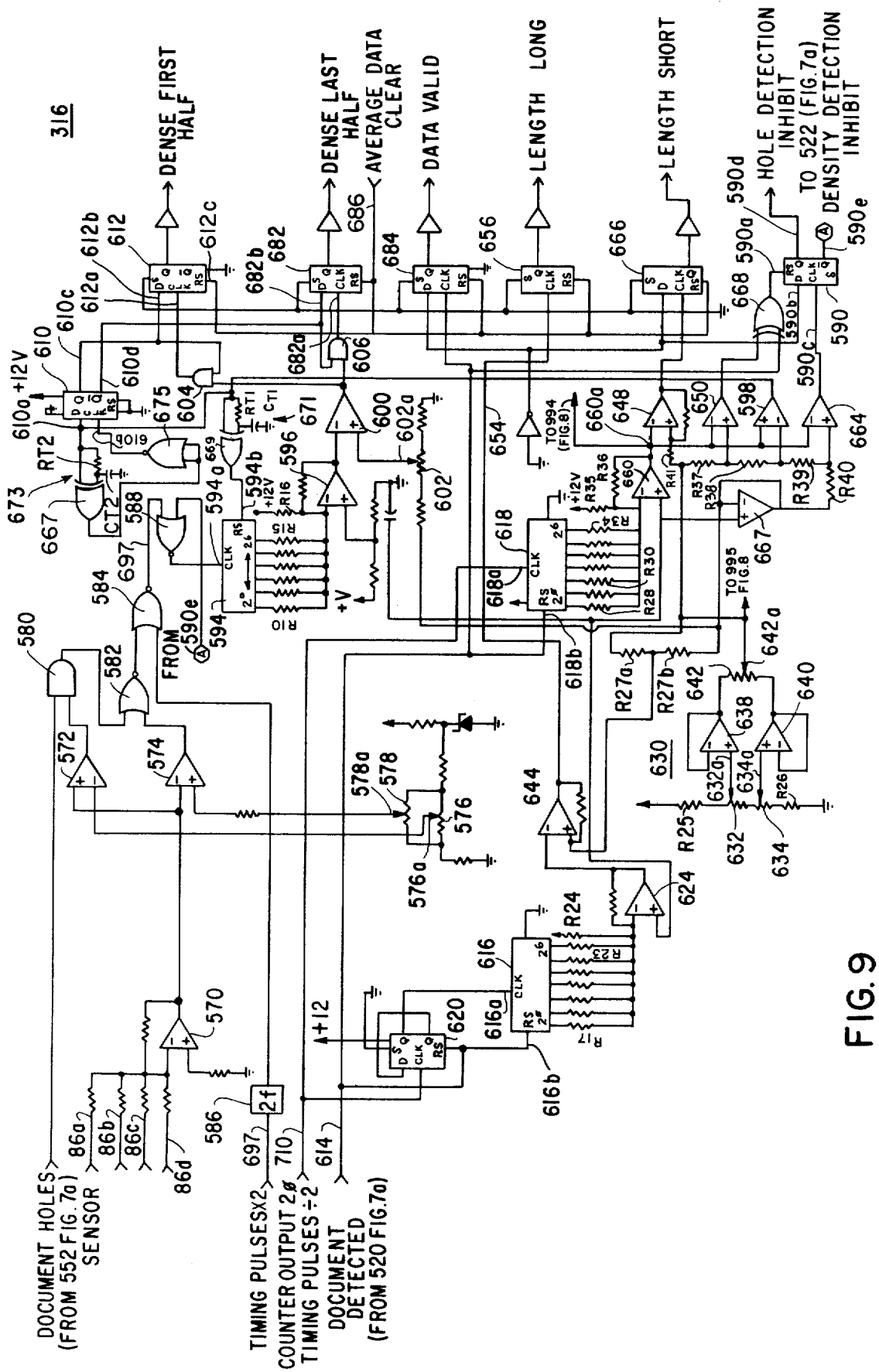

FIG. 9 is a schematic diagram showing the average density detection and length measuring circuit of FIG. 2 in greater detail.

Figure 10:
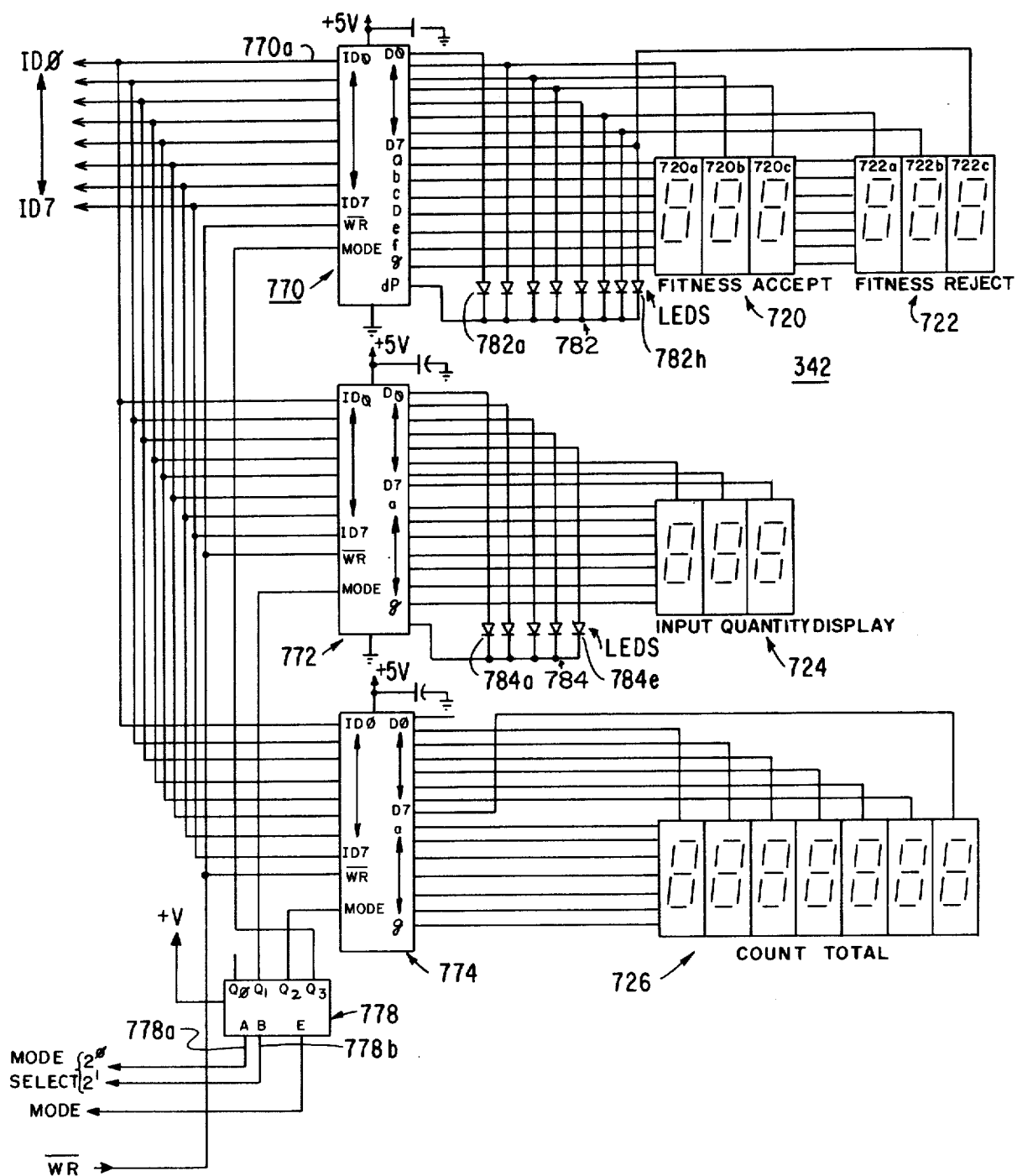

FIG. 10 shows a block diagram of the display circuit of FIG. 2 in greater detail.

Figure 11:
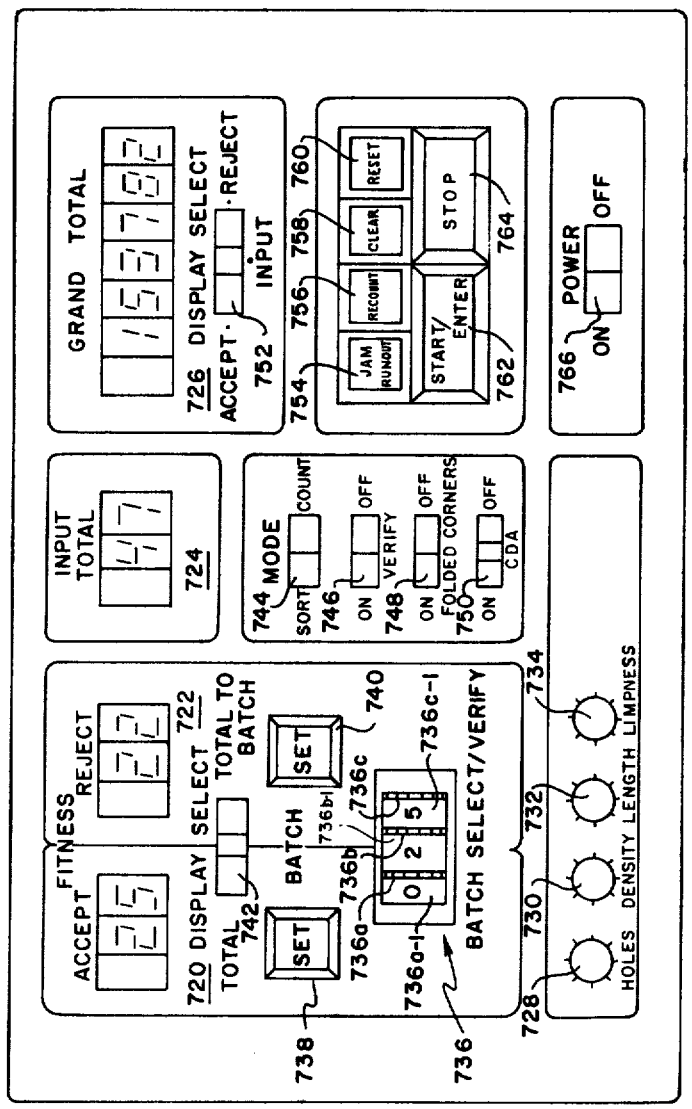

FIG. 11 is a plan view showing the keyboard and control board of FIG. 2 in greater detail.

FIG. 12 shows a family of waveforms useful in describing the operation of the microprocessor of the present invention.

Figure 3B:
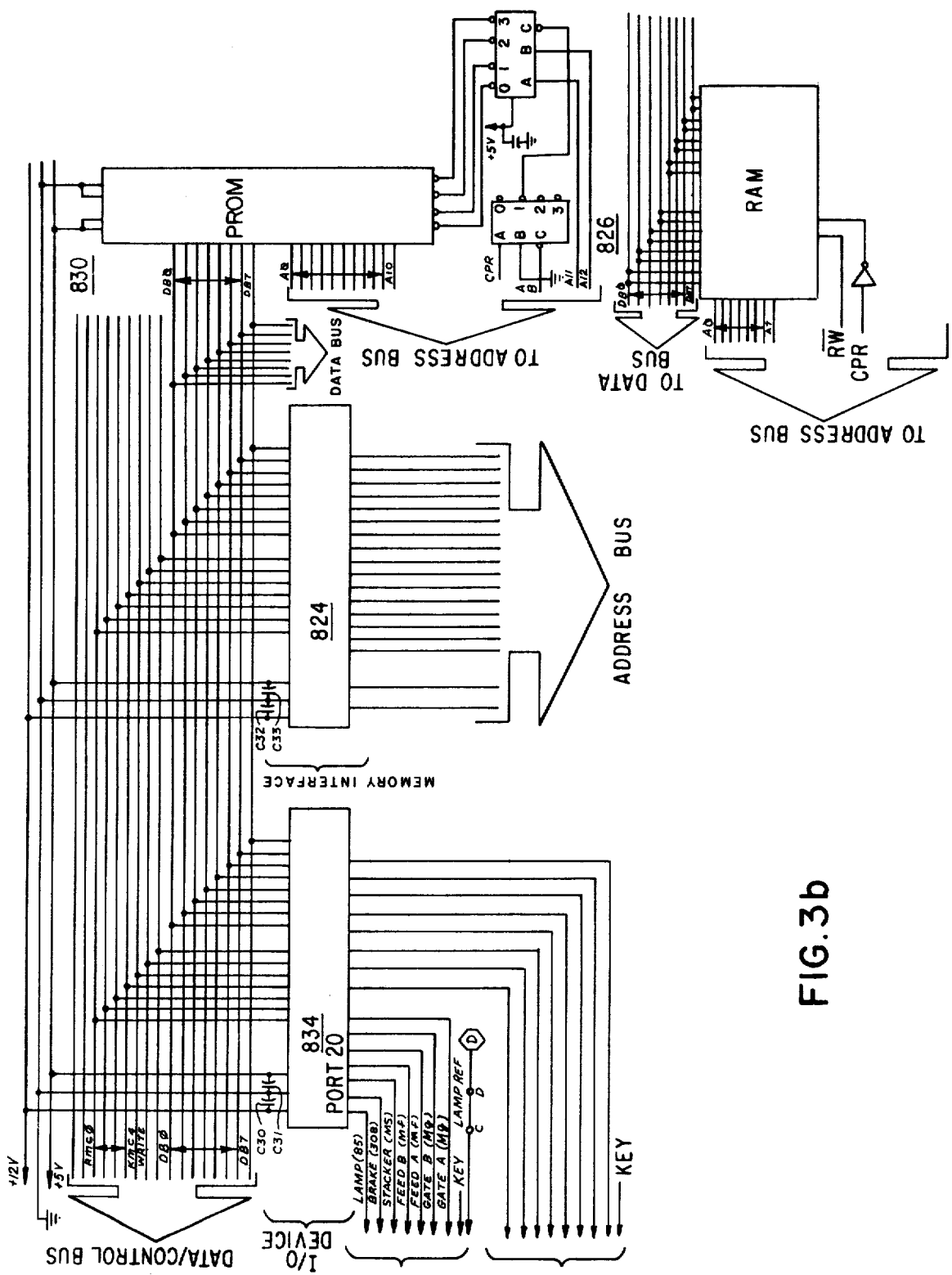

FIGS. 13, 14, 15, 16, 17, 18, 19, 20, 21, 22, 23, 24, 25, 26, 27, 28 and 29 are flow diagrams useful in explaining the operations performed by the microprocessor-based control of FIGS. 3a, 3b.

DETAILED DESCRIPTION OF THE BEST MODE OF CARRYING OUT THE INVENTION

Figure 1:
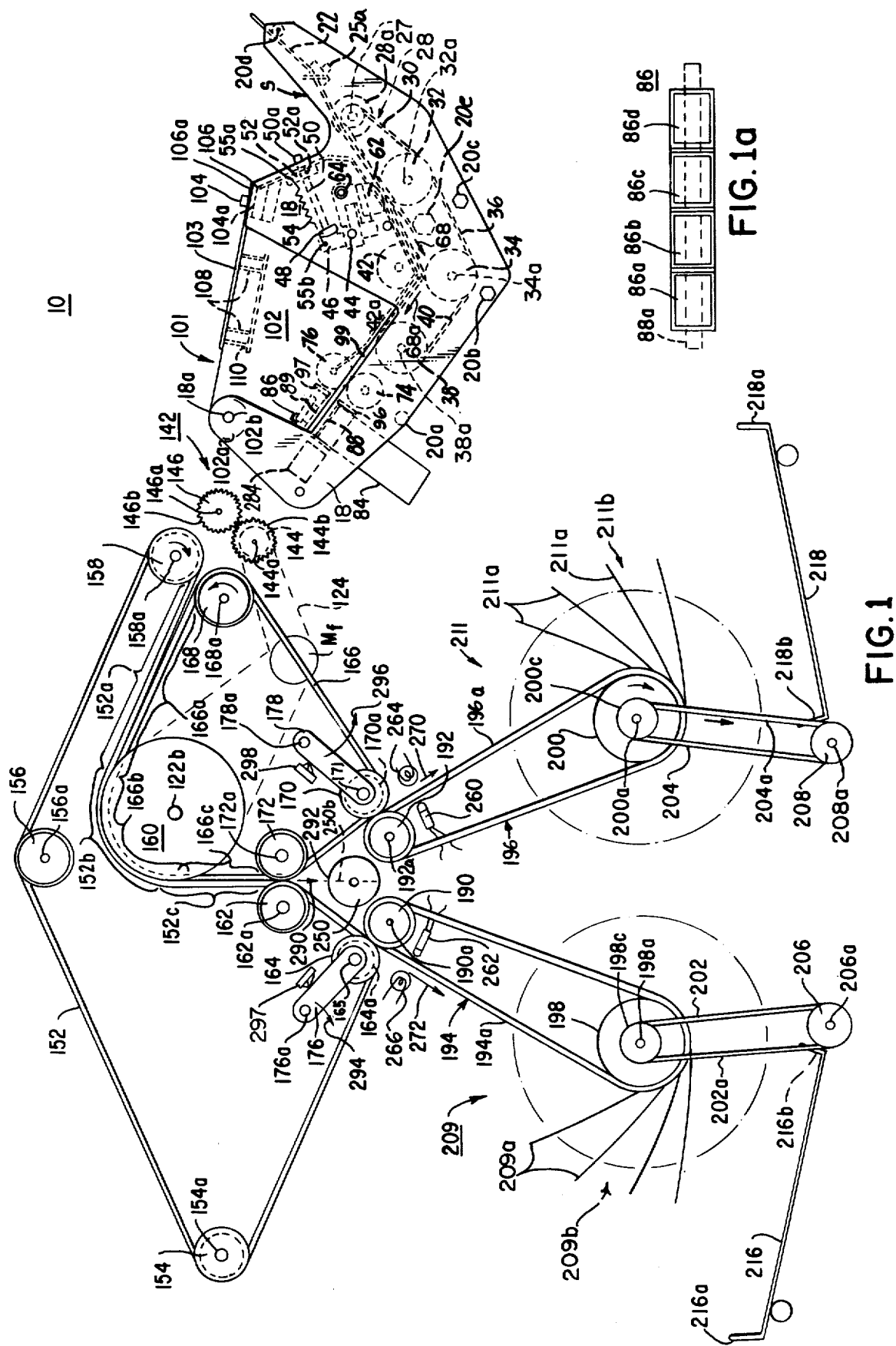
FIG. 1 shows a simplified plan view of a document handling apparatus designed in accordance with the principles of the present invention.

FIG. 1 shows document handling, examining and counting apparatus 10 embodying the principles of the present invention. A detailed description of the apparatus of FIG. 1, as well as the power train and other associated apparatus is set forth in detail in copending application Ser. No. 188,906 filed Sept. 19, 1980 and assigned to the assignee of the present application. For purposes of understanding the control system of the present invention, it is sufficient to understand the operation of the apparatus of FIG. 1 which will be described hereinbelow. A more detailed understanding of the power train and the manner in which it operates the document handling examining and counting apparatus 10 can best be derived from the aforementioned copending application Ser. No. 188,906 whose teachings are incorporated herein by reference thereto.

The sheet feeding mechanism 10 is comprised of a plate 18 which is mounted to a supporting surface 12 supporting mechanism 10 by suitable mounting means such as rods 20a through 20e which are secured to the face of plate 12 and extend outwardly therefrom and in turn have plate 18 secured thereto by suitable fastening members. Plate 18 cooperates with supporting surface 12 to serve as cover means for the mechanisms arranged therebetween. Plate 18 and spacers and supports 20a through 20e serve as the means for positioning and supporting an elongated plate 22 which functions as both an infeed hopper and a guideplate for guiding sheets through the apparatus. The upper end 22a of plate 22 supports a substantially C-shaped channel 24 shown in FIG. 1a of application Ser. No. 188,906, whose base portion 24a rests upon the upper surface of plate 22 and whose upright arms (only arm 24 being shown in FIG. 1) extend upwardly therefrom, to serve as a means for receiving a stack S of sheets to be processed by apparatus 10, said stack S being supported between the aforesaid upright arms and upon surface 24a.

The sheets are supported by portion 22a and the next adjacent portion 22b of plate 22 and occupy the region generally as represented by the trapezoidal shaped dotted region S. A hole is provided in the base portion 24a of channel 24. A light source 25a and sensor 25b, also shown in FIG. 2, are positioned adjacent to said hole. When sheets are stacked in the infeed hopper, light is reflected from the bottom sheet in the stack S towards sensor 25a. In the absence of a stack, no reflected light reaches sensor 25a which develops a signal compared against a predetermined threshold which is adjusted to provide a sheet present signal which is higher than the signal due to ambient light. Alternatively, the signal from source 25a may be a predetermined frequency and a filter 25c passes light of only the aforesaid frequency to prevent ambient light from being interpreted as the presence of a document.

A shaft 26 supports an eccentric picker roller assembly 28 mounted to rotate upon shaft 27 and having a central eccentric portion 28a and opposing concentric outwardly extending ends. Only end section 28b and central section 28a are shown in FIG. 1 for purposes of simplicity. The outer ends each have annular grooves about their periphery for supporting and receiving a resilient O-ring belt. As shown in FIG. 1, O-ring belt 30 is entrained about the annular groove provided therefor in end section 28b of picker roller 28. The ends of roller 28 are concentric about shaft 27, while center portion is eccentric relative to shaft 27 as was mentioned hereinabove.

Resilient O-ring 30 is also entrained about a roller 32 having an annular shaped groove surrounding said roller and adapted to position and seat said O-ring. Although not shown for purposes of simplicity, a second annular groove is provided on the opposite end of roller 32 and has extrained therearound a second O-ring, similar to O-ring 30 and which is entrained about the opposite end projection of eccentric roller 28, which opposite projection has not been shown for purposes of simplicity.

A roller 34 is positioned downstream from roller 32 and is mounted to rotate about shaft 34a. Roller 32 is mounted to rotate about shaft 32a. Additional annular grooves, which are axially spaced from the previously mentioned grooves, are provided about the periphery of roller 32 to position and seat O-ring 36 and an additional O-ring (not shown). Cooperating grooves are provided at like locations about the periphery of roller 34 to seat the last-mentioned O-rings, only O-ring 36 being shown for purposes of simplicity. A roller 38 is positioned downstream from roller 34 and is mounted to rotate about shaft 38a. An O-ring 40 and a second O-ring (not shown) similar thereto are entrained about rollers 34 and 38 which rollers are both provided with annular grooves for seating and positioning a pair of such O-rings, only one O-ring, namely O-ring 40, being shown in FIG. 1 for purposes of simplicity.

A roller 42 mounted to rotate about shaft 42a is positioned just above the surface of roller 34.

Plate 18 is provided with an opening for receiving shaft 44. An elongated arm 46 is secured to shaft 44 and has its right-hand edge resting against the left-hand surface of member 48 which is secured to the left-hand end of threaded member 50. Member 50 threadedly engages a tapped opening 52a in a mounting block 52, secured to plate 18. Threaded member 50 is provided with a slotted end 50a for receiving the head of a screwdriver to facilitate its adjustment. A spring means 54 extends between a pin 55a provided on mounting block 52 and a pin 55b provided near the upper end of arm 46 for normally urging arm 46 clockwise about shaft 44. By adjusting threaded fastening member 50, the angular orientation of arm 46 about its axis of rotation, i.e. the center of shaft 44, may be simply and readily adjusted.

Also pivotally mounted upon shaft 44 is an elongated stripper assembly supporting arm 56 which is locked to swing with shaft 44. The forward free end of mounting arm 56 is provided with a pin 58 for supporting swingable stripper support 60. A solid stripper member 62 is secured to the underside of swingable support member 60, typically by suitable fastening means (not shown). A torsion spring 64 has its opposing ends respectively secured to arm 66 and a swingable member 60, urging member 60 counterclockwise about the axis of pivot pin 58 relative to arm 56. Thus springs 54 and 64 tend to resiliently urge stripper member 62 into engagement with the adjacent portion of roller 32, while at the same time being yieldable to relieve a possible jam condition, i.e. to relieve the sudden build-up of a curled document or two or more overlapping documents which move between stripper member 62 and roller 32.

The confronting surfaces of members 62 and 32 have differing coefficients of friction whereby, when a single document passes therebetween, the surface of roller 32 exerts the prevailing influence upon a single document, enabling the document to pass in the forward feed direction, as shown by arrow 68. In the event that two documents are simultaneously fed between members 62 and 32, the coefficient of friction between the two documents is substantially less than the coefficient of friction between the lower document and the surface of roller 32, allowing the lower document to move in the forward feed direction 68. The coefficient of friction between member 62 and the upper document is also greater than the coefficient of friction between the two documents causing the upper document to be impeded from moving in the forward feed direction, thereby stripping the overlapping sheets fed therebetween to substantially assure that the sheets will be fed in a single file past the position of the nip formed between members 62 and 32.

The support members 20f, 20g and 20h which substantially perform the same functions as support members 20a through 20e, in addition to supporting plate 18, support an upper plate 70 having a plurality of bends therein which define flat portions between said bends, said flat portions being designated 70a through 70e. Portions 70a, 70b and 70c cooperate with portions 22a and 22b of guideplate 22 to define a stacker region for supporting a stack S of sheets and further, to define a tapering entrance throat portion between plate portions 70b–70c and 22b.

Sheets in stack S which rise above portion 70b have their leading edges resting against plate portion 70a which serves to relieve the portion of the stack therebeneath from a part of the weight exerted on the stack S by sheets arranged above the corner between portions 70a and 70b.

The central portion 28a of eccentric roller 28 is preferably fitted with a pair of O-rings (not shown) to provide good frictional engagement between the O-rings and the bottommost sheet in the stack S of sheets. The eccentric portion 28a of roller 28 together with the last-mentioned O-rings, serve to "jog" the stack upwardly and to exert a frictional force on the bottommost sheet, to drive the bottommost sheet in feed direction 68 to cause the sheet to be moved between members 62 and 32 for the feeding and stripping operations, as was described hereinabove.

Sheets moving past members 62 and 32 pass between plate portions 22c and 70d and are guided by the upper runs of O-rings 36 and 40 and the surface of roller 42, causing the sheets, being fed in single file, to undergo a change in direction, initially being fed generally diagonally downward as shown by arrow 68 to being fed generally diagonally upward as shown by arrow 68a. Roller 42, freewheeling mounted on shaft 42a, is arranged to smoothly guide sheets as they make the transition from being moved off of the upper run of O-ring 36 and on to the upper run of O-ring 40.

As sheets move along the upper run of O-ring 40 and pass over roller 38, the sheets are guided between the surface of roller 38 and guideplate portion 70e where they are caused to enter into the nip between roller 74, mounted to rotate upon shaft 74a, and idler rollers 76.

A pair of idler rollers are resiliently positioned above roller 74 and are resiliently mounted by suitable leaf spring means. As shown for example in FIG. 1, one such idler roller 76 is mounted to rotate about shaft 76a which is supported by the free end 78a of leaf spring 78 whose opposite end is secured to swingable plate 99 by fastening means 80, swingable plate 99 forming part of a swingably mounted unit 101, to be more fully described.

The rpm (revolutions per minute) of roller 74 exceeds the rpm of roller 38, so that, as documents enter into the nip between rollers 76 and 74, they are abruptly accelerated to move at a higher linear velocity, causing the trailing edge of the document fed through the nip formed by rollers 74 and 76 to move a predetermined spaced distance from the leading edge of the next document to be fed to said nip, providing a gap between said trailing and leading edges sufficient to perform counting and sensing operations on said sheets.

The roller 74 preferably has a surface with a high coefficient of friction. The rollers 76 are provided with grooves for receiving and supporting an O-ring, such as O-ring 84 to be assured that the accelerating force is imparted to sheets with a minimum of slippage.

Positioned immediately downstream of the acceleration roller 74 and idler roller 76 is a light source assembly 84 and a light sensor array 86. Light source 84 is comprised of a housing containing a lamp, preferably a halogen lamp (not shown). The cover plate 88 over the end of housing 84 adjacent to the feed path 68a is transparent. An opaque mask is provided upon the cover plate to enable only an elongated slit of light to be passed upwardly through transparent plate 88 toward the light sensor array 86. Array 86 is comprised of a plurality of sensors, such as for example the sensor 86a. The remaining sensors 86b–86d are arranged in an end to end fashion so as to be substantially aligned with the elongated slit provided in transparent cover plate 88. A similar transparent cover plate 86e is provided across the bottom surface of array housing 86.

As shown best in FIG. 1, the array assembly 86 is comprised of a housing aligned with a slit 92 in swingable plate 90 which slit 90 is divided into four compartments, each of which receives and supports the sensing surface 86a through 86d of an associated sensor element 86. As can be noted, each sensor surface has a rectangular shape. Elongated narrow dotted rectangle 88a represents the slit provided in the mask formed over the upper end of the light source housing 84 to define the region over which light is emitted from the light source assembly 84 and toward the light sensor array 86.

A preview sensor 94 is positioned above an opening in plate portion 70e and cooperates with a light source, preferably an LED 96, to function as a preview sensor for a purpose to be more fully described. Note also FIG. 2.

The swingable plate portion 99 upon which the idler rollers, such as idler roller 76 and the sensor array 86 is mounted, forms part of swingably mounted unit 101 having a plate 102 with a mounting portion 102a provided with an opening 102b for cooperating with the opening 18a in plate 18 for swingably mounting assembly 101. Assembly 101 has a cover lid portion 103 mounted upon a pair of spaced parallel side plates 102 and a plate (not shown) similar thereto, which lid rotatably mounts a fastening member 104 in a freewheelingly fashion. The lower end 104a of freewheeling mounted fastening member 104 is adapted to threadedly engage a tapped aperture 106a in block 106 which is secured between plate 18 and mounting plate 12. Thus, the swingably mounted assembly 101 serves to facilitate examination of the sensor array assembly as well as other internal mechanisms and/or components contained therein.

Lid 103 supports a group of spacer rods 108 which are secured at their upper ends to lid 103 and which position and support a printed circuit board 110 at their lower ends, said printed circuit board 110 supporting electronic components which cooperate with sensors 86a through 86d of the sensor array 86 for providing signals utilized for sheet examination and evaluation purposes, as will be more fully described.

The rollers 28, 32, 34, 38 and 74 are all driven by the feed motor $M_f$ (note also FIG. 2), the driving coupling as was described hereinabove, being obtained through the power train described in detail in copending application Ser. No. 188,906. Motor Mf as shown in FIG. 2, has an output shaft 112. A gear 114 is mounted upon shaft 112. Gear 114 is provided with a plurality of gear teeth 114a about its periphery and is secured to the feed motor output shaft 112 to rotate in unison with shaft 112. A light source 118 and a light sensor element 120 are positioned on opposite sides of gear 114 adjacent to the periphery thereof whereby teeth 114a pass between members 118 and 120 to cause light from source 118 reaching sensor element 120 to be modulated in a pulse-like fashion for generating system timing pulses to be employed in a manner to be more fully described.

The aforementioned power train is designed in one exemplary embodiment to cause the picker roll 28 to rotate at a speed which imparts movement to the document so as to be capable of achieving a velocity of 113 ips (inches per second). The feed roller 32 is rotated at a speed capable of moving documents along feed path 68 at a linear velocity of 106 ips. The acceleration roller 74 rotates at a speed sufficient to accelerate sheets so that they reach a velocity of 176 ips.

A limpness detector assembly 142 is located downstream from the light source and sensor array 84, 86, and is comprised of a pair of elongated generally cylindrical-shaped members 144 and 146, each mounted to rotate about shafts 144a and 146a and each having a gear-like periphery 144b and 146b respectively. Shaft 146a is mounted upon a a swingable arm (not shown) which is resiliently biased to normally urge gear-like roller 146 toward gear-like roller 144. As sheets pass therebetween, a counterforce is exerted upon gear-like rollers 144, 146, the magnitude of the counterforce being a function of the relative stiffness or relative limpness of sheets passing therebetween, thereby limiting the movement of gear-like member 146 toward gear-like member 144. Members 146 and 144 are mechanically coupled and driven so that the teeth of one of said gear-like rollers at least partially enters into the grooves arranged between the teeth of the other of said gear-like rollers and vice versa, in order to impart an undulating configuration to the sheet passing therebetween. The degree of said undulations is a function of the interaction between the force exerted upon the sheet by gear-like rollers 144 and 146 and the counterforce exerted by the sheet passing therebetween upon gear-like rollers 144 and 146. For example, very stiff sheets do not experience any bending, while extremely limp sheets such as thin onion-skin sheets, undergo a maximum amount of bending. A detailed description of the limpness detector is set forth in copending application Ser. No. 188,906 filed Sept. 19, 1980 and assigned to the assignee of the present invention.

The aforementioned driving coupling assures substantially synchronised rotation of gear-like rollers 144 and 146 in order to assure the proper entry of the teeth of gear-like roller 144 into the grooves arranged between the teeth of the other gear-like roller 146, and vice versa.

A pair of elongated O-rings, only O-ring 152 being shown in FIG. 1, are entrained about pulleys 154, 156, 158, 160, 162 and 164. Another pair of O-rings, only one such O-ring 166 being shown in FIG. 1, are entrained about pulleys 160, 168, 170 and 172. Pulleys 154, 156, 158, 162, 164, 170 and 172 are all freewheelingly mounted so as to be driven by O-rings 152 and/or 166. Pulleys 154, 156, 158, 160, 162 and 172 are all mounted to rotate about shafts 154a, 156a, 158a, 122b, 162a, 172a and 168a, all of which are mounted in a stationary fashion so that they are capable only of rotating about their central axes.

Pinch rollers 164 and 170 are rotatably mounted upon shafts 165, 171 provided at the free ends of a pair of swingable levers 176 and 178 in a freewheeling manner, each being pivotally mounted to support surface 12 by pivot pins 176a and 178a respectively. Centrally located pulleys 164a and 170a, shown in dotted fashion, are also freewheelingly mounted upon shafts 165, 171 and rotate independently of pinch rollers 164, 170. Pulleys 164a, 170a have recesses for receiving and seating O-rings 152, 166. The diameter of pinch rollers 164a, 170a, is greater than the diameter of the pulleys 164a, 170a to prevent O-rings 152, 166 from engaging pinch rollers 190, 192 and O-rings 194, 196.

The linear portion 152a, curved portion 152b and linear portion 152c of the path defined by O-ring 152, cooperates with the linear portion 166a, curved portion 166b and linear portion 166c of the path defined by O-ring 166 to cooperatively define a conveying path between which sheets exiting from the limpness detector assembly 142 are caused to be fed in a generally diagonally upward direction along path portions 152a, 166a and thereafter experiencing movement along a curved path portion 152b–166b, whereupon the documents are then moved in a generally downward vertical direction, as sheets move between path portions 152c–166c. Based upon the exemplary values set forth hereinabove, the sheets are moving at the same linear velocity through the path defined by O-rings 152 and 166 as they move through the limpness detector assembly 142 and the acceleration roller and cooperating idlers, namely, 176 inches per second.

Still considering FIG. 1, a pair of pinch rollers 190 and 192 are mounted to rotate about shafts 190a and 192a each having entrained thereabout an O-ring 194, 196. O-rings 194 and 196 are seated in grooves provided at the central portion of the pinch rollers 190, 192 and are further entrained about a directly driven large diameter pulley 198 and 200 respectively, each rotating about a shaft 198a, 200a respectively. Each of the pulleys 198, 200 has integrally joined thereto and extending from both sides thereof a pair of smaller diameter pulley portions so that the pulley 198 is arranged between the aforesaid smaller diameter pulley portions. Only one such small diameter pulley portion, namely portions 198c and 200c, is shown in FIG. 1 for purposes of simplicity, it being understood that each of these pulley portions receive and support an O-ring 202 and 204 which is further entrained about a cooperating pulley 206 and 208 respectively, each rotating about shafts 206a and 208a respectively.

The pulleys 198 and 200 further support rotary fan-like stacker wheels 205, 207 comprised of a plurality of curved resilient blades 210, 212, arranged at spaced intervals in the manner shown so as to form pockets 211, 213, between adjacent pairs of resilient blades 210, 212. Each sheet is adapted to be driven into one of said pockets in a manner to be more fully described. The sheets are subsequently stripped from their pockets by O-rings 202 and 204 and thereafter deposited upon an associated stacking plate 216, 218, each having upright sides 216a, 216b and 218a, 218b, for supporting and gathering sheets thereon. Upright walls 216b and 218b are provided with clearance slots to permit unimpeded movement of the run 202a, 204a, of O-rings 202 and 204 respectively.

One exemplary embodiment is designed so that the runs 194a and 196a of O-rings 194 and 196 are driven at a velocity such that sheets passing through the nip between pinch rollers 164–190 and 170–192 are accelerated to achieve a linear speed of the order of at least 178 ips in order to quickly "grab" the leading edge of the sheet after it has been deflected by the gating roller 250. The stacker wheels 205, 207, are mounted upon the shafts 198 and 200 which also rotatably support the pulleys 254 and 252. The stacker wheels 205, 207 are rotated so that the tip speed at the free ends of curved flexible fingers 210 and 212 is of the order of 28 ips. The much higher linear speed of the sheets assures insertion of each of the sheets deeply into a pocket 213. The curvature of the pocket 213 serves to decelerate each sheet as it enters the pocket 213.

A gating roller 250, mounted for rotation upon the gating roller motor shaft 252, is adapted to rotate in either a clockwise or counterclockwise direction, dependent upon the polarity of the driving signal applied to the gating motor Mg by the microprocessor.

The gating motor Mg is preferably a d.c. motor capable of rotating at a speed in the range of 2,000 to 8,000 rpm and preferably of the order of at least 3,600 rpm, and which is capable of rapidly reversing direction and reaching its maximum rpm in the reverse direction within an extremely short time interval.

In order to be assured that sheets are deflected in the proper direction by gating roller 250, as will be more fully described hereinbelow, a pair of sensor elements 260 and 262 are arranged just downstream of pinch rollers 190 and 192. A pair of light sources 264 and 266, which may for example be light emitting diodes (LEDs) are arranged adjacent to the sensors 260, 262 respectively so that, as sheets pass therebetween as represented by arrows 270 and 272, the light rays from each source are attenuated by the presence of the sheet causing the reduced brightness condition detected by sensors 260 and 262 to be interpreted as the passage of a sheet, which information is utilized by computer control means 280 (see FIG. 2), to control the operation of the apparatus.

The operation of the document handling examining and stacking system is as follows:

A stack of sheets which may, for example, be paper currency, are placed in the infeed hopper. See stack S of FIG. 1. When the document handling apparatus 10 is turned on, the rotation of the eccentric picker roller 28 jogs the stack S upwardly and its O-rings (see O-ring 72) frictionally engage the bottommost sheet, accelerating the bottommost sheet in the forward feed direction 68 whereby the bottommost sheet is advanced through the tapering throat portion to move into the nip formed between stationary stripper member 62 and feed roll 32. Members 62 and 32 cooperate in the manner described hereinabove to assure that sheets are fed in a single file as they pass through the aforesaid nip between members 62 and 32 and are advanced in the feed direction shown by arrow 68. The sheets undergo a turn at rollers 42 and 34 and thereafter move in an upward diagonal direction shown by arrow 68a. The sheets are abruptly accelerated by acceleration roller 74 and cooperating idler 76 in order to form a gap between the trailing edge of the document accelerated by accelerator roll 74 and the leading edge of the next document to be fed therethrough, said gap being of a length sufficient to prevent overlapping between documents and thereby facilitating counting of documents as well as providing an interval between sheets sufficient to enable the control circuitry to perform certain functions such as the gain control adjustment of the sensors, as will be more fully described hereinbelow.

As the sheets, which in the example given hereinabove, are moving at a linear speed of the order of 176 ips, pass between lamp source 96 and sensor 94 and subsequently between sensor array 86 and light source 84, the signal conditions from the sensors of array 86 and from sensor 97 are fed to computer control 280. The type of tests performed on the sheets, which may for example be paper currency, are: density of the sheets, i.e. are they "clean" or "dirty"; do the sheets have tears, cuts, slits or perforations; are there folded or torn corners; and are the sheets of the proper length, i.e. are they too long or too short.

The limpness detection assembly 142 is designed to detect the relative limpness or stiffness of the sheets and is further designed to indicate the presence of foreign material or members affixed to the sheets, for example, masking tape or transparent tape, staples and the like, which materials are often used to repair a torn bill. The limpness detector assembly 142 also serves as a means for indicating the presence of folded corners, as well as erroneous double feeding of documents by providing a "too stiff" signal in the event of passage of two documents in an overlapping fashion. Signals from the limpness detector apparatus 142, as will be described in detail hereinbelow are also provided to computer control circuit 280 in order to control the apparatus in accordance with the test or tests being performed.

In addition to the above, it is also possible to provide a counterfeit detection apparatus 284 which is positioned between the limpness detector assembly 142 and the sensor array 86, in order to detect the presence of suspect (i.e. possible counterfeit) bills. Counterfeit detection apparatus of this type is described in U.S. Pat. No. 4,114,804 issued Sept. 19, 1978 and assigned to the assignee of the present application. The counterfeit detection apparatus represented by black box 284 also provides its signals to one input of the computer control 280 which further receives signals from the post gate detectors 260 and 262 and which further provides control signals to the feed, stacker and gate motors Mf, Ms and Mg respectively.

The computer control 280 is provided with selection means for example, adapted to select those tests which are to be performed, it being understood that none, all or less than all of the tests can be performed simultaneously depending upon the setting of the selection members to be more fully described in connection with FIG. 11.

The first and second output stacking platforms 216 and 218 may arbitrarily be assigned to respectively stack fit and unfit documents, fit documents being described as those which meet the desired criteria based upon the tests being performed, and unfit documents being those which fail to meet the desired criteria. For example, documents which are too limp and/or too stiff may be collected upon stacker plate 218 while documents that meet the desired criteria, i.e., fall between the criteria of being too stiff and too limp, are stacked upon stacker plate 216.

Based upon receipt of the appropriate information, computer control 280 is designed to apply a signal of the appropriate polarity to gating motor Mg in order to rotate the gating roller 250 in the proper direction. Let it be assumed that the last document tested is now entering into the sheet conveying path formed by O-rings 152 and 166, and that this sheet, in accordance with the signals applied to computer control 280, has been classified as unfit. Computer control 280 will therefore apply a signal to gating motor Mg at a time sufficiently in advance of the sheet entering into the conveying path formed by O-rings 152 and 166, to be assured that gating roller 250 reaches its desired operating speed before the leading edge of the document to be appropriately diverted reaches gating roller 250.

The path along which the next sheet to be diverted to the appropriate output stacker is moved, advances the sheet along a path 290 which lies substantially along an imaginary diameter 250b of gating roller 250 so that the leading edge of the sheet will strike the surface of gating roller 250 at an angle which is substantially perpendicular to an imaginary line which is tangent to the surface of gating roller 250 and which intersects path 290 at point 292. By rotating gating roller 250 at a sufficiently high speed (i.e. rpm), proper deflection of the sheet is made possible. For example if the rotating speed is too low, since the sheet is moving at a very high rate of speed, in the example given 176 ips, the surface of roller 250 acts as a stationary wall and the sheet will simply bounce off of the surface of the gating roller and will not be properly deflected. However, when the tangential speed of the gating roller 250 is sufficiently high and is much greater than the linear velocity of the sheet, it is thus possible to deflect the sheets in a rapid and effective manner. In the example given, the gating roller 250 is caused to rotate clockwise, deflecting the leading edge of the sheet toward the right and causing the sheet to move into the nip formed between pinch rollers 170 and 192. The pinch rollers 170 and 192 "grab" the sheet and cause it to be accelerated as it is moved through the nip formed by pinch rollers 170, 192 and downwardly along the right-hand run 196a of O-ring 196 which serves as a means for moving sheets therealong as well as guiding said sheets toward and into the pockets 211b formed by adjacent pairs of fingers 211a. The O-ring 196 which may also be a flat belt, if desired, is formed of a resilient material having a relatively high coefficient of sliding friction which engages the sheet and serves to urge the leading edge of the sheet deeply into one of pockets 211b in stacker wheel 211. The curvature of each pocket 211b, defined by the curved fingers 211a serves to hold the sheet as the stacker wheel 211 rotates clockwise. The leading edge of the sheet in each pocket 211b bears against the right-hand run 204a of O-ring 204 which serves to strip the sheet from each pocket 213 as the inner ends of the fingers 211a begin to move past O-ring 204. Preferably a pair of O-rings are placed on opposite sides of each of the stacker wheels 209, 211. The stripped sheets are then caused to move downwardly where they are collected upon stacker plate 218. The leading edges of the sheets engage the right-hand run 204a of O-ring 204 which serves to drive the leading edges of the sheets downwardly to form a neat stack whereby the O-ring 204 serves the dual functions of stripping documents from the stacker wheel assembly 211 and serves to urge the leading edges of the documents downwardly towards the stacker plate 218.

Stacker wheel assembly 209, O-rings 194 and 202, and stacker plate 216, function in a manner identical to the corresponding elements 211, 196, 204 and 218 described hereinabove.

As was mentioned hereinabove, pinch rollers 164 and 170 are swingably mounted upon arms 176 and 178. The rollers 164 and 170 are designed to rotate clockwise and counterclockwise respectively, as shown by arrows 294 and 296. In order to permit the clearing of jam conditions occurring in the nips formed between rollers 164-190 and 170-192 respectively, arms 176, 178 are also free to swing in an over-center fashion in the event of a jam to provide an automatic arrangement for clearing a jam. Sensors in the form of microswitches 297 and 298 may be provided to indicate the release of swingable arms 176 and 178 from their operative position in order to provide indications to the computer control 280 to enable the computer control to take appropriate action.

The post gate sensors 260 and 262 function in a somewhat similar manner to provide signals to the computer control 280 in order to be assured that documents have been deflected in the proper direction by gating roller 250. Thus, for the example given hereinabove, assuming gating roller 250 to be rotating clockwise, computer control 280 will examine the signal derived from sensor 260 to be assured that a document has passed between sensor 260 and LED 264 at the proper time. In the event that this signal is not derived and/or an erroneous signal is derived from sensor 262, even though gating roller 250 is rotating clockwise, computer control 280 will interpret this data as an error condition and take appropriate action which preferably takes the form of deenergization of the feed motor Mf and the gating motor Mg, preferably allowing the stacker motor Ms to continue rotation to clear any documents from the region of gating roller 250 and collect said documents at stacker plates 216, 218.

The computer control 280 receives a signal from sensor 120 shown in FIG. 2 in order to provide proper timing for the apparatus. For example, assuming an ideal condition in which a local supply source provides an operating voltage of a precise voltage and frequency, all pulleys, belts and the like will be likewise rotating and moving at an ideal speed. However, in the event that there are any sudden surges and/or gradual changes in the operating voltage and/or frequency of the local source, and/or in the event that the motor undergoes an abrupt or gradual change in its operating characteristics, this will directly affect the operating speed of the aforesaid feed, stacker and gating motors Mf, Ms and Mg. However, by deriving timing pulses directly from one of said motors, namely the feed motor Mf, any changes, whether gradual or sudden, in the local supply source, are immediately reflected in the timing pulses developed off of timing gear 118 to assure proper operation of the apparatus due to the synchronous operation of the mechanical system and the system electronics.

The gating roller 250 is preferably a low mass member to facilitate its rapid acceleration and deceleration. To accomplish this, the gating roller 250 may assume a variety of configurations having low mass. One gating device suitable for this purpose is the cylindrical roller 250 shown in FIG. 1 which is comprised of material of low mass, such as cork. Other suitable gating rollers are described in detail in copending application Serial No.

FIG. 2 shows the solid state electronic control circuitry 280, comprised of a central processing unit 302 incorporating a microprocessor as will be more fully described in connection with FIGS. 3a and 3b. Output control line 304 is coupled to driver circuitry 306 whose outputs in turn are connected to brake means 308 and the gate, stacker and feed motors Mg, Ms and Mf respectively, to provide the signals for stopping and starting the motors and for energizing and deenergizing the brake means 308. Brake means 308 applies a braking force, represented by dotted line 308a, to the output shaft 112 of feed motor Mf.

As was mentioned hereinabove, the teeth 114a of timing gear 114 modulate light from light source 118 which may, for example, be an LED, which light is directed to sensor element 114 which may, for example, be a phototransistor. Appropriate power is applied to the light source and sensor elements 118 and 120 by coupling circuit 310 which receives the power source at terminal 310a and which provides the signal developed by light sensing element 120 at its output 310b. Output 310b is simultaneously coupled to associated inputs of the hole detection circuit 312, folded corner detection circuit 314, average density and length measuring circuit 316 and an 8-bit timing counter 320 provided as part of the central processing unit 302. The manner in which the timing pulses are utilized will be described in greater detail hereinbelow.

The aforementioned light emitting element 25a (FIG. 1) and cooperating light sensing element 25b shown also in FIG. 1, are coupled through line 322 to stack sensor input line 302a of microprocessor 302 to indicate to the microprocessor whether or not sheets are provided in the infeed stacker.

The aforementioned preview sensor means shown in FIG. 1 and comprised of a light source 96 and light sensing element 97, is located upstream relative to the sensor array 84 and is utilized to initiate a gain adjustment operation in a manner to be more fully described. The outputs of detector 97 are coupled through preamplifier circuit 324 and its output line 324a to one input of the automatic gain control circuit 326.

The limpness sensor is comprised of a permanent magnet 328 mounted in a stationary fashion and cooperating with a swingably mounted, hall-effect device 330 which undergoes displacement relative to magnet 328 as a function of the displacement between movably mounted gear-like roller 146 and stationary mounted gear-like roller 144. The hall-effect sensor 330 develops a signal applied to a preamplification circuit 332 whose output signal 332a is coupled to inut 334a of limpness detection circuit 334. The limpness detection circuit compares the limpness sensing signal against predetermined threshold levels as will be more fully described hereinbelow, to develop a pair of output signals each capable of assuming either one of two binary states, said signals being applied through a pair of lines, represented in FIG. 2 by line group 334b, which signals are applied to an associated pair of inputs identified as 302b in FIG. 2, said inputs being described in greater detail hereinbelow.

The post gate sensors 260, 262 and their associated LED's 264, 266 as were described in connection with FIG. 1, are also shown in FIG. 2. The outputs 260a and 262a of sensors 260 and 262 are coupled to input ports 302c, 302d respectively, of the central processing unit 302.

The lamp assembly 84 referred to in FIG. 1 utilizes a halogen lamp 85 whose voltage is regulated by lamp regulator circuit 346 to provide a supply voltage whose levels are accurately controlled within tight tolerances in order to prevent the halogen lamp from developing temperature levels which are either too high or too low, either of which conditions tend to significantly shorten the life of the lamp. In addition, the lamp regulating circuit also assures that the lamp operates at the optimum brightness level.

As was described hereinabove, the output of the halogen lamp is passed through the transparent slit 88a provided in the mask position over the lamp housing (see FIG. 1a). The sensors 86a through 86d have their outputs respectively coupled to inputs of associated preamplifiers within preamplifier circuitry 324. The amplified output signals appearing in the output line group 324c are applied, together with the preview sensor signal in line 324d to associated inputs 326a and 326b respectively, of the automatic gain control circuit 326.

The outputs of sensors 86a through 86d after undergoing amplification and gain control adjustment, are applied through line group 326c simultaneously to the inputs 312a, 314a and 316a of hole detection circuitry 312, folded corner detection circuit 314 and average density and length measurement circuit 316, respectively.

The amplified output of the preview sensor 97 appears at output 326d of automatic gain control circuit 326 and is applied to input 302e of central processing unit 302 for initiating a gain control adjustment operation, as will be more fully described. A gain reference voltage level is applied to input 326d of circuit 326 from voltage reference level circuit 336 which provides all of the required reference levels necessary for use as supply voltages, as well as reference level voltages utilized by the various detection circuits.

The hole detection circuit 312 utilizes the system timing pulses derived from the feed motor Mf at input 312c, the signals from the sensors of sensor array 86 at input 312a and various d.c. reference levels for detecting the presence of holes, through the use of a digital sample and hold circuit and cooperating comparator circuits, as will be more fully described hereinbelow.

The folded corner detection circuit 314 utilizes the system timing pulse signals at input 314b and the signals of sensors 86a through 86d of sensor array 86, as well as reference level signals derived from circuit 336 to detect the presence of folded or missing corners at both the leading and trailing edges of a sheet.

Average density detection and length measuring circuit 316 utilizes the signals from all of the sensors in array 86 at input 316a and the timing pulses at input 316b, as well as a document detected signal, derived from output 312b of hole detection circuit 312, as well as reference level signals derived from circuit 336, to determine the average density over first and second halves of each sheet and to determine whether the sheet being handled is either too long, too short, or neither of the above.

Selection of the operations to be performed and adjustment of the threshold levels in accordance with the particular needs of the operator are accomplished through the keyboard and control board 340 which provides control signals to a group of inputs represented as 302f of central processing unit 302, which signals are derived from the group of lines represented as output 340a. Control signals derived from ports 302g of the central processing unit 302 are coupled through control line group 302h to inputs 340b of the keyboard and control means 340.

A group of output lines 340c are coupled from the operator adjustable controls to be more fully described to reference level circuitry 336, whereupon the sensitivity controls provided as part of the control panel array are utilized to adjust the various reference levels to suit the needs of the particular application.

The central processing unit 302 provides observable information to the operator by means of output lines represented by line group 302m, for application to the inputs 342a of display circuit 342 which, as will be more fully described hereinbelow, is capable of displaying information such as, but not limited to, the number of fit sheets which have been processed; the number of unfit sheets which have been processed; the total number of suspect documents which have been processed; the number of fit and unfit sheets within a batch, when the batching mode is selected; to name just a few of the possible displays. Outputs 302k-1 to 302k-4 reset the evaluating circuits 334, 314, 312 and 316 after sampling the results of their evaluations.

Figure 4:
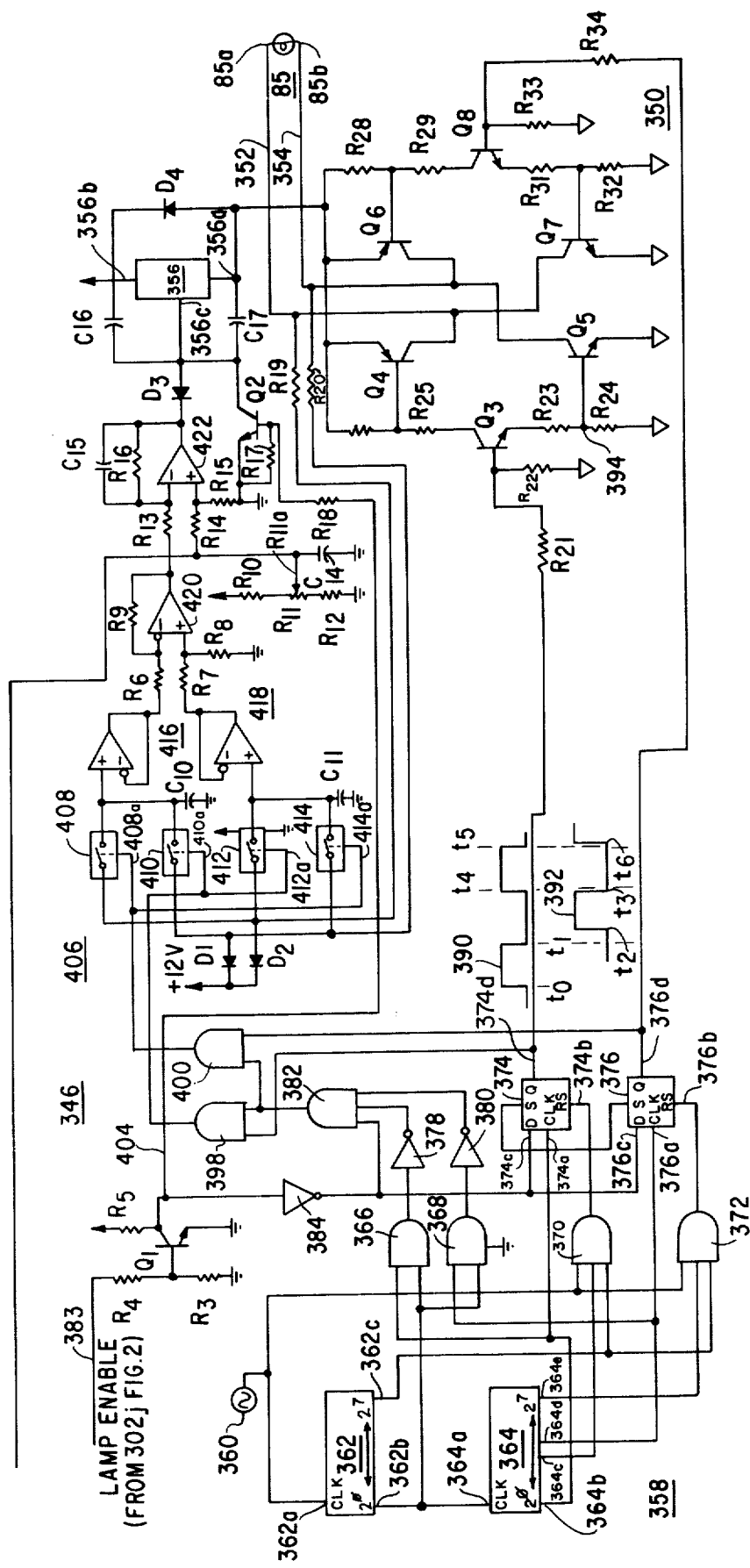
FIG. 4 is a schematic diagram showing the lamp control circuit for regulating the operating voltage provided to the lamp which is employed as part of the sensor circuitry.

FIG. 4 shows a detailed block diagram of the lamp regulating circuitry 346 for regulating the voltage levels of the voltage applied to halogen lamp 85. In order to maximize the useful operating life of halogen lamp 85, the lamp is provided with a d.c. supply voltage which is alternated in a regular, periodic fashion. This is accomplished by the use of an "H-type" circuit 350 comprised of transistors Q4, Q5, Q6 and Q7, only two of said transistors, i.e. either Q6 and Q7 or Q4 and Q5, being conductive at any given time. The switching of transistors Q4 through Q7 is controlled by a pair of switching transistors Q3 and Q8, transistor Q3 having its collector and emitter electrodes respectively coupled to the base electrodes of transistors Q4 and Q5, transistor Q8 having its collector and emitter electrodes respectively coupled to the base electrodes of transistors of Q6 and Q7. The switching circuitry, as will be more fully described, functions so that while terminal 85a of lamp 85 is coupled to ground through transistor Q7, terminal 85b is coupled to a positive d.c. level through line 354 and transistor Q6 to terminal 356a of voltage regulator 356. Alternatively, when terminal 85b of lamp 85 is coupled through line 354, and transistor Q5 to ground, terminal 85a is coupled through line 352 and transistor Q4 to line 356a of voltage regulator 356.

The voltage regulator 356, which may for example be a type u A78H12SC is provided with a voltage at terminal 356b which is of the order of 18 volts. Voltage regulator 356 functions to maintain precisely a 12 volt difference between the voltage level at its control input 356c and its output 356a. For example, if the voltage level at input 356c is at +5 volts, the output level at output terminal 356a will be +17 volts; if the voltage level at 356c is at +4 volts, the voltage level at output 356a will be +16 volts, if the voltage level at input 356c is at −1 volt, the voltage at output 356a is +11 volts, and so forth.

The switching of the "H-type" circuit 350 is performed at a rate to reverse the polarity of the d.c. signal applied across lamp 85 at a frequency in the range from 100 Hz to 1 kHz cycles. The signals are derived from switching circuit 358 as will be more fully described hereinbelow. Due to the fact that the transistors Q4 through Q7 have storage delays, i.e. due to the fact that the transistors Q4 through Q7 are capable of turning on more rapidly than they are capable of turning off, the switching control signals are derived in such a manner as to assure that the transistor of "H-type" circuit to be switched off is switched off early and the transistor which is to be switched on is switched on at a predetermined time interval sufficient to allow the transistor which has just received a switching signal to be fully switched off before the transistor to be turned on is in fact turned on.

The switching control circuit is comprised of a clock source 360 for applying clock pulses to input 362a of an Octal Johnson type counter 362. Output 362b of counter 362 applies output pulses at the same clock rate as clock 360, to the clock input 364a of a second multi-stage binary counter 364. Clock pulses from source 360 are also applied to one input of AND gates 370 and 372.

Output 362b of counter 362 is coupled in common to one input of AND gates 366 and 368. The output 362c of counter 362, which is coupled to the last stage of counter 362, which is preferably an 8-stage counter, is coupled in common to one input of each of the AND gates 370 and 372 and applies pulses to these gates at phase delay relative to output 362b.

Output 364b of counter 364, which is coupled to the first stage of the counter, applies signals to one input of AND gate 366 and the clock input 374a of a D-type bistable flip-flop 374. Output 364c, which is coupled to the fourth stage of counter 364 applies signals to one input of AND gate 370. Output 364d, which is coupled to the fifth stage of counter 364 applies its signal level simultaneously to one input of gate 368 and to the clock input 376a of bistable flip-flop 376. Output 364e of counter 364, which is coupled to the last stage of counter 364, applies its signal level to one input of AND gate 372.

The outputs of gates 370, 372 are coupled to the reset inputs 374b and 376b of bistable flip-flops 374, 376. The outputs of gates 366 and 368 are coupled through inverters 378 and 380 to two inputs of AND gate 382. The remaining input of AND gate 382 is coupled to the collector of transistor Q1 through inverter 384 whose output is also coupled to the D-inputs 374c and 376c of bistable flip-flops 374, 376. Transistor Q1 has its collector and emitter electrodes coupled between positive 12 volts through resistor R5 and ground potential respectively. A lamp enable signal is applied to line 383 when it is desired to illuminate the lamp, causing transistor Q1 to conduct. The level at the collector of Q1 goes low, which condition is inverted at 384 to apply a high level at the D-inputs 374c, 376c of flip-flops 374, 376 and to apply a high level to AND gate 382. In the absence of a lamp enable signal, the collector of Q1 is high, which state is inverted by inverter 384 causing low levels to be applied to AND gate 382 and the D-inputs 374c and 376c, preventing these circuits from operating.

Assuming that a lamp enable signal is present, transistor Q1, through inverter 384 applies a high level to inputs 374c and 376c. Output 364b of counter 364 applies a pulse to the clock pulse input 374a of bistable flip-flop 374, causing its Q output 374d to follow the level applied at input 374c. The leading edge of the pulse 390 is thus initiated at time $t_o$. The pulse is terminated by means of a reset input signal applied to reset input 374b by the output of gate 370 when the output 364c of counter 364 changes, developing the trailing edge at time $t_1$.

The Q output 376d of bistable flip-flop 376 goes high upon receiving a clock pulse from output 364d of counter 364 which occurs at a predetermined time $t_2$ after the trailing edge of pulse 390 goes low. Bistable flip-flop 376 is reset by gate 372 from output 364e of counter 364, the trailing pulse occurring at time $t_3$. The output 374d of bistable flip-flop 374 goes high again at a time $t_4$ after the trailing edge of square pulse 392 occurring at time $t_3$. Time $t_4$ actually coincides with time $t_o$ due to the reinitiated count of counter 364. Output 374d goes low again at time $t_5$ by the reset signal from gate 370 while output 376d of bistable flip-flop 376 goes high at time $t_6$ which is a predetermined time after time $t_5$. These waveforms are applied to the base electrodes of transistors Q3 and Q8 to control switching of the H-type circuit 350. For example, when a high level is applied to the base of Q3, the output at the collector of Q3 drops while the level of the common point 394 between resistors R23 and R24 goes high to turn on transistor Q5. The level at the collector of Q3 turns off transistor Q4. When a low level is applied to the base of Q3, Q3 is turned off causing the level at common point 394 to go to ground and turning transistor Q5 off. The collector of Q3 goes high causing transistor Q4 to be turned on. Switching transistor Q8 controls the operation of transistors Q6 and Q7 in a similar fashion. However, the delay between leading and trailing edges of the pulses as described hereinabove provide sufficient time for transistors being turned off to experience the aforementioned storage delay and be fully turned off before the transistor in series with the lamp is turned on. Thus for example, if transistor Q4 is on and transistor Q7 is off, and the states of these transistors are to be reversed, the application of a turn-on level signal to the base of Q7 is delayed relative to the turn-off level applied to Q4 for a period sufficient to be assured that Q4 is completely turned off.

The outputs of bistable flip-flops 374 and 376, which develop the aforementioned square pulse waveforms, which waveforms have a duty cycle of less than 50% and preferably of the order of 48% (to compensate for the storage delays of transistors Q4–Q7), are also connected to respective inputs of gates 398 and 400, whose remaining inputs are coupled in common to the output of gate 382 which applies an enable signal to gates 398 and 400 during the time intervals that the associated transistors are turned on. The collector of Q1 is coupled through line 404 to the base of Q2 for the purpose of activating regulating circuit 356. The outputs of gates 400 and 398 are respectively coupled to the control inputs 408a–414a of solid state switches 408–414, and control inputs 410a–412a of solid state switches 410–412. Each of these switches respectively couple associated terminals 85a and 85b of lamp 85 to a pair of sample and hold circuits 416 and 418. For example, when terminal 58a is at a +d.c. voltage and terminal 85b is at ground, these voltage levels are applied through line 352 and resistor R19 simultaneously to one input of solid-state switches 408 and 412 and through lead 354 and resistor R20 simultaneously to one input of each of the solid-state switches 410 and 414. Terminal 85a, being at a high level d.c., gate 400 is enabled to close solid state switches 408 and 414, while gate 398 is disabled to open solid state switches 410 and 412. The sample and hold circuits 416 and 418 sample the positive d.c. voltage level and temporarily store this level. The outputs of sample and hold circuits 416 and 418 are coupled to the inverted and non-inverted inputs respectively of an amplifier 420 to develop a difference signal which is applied to the inverting input of comparator 422, where it is compared with a reference voltage level applied to the non-inverting input of comparator 422 by the adjustable arm R11a of potentiometer R11. The difference voltage is applied to control input 356c of voltage regulator 356 only during the presence of a lamp enable signal which is applied to the base of transistor Q2 through line 404 and resistor R18 to turn Q2 off and apply a regulating level to the voltage regulator input 356c. As was described hereinabove, output terminal 356a of series regulator 356 maintains a predetermined precise voltage difference between a level at output 356a and a level at regulator input 356c, in the example being given, 12 volts.

When the polarities of the voltage applied to lamp 85 are reversed, terminal 85b going positive and 85a going to ground, gate 398 closes switches 410, 412 while gate 400 opens switches 408 and 414 to apply the positive voltage level from terminal 85b through solid state switches 410 and 412 to the sample and hold circuits 416 and 418 respectively. The difference between the voltage level and the reference level, measured by comparator 422, is developed at the output of error amplifier 422 in order to appropriately adjust the output level at 356a of series regulator 356. Thus, the polarity of the signal voltage applied to halogen lamp 85 is enabled to be switched at high speed and is further enabled to be constantly regulated so as to control the voltage level within very tight tolerances.

In spite of the fact that the regulation circuit of FIG. 4 provides excellent regulation of halogen lamp 85, other changes may occur in the sensing array due to the aging of components, accumulation of dirt and dust in the region of the optical path between light source 85 and sensor array 86, and the like.

Figure 5:
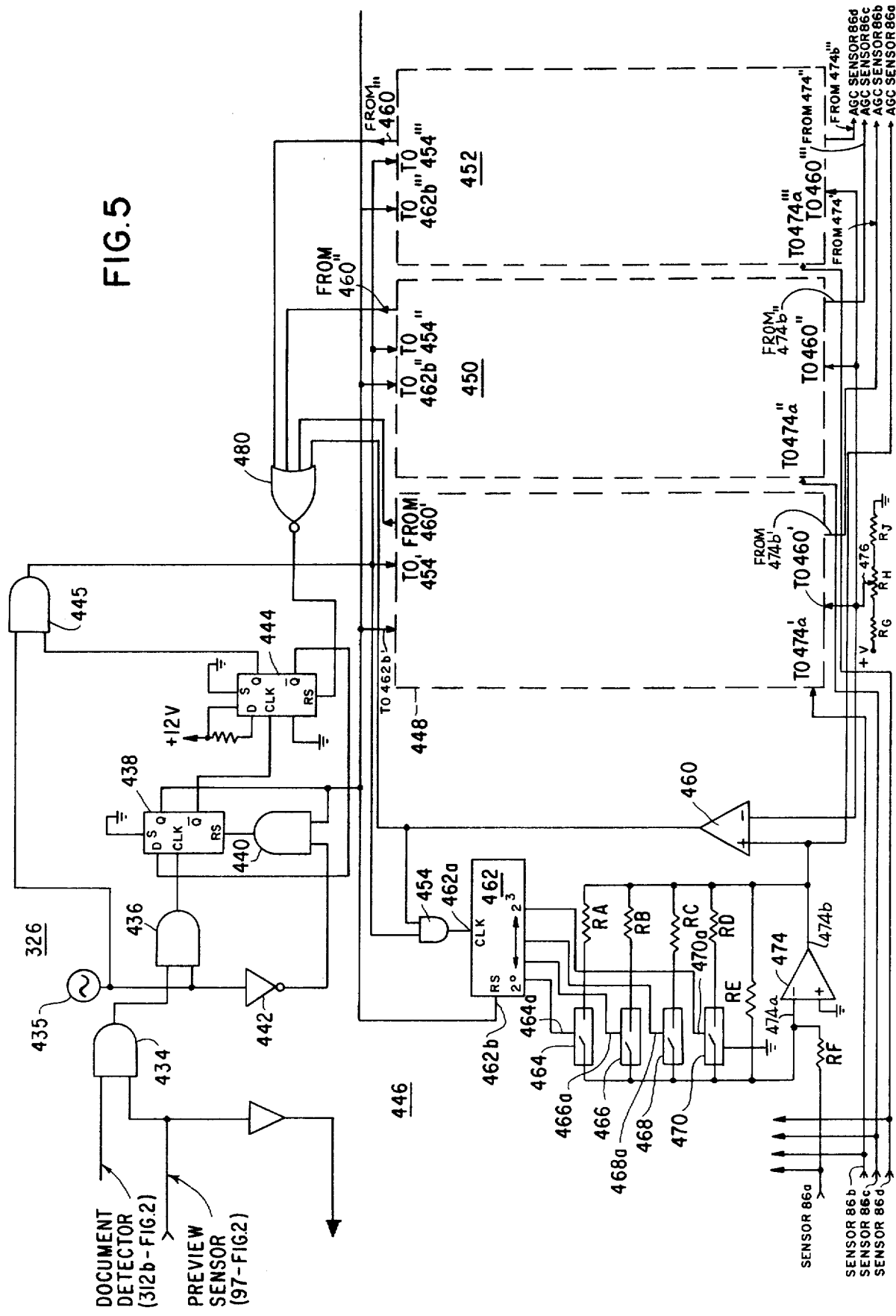
FIG. 5 is a schematic diagram showing the automatic gain control circuit of FIG. 2 in greater detail.

In order to automatically compensate for such changes, be they gradual or abrupt, the sensors in sensor array 86 undergo initial amplification by amplifier circuit 324 and thereafter are coupled to an automatic gain control circuit 326 for automatically and precisely regulating the output level of the sensor signals by comparison with a gain reference voltage applied at input 326e. The automatic gain control circuit 326 is shown in greater detail in FIG. 5 and is comprised of a gate 434 which is enabled when signals from preview sensor 97 and a document detected signal is developed at output 312b of hole detection circuit 312 to enable gate 436 which passes clock pulses to the clock pulse input of a bistable flip-flop 438. The interval during which an automatic gain control adjustment is performed is the time interval measured between the passing of the trailing edge of a document beyond sensor array 86 and the movement of the leading edge of the next document over preview sensor 97. The Q output of bistable flip-flop 438 goes high causing gate 440 to pass one clock pulse from oscillator 435 through inverter 422 to gate 440, resetting the bistable flip-flop. The Q output of bistable flip-flop 438 is also coupled to the reset input 462b of a multi-stage counter 462 which is an integral part of the automatic gain control circuit 446 for sensor 86a. Automatic gain control circuits 448, 450 and 452 have been shown by black boxes simplifying FIG. 5, it being understood that each of the automatic gain control circuits 448 through 452 are identical to automatic gain control circuit 446.

Automatic gain control circuit (hereinafter AGC circuit) 446 also includes gate 454 which is enabled, when the Q output of bistable flip-flop 444 is high, to pass one pulse from clock pulse source 435 through gate 445. The other input of gate 454 is high, so long as the output of comparator 460 has yet to indicate that the gain adjustment compares with the desired reference level. The output of bistable flip-flop 444 goes high upon the switching of bistable flipflop 438 as was described hereinabove. As a result, clock pulses are passed from clock pulse course 435 through gate 445 and 454 to the clock pulse input 462a of multi-stage counter 426. The output of each stage of counter 462 is coupled to the control terminal 464a–470a of an associated solid state switch 464 through 470. Each switch is coupled in a branch circuit with a resistance element $R_A$ through $R_D$. A final resistance element $R_E$ forms a complete branch circuit. The sensor signal of sensor 86a is applied to the inverting input of operational amplifier 474. The output of operational amplifier 474 is fed back to the input through one or more of the branch circuits containing resistors $R_A$ through $R_E$, resistor $R_E$ always being in the feedback circuit.

The clock pulses are applied to clock input 462a and when a reset reference level is removed from reset input 462b, counter 462 starts to count from a zero count toward a maximum count wherein switches 464 through 470 are closed in a predetermined sequence, switch 464 closing, thereafter switch 466 closing as 464 opens, switches 464 and 466 both closing, and so forth. The resistance values of resistors in the branch circuits are weighted in that resistor $R_D$ is double the value of resistor $R_E$, resistor $R_C$ is double the resistance value of resistor $R_D$, and so forth. The output of operational amplifier 474 is a function of the feedback impedance coupled between its output 474b and its input 474a divided by the input resistor $R_F$, whereupon the voltage at the output is regulated by selective coupling of the resistors in the aforementioned branch circuits. The counter 462 is operated in such a manner as to begin at a zero count and count-up in order to decrease the gain from a maximum value at the output of operational amplifier 474, as the count in counter 462 is advanced from a zero count toward the maximum count.

Comparator 460 compares the signal level at the output of operational amplifier 474 with the reference level signal developed across the voltage divider circuit comprised of resistors $R_G$, $R_H$ and $R_J$ and is coupled to comparator 460 through adjustable arm 476. As soon as the voltage level at the output of operational amplifier 474 equals the reference level, the output of comparator 460 goes low to block gate 454 from passing clock pulses from clock pulse source 435 through gates 445 and 454.

This gain control level is maintained until the next time an adjustment is performed, at which time the operation described hereinabove is repeated. Gain control adjustments are made between each interval during the passage of the trailing edge of a document and the passage of the leading edge of the next succeeding document in the region of sensor array 86 and preview sensor 97.

As was mentioned hereinabove, automatic gain control circuits 448 through 452 operate in substantially the identical manner. The output of comparator 460 is also coupled to one input of gate 480 which resets bistable flip-flop 444 to block gate 445 from supplying pulses to each of the counters forming part of their associated automatic gain control circuits. It should be understood that gate 480 resets bistable flip-flop 444 only after all of the reference levels have been adjusted.

Although the automatic gain control circuit 446 shows a 4-stage counter for selectively closing solid state switches 464–470 provided in four associated branch circuits, it should be understood that the total number of branch circuits may be increased or decreased and accordingly that the number of stages of counter 462 may be increased or decreased depending upon the particular accuracy level desired.

Once an adjustment is made, the count in each counter 462 is maintained until at least the next adjustment is made. The outputs of each of the operational amplifiers 460 provided in each automatic gain control circuit are simultaneously applied to associated inputs of the hole detection circuit 312 (see FIGS. 2 & 7), folded corner detection circuit 314 (FIGS. 2 and 8) and average density and length measuring circuit 316 (FIGS. 2 & 9).

A detailed diagram of the hole detection circuit 312 is shown in FIGS. 7a and 7b.

A separate hole detection circuit 490 through 496 is provided for each of the four sensors in sensor array 86. Since the circuits are substantially identical in design and function, only one of the circuits will be described in detail, for purposes of simplicity. To further simplify FIGS. 7a and 7b, hole detection circuits 492 through 496 have been shown in amplified black box form.

The signal of sensor 86a is simultaneously applied to one input of hole comparator 514 and to one input of an amplitude limiter circuit comprised of operational amplifier 498, the remaining input being coupled to the output 536a of an operational amplifier 536 forming part of adjustable amplitude limited adjustment circuit 504. The amplitude limited signal output of amplifier 498 is coupled to terminal 506b of the diode bridge 506 by operational amplifier 500 which is operating as a voltage follower comparator. The signal level applied to terminal 506b is limited in accordance with the adjustment of the amplitude limit adjustment circuit. Comparator 502 operates as an inverter and compares the output of comparator 514 with the output 536a of operational amplifier 536. The increase in light intensity due to the presence of a hole causes comparator 502 to develop an output which, when applied to input 506a, causes the slew rate of the slew rate limiter 506 to be further reduced. Terminal 506c of diode bridge 506 is coupled to one input of operational amplifier 508 which, together with capacitor C1 and bridge circuit 506, forms a slew rate limitor circuit which limits the rate at which the output of operational amplifier 508 can follow a positive going signal, having a very sharp leading edge.

The output of the slew rate limitor circuit 506 is coupled to one input of operational amplifier 510 and to output line 512 for a purpose to be more fully described. Automatic threshold circuit 510 raises the level of the slew rate limiter circuit by a predetermined value, provided by operational amplifier 536 and applies this signal to one input of comparator 514. The other input of comparator 514 is directly coupled to receive the sensor level signal through line 516. The output of comparator 514 is coupled to one input of gate 518 whose remaining inputs are coupled to the output of gate 520 and hole detection inhibit line 521 to permit gate 518 to pass the signal representing a detection of a hole only when the hole detection circuit is not inhibited and when less than all of the hole detection circuits indicate the presence of a hole. When all of the hole detection circuits 490 through 496 detect maximum brightness, this is interpreted as the passage of the trailing edge of a sheet beyond the sensor array 86. Under this condition, gate 520 inhibits all of the gates 518 and 522 through 526. When less than all of the hole detection circuits indicate the presence of maximum brightness, this condition is interpreted as a hole or tear in the sheet enabling all of the gates 518 and 522 through 526 to pass a hole detection signal if one is present.

The outputs of gates 518 through 526 are coupled through inverters 527–533 to the reset inputs 538a of digital sample and hold circuits 528 through 534 respectively. Since all of the digital sample and hold circuits are substantially identical in design and function to one another, digital sample and hold circuits 530 through 534 have been shown in black box form and only a description of digital sample and hold circuit 528 will be given herein for purposes of simplicity.

The signal developed by gate 520 is utilized in detection circuit 316 as will be more fully described and is also utilized by a central processing unit 302 for developing a count of the documents being handled.

Figure 7C:
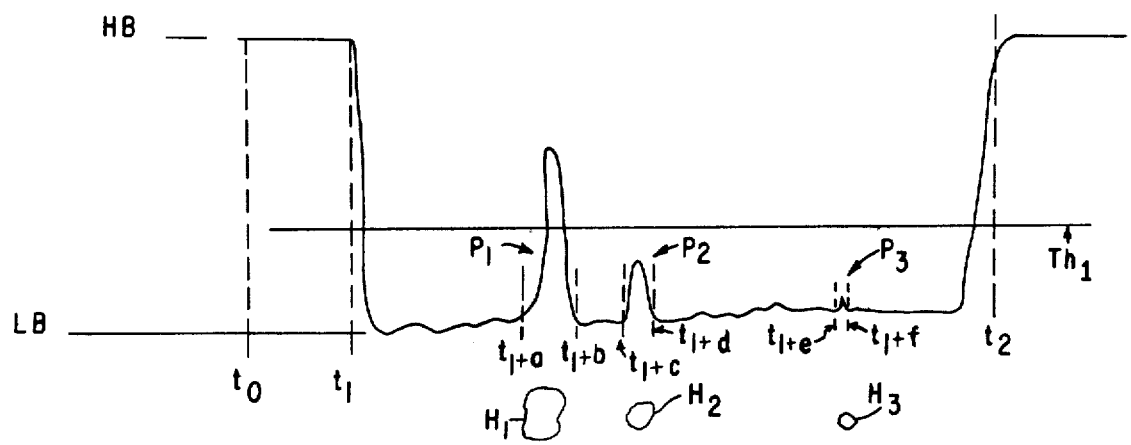
Figure 7D:
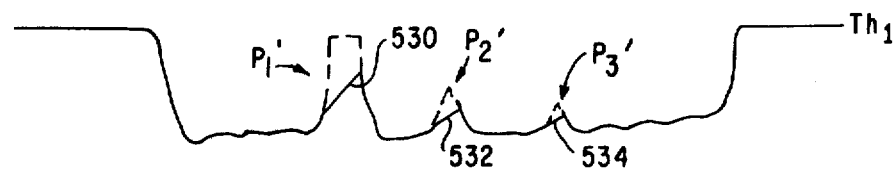

The operation of the hole detector circuit may be better understood from consideration of the waveform diagrams of FIGS. 7c through 7d. FIG. 7c is a waveform diagram showing the signal level developed by a piece of paper currency. At time $t_o$, the output of the sensor is high indicating the absence of a document. At time $t_1$, the leading edge of the document passes over sensor array 86 causing the output level of the associated sensor to drop considerably. The output level remains relatively low until, at time $t_2$, when the trailing of the document passes array 86, the output of the sensor goes to maximum.

Assuming that a fairly large hole is present in the paper document, the sensor level output abruptly goes high at time $t_1+A$, stays high for a period of time and then drops at time $t_1+B$ back to a lower output level. A smaller hole is represented by the pulse occurring during time $t_1+C$ and $t_1+D$, the holes H1 and H2 being shown immediately beneath these pulses. An extremely small hole H3 is represented by the small pulse occurring between time $t_1+E$ and time $t_1+F$.

The signal applied to circuit 490 by sensor 86a is thus represented by the waveform of FIG. 7c.

The amplitude limiter circuit limits the output of the sensor for example, to the threshold level Th1 shown in FIG. 7c, limiting any signal to a maximum of the threshold level. The resulting waveform at the output of the amplitude limiter circuit is thus shown in FIG. 7d.

The slew rate limiter limits the rate at which the signal appearing at the output of operational amplifier 508 can follow the actual signal being developed by sensor 86a. Thus the slew rate limiter cannot follow the rapid change in the leading edge of pulse P1 and builds up at a slower rate to a signal level represented by the sloping portion 530' of altered pulse P1'. The slew rate limiter is, however, able to follow the rapid negative change in the signal, as shown by waveform 7d. The slew rate limiter yields similar results for the pulses P2 and P3, as shown by the sloping portions 532' and 534' of pulses P2' and P3' respectively, shown in FIG. 7d.

Figure 7E:
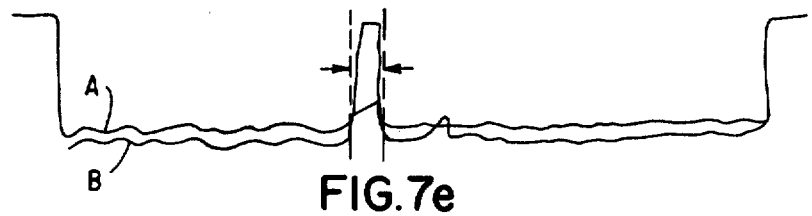
Figure 7F:
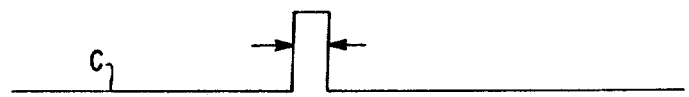

Considering the waveform A of FIG. 7e, the waveform of 7c, after undergoing slew rate limiting, has its d.c. level adjusted upwardly and thereafter applied to one input of comparator 514. The other input of comparator 514 receives the original sensor signal applied at input 490a and represented by waveform B shown in FIG. 7e. As can clearly be seen, waveform A is at a higher level than waveform B over most of the period during which a document is passing over the sensor array. However, waveform B can be seen to exceed waveform A in instantaneous signal level at time $t_x$, which results from the inability of the output of the slew rate limiter circuit to follow abrupt positive going changes. When waveform B exceeds waveform A, comparator 514 develops a hole detected signal which is passed by gate 518. This signal remains high, as represented by the pulse of FIG. 7f, until the instantaneous level of waveform B drops below the instantaneous level of waveform A, the duration of the pulse shown by the waveform of FIG. 7e representing the length of the hole or opening in the document measured in the feed direction.

The pulse passed by gate 518 is applied to the reset input 538a of multistage counter 538 which forms part of the digital sample and hold circuit 528. In the absence of a reset input signal, the timing pulses, developed by sensor 120 (see FIG. 2) which are coupled to clock input 538b of counter 538, are passed to allow counter 538 to count up from a zero count toward a maximum count. Each output stage of counter 538 has its output line 538c through 538g coupled in a branch circuit having a branch circuit resistor R1 through R5 respectively. All of the resistors R1 through R5 are coupled to a common terminal 542, which is coupled to a +12 volt source through resistor R6 and to one input of an operational amplifier 544. Each of the branch circuits contain resistors R1 through R5 which have weighted resistance values, wherein the value of resistance R2 is one half that of R1, the value of resistance R3 is one half that of R2, and so forth. The amount of current each of these resistances delivers to one input of comparator 544 continually increases depending upon the number of resistances in the circuit. As the count in counter of 538 is incremented, the voltage level of output terminal of operational amplifier 544 drops from a maximum value is a staircase fashion, as represented by the descending staircase waveform shown in FIG. 7b and in FIG. 7g. The level at the output of operational amplifier 544 follows the level at input 542. The staircase waveform is applied to one input of comparator 546 whose remaining input is coupled to the voltage divider circuit comprised of potentiometer 547 having adjustable switch arm 547a which is manipulated by means of a control knob provided on the control panel of FIG. 11, as will be more fully described hereinbelow.

Figure 7G:
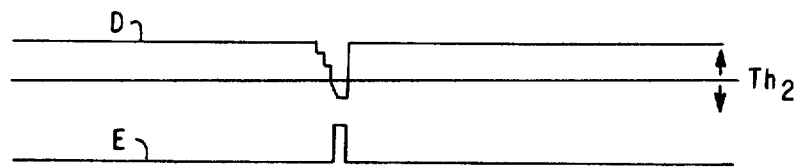

As soon as the level of the staircase signal drops below the threshold level applied to the noninverting input of comparator 546, which threshold level Th2 is shown in FIG. 7g, comparator 546 generates a pulse as shown by waveform E of FIG. 7g. This pulse is applied to the clock input 548a of D-type bistable flip-flop 548 whose D input 548b is maintained at a high level. The Q output 548c follows the level at the D input 548b upon receipt of the aforesaid clock pulse as shown by waveform E of FIG. 7g. The bistable flip-flop 548 temporarily stores the hole condition detected for purposes of "remembering" the hole condition until such time that the central processing unit 302 is free to examine the state of the bistable flip-flop 548, which occurs at a particular time during a sample routine performed by the central processing unit 302. Similar bistable flip-flops 548'-548''' are provided for each of the other sensor units. Adjustment of the threshold level applied to comparator 546 allows extremely small holes to be ignored, if desired. Alternatively, the adjustment may be made quite sensitive to detect even small holes. The sensitivity of the system is designed to detect holes, tears, perforations and the like having a dimension of the order of 0.04 inches, or less, measured in the sheet feed direction.

Gate 552 shown in FIG. 7a derives signals from all of the hole detection circuits 490 through 496 to provide a signal indicating the presence of a hole by at least one of the sensors, regardless of the size of the document hole, which information is made available to the density circuit 316 (FIG. 9) for processing in a manner to be more fully described.

The average density detection and length measuring circuit 316 is shown in FIG. 9. The signals from all of the sensors 86a through 86d are summed by operational amplifier 570. The output of operational amplifier 570 is simultaneously applied to the noninverting input of comparator 572 and the inverting input of comparator 574. The signal level is compared against the "light" reference threshold represented by an internally adjustable potentiometer 576 having adjustable arm 576a. The signal level is also compared against a "dark" reference threshold represented by internally adjustable potentiometer 578 having adjustable arm 578a. The output of comparator 572 is applied to one input of AND gate 580. The remaining input of AND gate 580 receives the document hole signal at the output of gate 552, shown in FIG. 7a, in order to prevent the presence of a document hole from being interpreted as a document having density lighter than the light density threshold. The output of comparator 574 is applied to one input of gate 582, the remaining input being coupled to the output of gate 580. The output of gate 582 is applied to one input of gate 584, whose remaining input receives double frequency timing pulses from the timing source, said timing source being coupled to the input of frequency doubler 586 whose output is coupled to the remaining input of gate 584. Thus, when the density of the document is either lighter than the light threshold or darker than the dark threshold, double frequency timing pulses are applied through gate 584 to gate 588, whose remaining input is coupled to the output 590e of bistable flip-flop 590, to be more fully described, for the purpose of inhibiting the application of timing pulses to the counter 594 when the marginal portions of the leading and trailing edges of the sheet being examined are passing the sensor array 86.

Comparators 650 and 664 provide density detection inhibit signals to inhibit density signals when the marginal portions of the leading and trailing edges of a sheet are passing the sensors. The descending staircase voltage signal developed at the output 660a of operational amplifier 660 due to the count being developed by counter 618, is applied to the inverting input of comparator 650 for comparison against a threshold level applied to the non-inverting input of comparator 650 by resistor R37. As the leading edge of a sheet moves over sensor array 86, maximum staircase voltage is applied to comparator 650. The staircase voltage drops as the leading edge of the sheet moves past the sensor array and a comparison occurs when the marginal portion of the leading edge has passed the sensor array 86. The change in output level of comparator 650 is coupled through gate 668 to the reset input 590a of bistable flip-flop 590. The output level of gate 668 changes when the output level of comparator 650 changes relative to the level of the document detected signal applied to the remaining input of gate 668, causing output 590e of flip-flop to change, thereby removing a level which blocked gate 588 from passing double frequency timing pulses from frequency doubler 586, enabling counter 594 to accumulate timing pulses whenever a "too light" or "too dark" condition is present for an area of the sheet beyond the leading marginal portion.

Counter 594 is reset at the leading and trailing edge of each sheet and at the mid-length point of each sheet by comparator 598, a timing circuit 671 comprised of resistor $R_{T1}$ and capacitor $C_{T1}$ and Exclusive-OR gate 669.

When a leading edge of a sheet passes sensor array 86, counter 618 is reset, causing the output level of comparator 598 to change. This level is applied to timing circuit 671 and one input of gate 669. Timing circuit 671 delays the signal level transition applied to the remaining input of gate 669, which develops a pulse whose pulse width is determined by the delay of timing circuit 671. Counter 594 is thus reset in readiness for receipt of timing pulses when gate 588 is enabled.

When the staircase signal reduces to a level equal to the reference level applied to comparator 598 by resistor R38, indicating the mid-length point of a sheet passing over sensor array 86, the output level of comparator 598 shifts, causing timing circuit 671 and gate 669 to apply a pulse to reset input 594b, resetting the counter 594 in readiness for a density measurement for the last half of the sheet.

Presuming that the aforesaid marginal portion has now passed through the sensor array 86, the reset level is removed and double frequency clock pulses are applied to the clock input 594a whenever a too light or too dark condition is detected, causing counter 594 to step from a zero count towards a maximum count. The outputs of counter 594 are each coupled into a branch circuit having a resistor R10 through R15 wherein the resistors are weighted so that the resistance value of R11 is one half the resistance value of R10, R12 is one half the value of R11, and so forth. All of the resistors have their opposite ends coupled in common to a 12-volt source through a resistor R16. The values of R10–R15 are chosen so that the parallel combination of resistors R10–R15 is substantially equal to R16. The common terminal between resistors R10 through R15 and R16 is coupled to the inverting input of operational amplifier 596 whose output is coupled to the inverting input of comparator 600 whose noninverting input is coupled to the density sensitivity potentiometer 602. Adjustable arm 602a is coupled to the non-inverting input of comparator 600 and is adjustable at the front control panel, to be more fully described in connection with FIG. 11. When the staircase signal developed by counter 594 and resistors R10 through R16 reaches a predetermined threshold, the output of comparator 600 applies a signal simultaneously to one input of gates 604 and 606. Gate 604 is enabled by the Q output of D-type flip-flop 610 which is clocked by comparator 598.

The output of comparator 598 is applied to the D input 610a of flip-flop 610, directly to one input of Exclusive-OR gate 667 and to the other input of gate 667 through the delay circuit 673 comprised of resistor $R_{T2}$ and capacitor $C_{T2}$. Delay circuit 673 and gate 667 function in a manner similar to gate 669 and delay circuit 671 and cooperate with inverter 675, causing $\overline{Q}$ output 610c to enable gate 604 during the time that the first half of a sheet is being examined and thereafter causing Q output 610d to enable gate 606 during the time that the last half of a sheet is being examined. If the count accumulated by counter 594 is sufficient to cause the staircase voltage level to drop below the threshold established by potentiometer 602, the dense condition is clocked into the appropriate flip-flop 612 or 682.

The outputs of gates 604 and 606 are respectively coupled to the clock inputs 612a, 682a of D-type bistable flip-flops 612, 682 for storing a density condition until such time that the central processor 302 interrogates the average density detection circuitry.

The document detected signal developed by the hole detection circuitry 312 of FIGS. 7a and 7b is utilized to measure document length and appears at input 614. The document detected signal is simultaneously applied to the reset inputs 616b and 618b of digital counters 616 and 616. The timing pulses are divided by bistable flip-flop 620 and applied to clock input 616a of digital counter 616, and are applied directly without division to the clock input 618a of digital counter 618. Counters 616 and 618 and their associated resistor circuits operate in much the same way as counter 594 and its associated resistor circuit.

The outputs of each binary stage of digital counter 616 are coupled to branch circuits each containing a resistor R17 through R23 whose opposite ends are connected in common to the inverting input of operational amplifier 624 and to the +12-volt source through resistor R24. As the counter 616 counts up from a zero count, a negative going staircase signal is developed by operational amplifier 624. This level is compared against a reference level derived from reference level circuit 630, comprised of a series circuit including fixed resistors R25 and R26 and internally adjustable potentiometers 632 and 634 having adjustable arms 632a and 634a which are preferably factory adjusted to set the shortest length of an acceptable document and the longest length of an acceptable document. The inputs of operational amplifiers 638 and 640 are coupled to adjustable arms 623a and 634a and their outputs coupled across end terminals of a potentiometer 642 whose adjustable arm 642a is coupled to the noninverting input of comparator 644 through fixed resistor R27a. Arm 642a is also connected to the noninverting input of comparator 648 and across the series connected resistors R37, R38 and R39. The common terminal between resistors R37 and R38 is coupled to the noninverting input of comparator 650, while the common terminal between resistors R38 and R39 is coupled to the inverting input of comparator 598.

The output of operational amplifier 644 is coupled through line 654 to the clock input of a bistable flip-flop 656.

The counter 618 has one output of each of its counter stages coupled to resistors R28 through R34 which are connected in common to the inverting input of operational amplifier 660, whose output is coupled to the inverting inputs of comparators 648, 650 and 664 and to the noninverting input of comparator 598. The output of comparator 648 is coupled to the clock input of bistable flip-flop 666. The output of comparator 598 is coupled to: one input of logical gates 667 and 669; delay circuits 671 and 673; and the D input 610a of flip-flop 610. The output of gate 668 is coupled to the clock input 610b of bistable flip-flop 610. The output of comparator 664 is further coupled to the clock input 590c of bistable flip-flop 590.

Bistable flip-flop 612 has its D input 612b coupled to the $\overline{Q}$ output 610c of bistable flip-flop 610 whose D input 610a is coupled to the output of operational amplifier 598 as was described above. The clock input 612a of bistable flip-flop 612 is coupled to the output of gate 604 whose inputs are respectively coupled to the $\overline{Q}$ output 610c of bistable flip-flop 610, and to the output of comparator 600. The reset input 612c of bistable flip-flop 612 as well the reset inputs of bistable flip-flops 682, 684, 656 and 666 are coupled to line 686 which receives an average data clear signal from the central processing unit 302 shown in FIG. 3.

The D input of bistable flip-flop 682 is coupled to the Q output of flip-flop 610. The clock input of flip-flop 682 is coupled to the output of gate 606, whose inputs are coupled to the Q output 610d of flip-flop 610 and the output of comparator 600. Delay circuits 671 and 673 are designed to cause counter 594 to be reset before bistable 610 is reset.

The operation of the average density and length measurement circuitry is as follows:

With respect to the density measuring circuit, the outputs of sensors 86a through 86d are summed, and applied to the noninverting input of operational amplifier 572, whose output is coupled to the inverting input of comparator 572 and the inverting input of comparator 574. Light and dark reference levels are applied to the inverting input of comparator 572 and the noninverting input of the comparator 574, respectively. In the event that the dark reference threshold is achieved, comparator 574 alters its output level, enabling gate 584 to pass timing pulses on line 697 to apply clocking pulses to counter 594 when gate 588 is enabled by flip-flop 598 when the marginal portion of the leading edge of a sheet has passed the sensor array 86. A reset level signal is applied to counter 594 when the leading edge of a sheet has passed sensor array 86 to reset counter 594 in readiness to accumulate clock pulses. As each stage of the counter 594 is enabled, a descending staircase voltage is developed at the output of operational amplifier 596. This negative going staircase voltage appearing at the output of operational amplifier 596 is applied to the inverting input of comparator 600. As soon as the signal level at the inverting input of comparator 600 drops below the reference level applied to the noninverting input of comparator 600, gates 604 and 606 are enabled. Gate 606 is the only gate able to pass a level to bistable flip-flop 682 during the last half of the examination of a sheet. The reversal of state of the bistable flip-flop 610, whose Q output 610c is coupled to gate 604 and whose $\overline{Q}$ output 610d is coupled to gate 606 alternately enables only one of these two gates. When a signal indicating that the sheet being examined is too dense (or too light) during the first half of a sheet, this condition is stored in bistable flip-flop 612 preparatory to subsequent sampling by the central processing unit 302. Bistable flip-flop 682 stores the same condition when present during the second half of examination of a sheet.

The document length measuring circuitry is initiated upon the occurrence of a document detected signal from gate 520 of FIG. 7a, at which time a reset signal is applied to reset input 618b of counter 618 and to reset input 616b of counter 616, resetting these counters to zero. Clock pulses from the divide-by-two clock pulse source and appearing on line 710, are applied to clock input 618a of counter 618. Bistable flip-flop 620 divides the already divided by two clock pulses on line 710 before applying pulses to the clock pulse input 616a of counter 616.

Clock pulses are accumulated by counter 618, whose output stages are selectively connected by resistors R28 through R34 to the inverting input of operational amplifier 660 which applies a descending staircase signal to the inverting inputs of comparators 648, 650 and 664 and to the noninverting input of comparator 598. The counter 616 cooperates with resistors R17 through R23 and resistor R24, to develop a descending staircase signal which appears at the output of operational amplifier 624. The Q output of bistable 666 is normally high. If the sheet is the proper length, the descending staircase signal of operational amplifier 660 drops below the threshold level applied to comparator 648 by resistor R41, and bistable flip-flop 666 is triggered by a clock pulse to remove the length short condition. When the descending staircase developed by operational amplifier 660 drops below another threshold level coupled thereto by resistor R38, comparator 598 retriggers reset input 594b of counter 594 and causes reversal of the Q and $\overline{Q}$ outputs of bistable flip-flop 610, indicating that one half of a sheet has been examined and examination of the second half of the sheet should now be initiated.

When the descending staircase at the output of comparator 660 falls below a third threshold level provided by operational amplifier 667, and resistors R37–R40 to comparator 664, comparator 664 clocks bistable flip-flop 590 to provide a density detection inhibit signal at output 590e to inhibit the accumulation of timing pulses in counter 594 during the time that the marginal portion of the trailing edge of a sheet is passing sensor array 86. Density measurement is inhibited at this time due to the high transmissivity of the marginal portions of the sheet.

Counter 616 is utilized to develop a signal indicative of the fact that the sheets being examined are too long. The descending staircase signal is developed by operational amplifier 624 and applied to the inverting input of comparator 644 where it is compared against the reference level applied to the noninverting input. Comparator 644 applies a trigger signal to the clock pulse input of bistable flip-flop 656 through line 654 when a document of too great a length is measured, this condition being temporarily stored in bistable flip-flop 656 for subsequent sampling by the central processing unit 302.

Bistable flip-flop 684 develops a data valid condition and its Q output when a document detected signal is terminated. The microprocessor 800 examines the state of bistable 684 and is assured that all conditions in bistables 612, 682, 656 and 666 are valid since the sheet has passed the sensor array 86, i.e., has left the system optics 86.

The central processing unit 302 samples the results of the document length and average density measurement circuitry and upon transfer of said information to the central processing unit 302, applies an average data clear signal to the reset inputs of bistable flip-flops 612, 682, 684, 656 and 666 in readiness for subsequent operation.

The limpness detector circuitry 332 shown as a black box in FIG. 2 is shown in detailed block diagram form in FIG. 6 and is comprised of automatic zero interval timer 902 which derives timing pulses from source 118 (FIG. 2) at input line 902a and the aforementioned document detected signal at input line 902b. The automatic zero interval timer 902 provides an interval during which an offset adjustment can be made.

When the trailing edge of a sheet passes the sensing means 86 (FIG. 2), the signal generated causes timer 902 to begin accumulating pulses. When the timer reaches a first count, which represents the quotient of the length of the path between sensors 86 and limpness detector 142 and the speed of movement of the sheets, a gap interval, during which no sheets are moving between the rollers of the limpness detector 142, is initiated. When the interval timer 902 reaches a second count, representing the end of a gap, the zero interval is terminated. This interval is utilized to make an offset adjustment only when no sheets are present in the limpness detector 142, i.e. during the time interval when the trailing edges of the last sheet has passed through the limpness detector apparatus 142 and before the leading edge of the next sheet enters into the limpness detector. The pulses representing the beginning and the end of the interval are supplied to automatic zero correction circuit 904. The hall-effect sensor 330, whose output is a function of the displacement between the cooperating gear-like rollers of limpness detector 142, applies its output to the input of preamplifier 908, whose output is simultaneously coupled to the inverting input of difference amplifier 910 and to input 904b of automatic zero correction circuit 904. The sensor 330 may be subject to some drift, for example, due to aging.

Automatic zero correction circuit 904 determines the offset adjustment to compensate for the drift of sensor 330 by averaging the output of sensor 330 and storing this value to provide a d.c. offset voltage for the output of amplifier 908 and its output 904c, which is applied to the noninverting input of difference amplifier 910.

The output of difference amplifier 910, which reduces the output of sensor 330 by the d.c. offset voltage present at the output 904c is coupled through amplifier 912 simultaneously to one input of comparator 914, the input 916a of synchronous average processor 916 and leading edge overshoot compensation circuit 918.

The analog signal appearing at the output of amplifier 912 is compared against the voltage reference 915 by comparator 914 to generate a document detected signal when the analog signal is greater than the voltage reference to indicate that a sheet is passing through the limpness detector apparatus, developing the square pulse signal 920 which persists during the time that the sheet passes through the limpness detector apparatus 142.

Synchronous average processor 916 is enabled, upon the presence of a document detected signal at its input 916c and measures the average value of the limpness waveform, which may vary over the length of the sheet, said average value being totally independent of feed speed. When the value of the limpness analog signal appearing at input 916a is above a predetermined threshold, the processor 916 is enabled to accumulate each timing pulse applied at input 916b. The processor 916 may comprise a counter and an analog to digital converter which circuits may be of the type shown as the counter 616 and cooperating staircase generator comprised of resistors R17–R24 and operational amplifier 624 shown in FIG. 9. The average value count is converted into analog form at output 916d which is simultaneously applied to respective inputs of comparators 922 and 924 which compare the limpness value against voltage reference levels applied to the remaining inputs of comparators 922 and 924. In the event that the limpness value is less than the lower reference level, comparator 922 applies a pulse to the clock input 928a of D-type flip-flop 928 which stores an indication that the sheet presently being examined is too limp.

Comparator 924 compares the average of the signal developed at the output 916d against an upper threshold level. When the average value of the limpness signal exceeds the upper threshold level, comparator 924 applies a pulse to the clock input 930a of D-type flip-flop 930, storing an indication that the sheet just examined is too stiff.

As was mentioned hereinabove, the limpness analog signal appearing at the output of amplifier 912 is applied to leading edge overshoot compensation circuit 918 which attenuates the limpness analog signal by a predetermined amount to compensate for the abrupt displacement experienced by the hall-effect sensor 330 relative to the permanent magnet member 328 (see FIG. 2), during the time that the leading edge of a sheet enters the limpness detector. The compensation circuit 918 comprises an R-C circuit which is coupled between amplifier 912 and detectors 936 and 938 when the leading edge of a sheet enters the limpness detector and from 5 to 15 milliseconds thereafter, to attenuate the signal developed by sensor 330, which experiences an abrupt change as the sheet first enters the limpness detector.

The compensated limpness analog signal is simultaneously applied to positive peak detector circuit 936, negative peak detector circuit 938 and one input of each of the comparators 940 and 942.

The output of positive peak detector 936 is compared against the limpness analog signal by differential amplifier 940 to develop a difference value. The negative peak detector circuit 938 develops a negative peak value which is compared against the limpness analog signal by differential amplifier 942. The outputs of differential amplifiers 940 and 942 are applied to respective inputs of comparators 944 and 946 where they are compared against reference threshold levels. Comparator 944 detects extremely stiff conditions, such as, for example, the presence of tape, folds in the sheet, a staple, and so forth. Comparator 946 detects the presence of a localized condition of extreme limpness, such as a severe crease. The outputs of comparators 944, 946, when said threshold levels are reached, apply trigger signals to clock inputs 932a and 934a respectively of the D-type flip-flops 932 and 934 for the purpose of storing the observed conditions for subsequent sampling and evaluation by the central processing unit 302. When these conditions have been sampled by the central processing unit, reset signals are applied at inputs 952 and 954 to reset the storage flip-flops 926 through 934 and the peak detectors 936 and 938.

The operations performed by the circuitry 332 of FIG. 6 may be performed by CPU 302 as follows: (see FIGS. 6a and 6b) The output of sensor 330 is sampled at regular intervals by a sample and hold circuit, converted into digital form and stored in memory. Each sampled quantity is compared against a first stored level to determine the presence of a localized stiffness condition such as a fold or a staple or a piece of tape. Each sampled quantity is compared against a stored level to determine a localized limp condition such as a crease. The stored values are summed and divided by the number of samples to develop an average limpness value which is compared against third and fourth stored values to determine if the sheet is too stiff, too limp or within a fit range between the two values.

FIG. 8 shows a detailed circuit diagram of the folded/missing corner detection circuit 314 shown in simplified black box form in FIG. 2.

The outputs from sensors 86a through 86d are respectively coupled to a group of Exclusive-OR gates 960 through 968. For example, the hole detection signals for sensors "1" (86a) and "3" (86c) are applied to respective inputs of Exclusive-OR gate 960. All signals for sensors "3" (86c) and "2" (86b) are applied to Exclusive-OR gate 962 while sensors "2" (86b) and "4" (86d) are applied to Exclusive-OR gate 964. The outputs of Exclusive-OR gates 960 and 964 are coupled to inputs of Exclusive-OR gates 966 and 968 respectively while the output of Exclusive-OR gate 962 is coupled in common to the remaining inputs of Exclusive-OR gates 966, 968.

Exclusive-OR gate 960 develops a signal at its output if only sensor "1" or only sensor "3" signal is present, which indicates the absence of a sheet, whereas no output is developed if both of said signals are present. Exclusive-OR gates 962 and 964 operate in a similar manner. Thus, Exclusive-OR gate 966 develops an output only in the event that sensor "1" indicates the presence of a hole. Similarly, Exclusive-OR gate 968 develops an output in the event that only sensor "4" indicates the presence of a hole.

The outputs of Exclusive-OR gates 966 and 968 are coupled through inverters 970 and 972, respectively, to reset inputs 974a, 976a of counters 974 and 976 and reset inputs 978a, 980a of counters 978 and 980.

When a document detected signal is present at input line 982, this condition is applied to the reset input 992a of D-type flip-flop 992 and, after inversion by inverter 984, to the clock input 990a of D-type flip-flop 990.

A length ramp signal applied to input 994, derived from output 660a of density circuit 316 shown in FIG. 9, is applied to the inverting input of comparator 660 and to the inverting input of comparator 988. Reference level signals taken from the common terminals between resistors $R_A$ and $R_B$ and between resistors $R_B$ and $R_C$ are applied to the non-inverting inputs of comparators 986 and 988 as shown. The voltage value at the remaining terminal resistor $R_c$ is adjustable by a document length potentiometer which was described hereinabove, and is derived from potentiometer adjustable arm 642a shown in FIG. 9.

So long as the ramp signal is less than a predetermined threshold level, comparator 986 does not apply a reset signal to bistable flip-flop 990 causing its $\overline{Q}$ output 990c to apply a level to the clear entry inputs 974b and 978b of counters 974 and 978. The output of comparator 986 reverses when the end of a document has been reached. However, as soon as the leading edge of the document has been detected, the document detected signal 982 is coupled through inverter 984 to cause bistable flip-flop 990 to set its $\overline{Q}$ output 990c low, removing a clear entry condition from clear entry inputs 974b and 978b of counters 974 and 978. When a folded or missing corner condition is detected by sensor "1", the output level of inverter 970 which retains reset inputs 974a and 976a at the reset state, is removed, allowing counters 974, 976 to accumulate timing pulses appearing at input line 998, which timing pulses are applied to clock inputs 974c and 976c. As soon as counter 974 reaches a predetermined count, indicating that the "hole" condition has persisted for a total of seven counts (in the example given herein), output 974d applies a pulse to the clock input 1000a of D-type flip-flop 1000 to set a binary state in bistable flip-flop 1000 indicative of a leading edge fold in the corner of the sheet associated with the location of sensor "1."

The comparator 988 develops a signal applied to the clock input 992b of D-type flip-flop 992 when the length ramp signal exceeds a predetermined threshold level to remove a clear entry signal level at the clear entry input 976b of counter 976, allowing the presence of a hole signal developed by sensor "1" to remove the reset condition from reset input 976a enabling timing pulses applied at clock input 976c to be accumulated by counter 976. When counter 976 reaches a predetermined count, its output 976d applies a pulse to the clock input of bistable flip-flop 102 causing a signal indicating the presence of a trailing edge folded or missing corner.

Counters 978 and 980 are controlled by Exclusive-OR gate 968 and act to store leading and trailing edge fold signals in bistable flip-flops 1004 and 1006 in a manner substantially identical to that described hereinabove in connection with the operation of counters 974, 976.

FIG. 11 shows the control panel for operating the document handling apparatus and is comprised of three 3-digit numeric displays 720, 722 and 724, which are of the segmented type. A 7-digit display 726 is operated in a multiplexed fashion as will be more fully described to display predetermined information. Reference levels for the hole size, average document density, document length and relative limpness of documents, are adjustable by manipulation of the adjustable control knobs 728, 730, 732 and 734 respectively.

The document handling apparatus is capable of providing a batch having a number of sheets which have been acceptable and/or a number of sheets which have been rejected, by setting the thumb wheel rotary switch elements 736a through 736c of the adjustable thumb wheel switch assemblies 736. In order to select the size of a batch, the thumb wheels are set and the set push button 738 is depressed, to set the batch size of acceptable documents. The batch size of rejected documents may also be set by setting thumb wheel switches 736a through 736c and depressing set push button 740. Three-position switch 742 controls the displays 720 and 722 to display the totals for all fit and unfit sheets which have been handled or for fit and unfit sheets handled since the last completed batch, and the stored batch quantities which were selected.

The total number of sheets set into the machine is displayed by 3-digit display means 724.

The operating mode of the document handling apparatus is selected by manipulation of the mode switches 744, 746, 748 and 750. Two-position mode switch 744 enables the selection of either a sort mode or a count mode. Two-position switch 746 enables the verification mode to be enabled or disabled. Two-position switch 748 enables the folded corner test equipment to be enabled or disabled. Two-position switch 750 enables the counterfeit detecting apparatus (CDA) to be selectively energized or deenergized.

The verify operation is initiated by operating switch 746 to the "ON" position. The thumbwheels 736 are set to the known quantity of sheets placed upon the infeed plate 22 (FIG. 1a). If the count displayed at 724 (FIG. 11) differs from the count set by the thumbwheels 736, display 726 flashes. The count in the register associated with display 724 is transferred to the grand total register associated with display 726. Alternatively, by operating recount button 756, the contents of the registers associated with displays 720, 722, 724 are cleared without transfer of their contents to the registers associated with display 726.

Three-position switch 752 determines which of the three possible accumulated counts are displayed within the 7-digit display assembly 726. The accept position causes a display of a total of all sheets examined by the document handling apparatus which have been found to be acceptable. The reject position causes the display of the total number of sheets examined by the document handling apparatus and which failed to meet the particular criteria for the test or tests being performed. The input position of switch 752 causes the grand total of all sheets examined by the document handling apparatus to be displayed.

The push button switch array comprised of push button switches 754 through 764 provide for operations to be more fully described. An on/off power switch 766 enables selection or deselection of the equipment. Push button 754, briefly, provides for runout of sheets to the unfit output stacker without being counted. Push button 760 resets all registers in the machine, including grand totals, in readiness for operation.

The electronics for the four display arrays 720, 722, 724 and 726 are shown in FIG. 10. The display arrays 720 and 722 are coupled to the central processing unit 302 by means of interface circuitry 770 receiving data from the central processing unit at its input lines ID0 through ID7. A read/write (WR) line is coupled to the central processing unit 302 for selecting or deselecting the displays. A mode (MODE) line selects which of the displays are to receive data from the data lines of the central processing unit 302. Display 724 is coupled to the central processing unit through interface circuit 772 and the 7-digit display unit 726 is coupled to the central processing unit through interface circuit 774.

The central processing unit 302, during a write phase, applies a signal to the WR line and applies data to the data bus lines D0 through D7. As can be seen, these data bus lines are simultaneously coupled to the input data lines ID0 through ID7 of all three interface circuits 770 through 774. To select only one of these interface circuits, the central processing unit 302 puts out signals on its $2^0$ and $2^1$ lines, causing decoder 778 to select only one of the interface circuits 770 through 774 depending upon the two-bit code applied to its inputs 778a and 778b.

Data output lines D1, D2 and D3 apply enabling signals to segmented display elements 720a, 720b and 720c respectively. Lines D5, D6, and D7 apply enabling signals to segmented display elements 722a, 722b and 722c respectively. The display segments for all six display elements receive their enabling signals from the a through g outputs of interface circuit 770. The operation of the segmented display 720 is as follows:

The digit to be displayed by display element 720a, for example, is controlled by the enabling signal supplied at outputs a through g. Simultaneously therewith an enabling signal is applied from line D1 to the enable input of this element. Immediately thereafter, the enabling signals for the segments of the character to be displayed at segmented display position 720b appear at the output terminals a through g and the enabling signal for this display position appears at the output D2. A similar operation occurs for the third digit position 720c. Thereafter, these operations are repeated in successive fashion wherein the refresh rate for the displays is sufficiently rapid to create a display which, to the human eye, appears to be constant, i.e. not blinking or flickering. The displays 722, 724 and 726 function in the identical manner.

The LEDs 782a through 782h of array 782 and 784a through 784e of LED array 784 are utilized for the purpose of identifying the nature of the condition or conditions which have occurred. For example, 782a is lit when the first half of a sheet is too dense; 782b indicates that the second half of a sheet is too dense, 782c indicates that a sheet is too long, 782d indicates that a sheet is too short, etc.

FIGS. 3a and 3b show the central processing unit 302 of FIG. 2 in greater detail as comprising a microprocessor 800 operating at a clock frequency of the order of 2 MHz, which is determined by the values of capacitors C11 and C12 and crystal XTAL.

The microprocessor 800 is provided with first and second input ports identified as Port 0 and Port 1, Port 0 having input lines 802a through 802h and Port 1 having input lines 804a through 804h. Data bus lines 806a through 806h pick up the data bus group DB, said lines also being identified as lines DB0 through DB7. The memory control lines 808a through 808e make up the memory control line group RMC. Read/write control line 809 and phase control line 811 complete the input/output lines of the microprocessor 800.

The timing counter 320 is shown in FIG. 3a as comprising bistable flip-flops 860 and 862 and a multi-stage binary register whose clock input 320a causes the register to be incremented and whose output lines 320b through 320g are sampled by the input ports 802c through 802h of microprocessor 800. Input ports 802a and 802b receive the outputs of flip-flop 862 and 862.

The bistable flip-flops making up the data register group 810 comprises the bistable flip-flops which have been disclosed hereinabove in connection with detection circuits 334 of FIG. 6; 312 of FIG. 7; 314 of FIG. 8 and 316 of FIG. 9. These bistable flip-flops have been reproduced in FIG. 3 for clarity to indicate the manner in which the central processor samples these bistable flip-flops during operation of the high speed document handling apparatus.

The ports 804b through 804g are selectively coupled to associated ones of the bistable flip-flops making up data register array 810. To significantly increase the number of bistable flip-flops in the data register array 810 which can be sampled, microprocessor 800 is further coupled with input/output (I/O) devices 812, 832 wherein control over the I/O devices 812, 832 is exerted through the memory control lines RMC0 through RMC4, as well as the write line (WR) and the phase control line C. Data is transferred to the microprocessor 800 from I/O device 812 (and/or 832) and from microprocessor 800 to I/O device 812 (and/or 832) by the data bus lines 820a through 820h. Ports 4 and 5 of I/O device 812 respectively receive the binary states of selected ones of the bistable flip-flops in data register array 810, as well as the mode switches provided in the control panel 340 shown in FIG. 11, and the data lines and control lines coupled to the segmented display arrays of the display circuit 342 shown in FIG. 10. The I/O device 834 (FIG. 3b) further provides control signals to the feed, stacker and gate motors at port 20, as well as providing signals to the lamp and brake means.

A memory interface circuit 824 (FIG. 3b) provides address information to the random access memory (RAM) 826. and to the programmable read-only memory (PROM) 830. The data bus lines DB0 through DB7 from microprocessor 800 are simultaneously coupled to the data lines of the PROM 830 and the RAM 826. The address lines from the microprocessor 800 are connected to the memory interface circuit 824 to set up address codes at the address outputs A0 through A7 in the case of RAM memory 826; and A0 through A10 in the case of PROM memory 830. The I/O devices 832 and 834 provide an interface between microprocessor 800 and controls external to the central processor unit 302. For example, I/O device 834, under control of microprocessor 800 through the lines RMC0 through RMC4 DB0 through DB7, exerts control over the sensor lamp 85, brake means 308, stacker motor Ms, feed motor Mf and gate motor Mg. I/O device 832 accepts input information from the control panel, as does I/O device 812; the post gate sensors 260 and 262; and provides clear signals to selected ones of the bistable flip-flops forming part of the data register array 810, as does I/O device 812. I/O device 812 also periodically samples selected ones of the bistable flip-flops forming part of data register array 810, under control of the microprocessor 800 and transfers the sampled data to RAM 826.

The operation of the control processing unit (CPU) 302 (in simplified terms) is as follows:

Operating power switch 766 (FIG. 11) to the ON position causes CPU 302 to enter into a "housekeeping" routine in which registers and the like are cleared in readiness for document handling and counting operations. The start button 762 is depressed, causing CPU 302 to enable the feed, gate and stacker motors Mf, Mg and Ms for later energization. CPU 302 advances to the next program step for examining the state of sensor 25b (FIG. 2) for the presence of sheets in the infeed hopper. In the event that no sheets are present, CPU 302 remains at this program step and continues to look for the presence of sheets. As soon as sheets are placed in the hopper, CPU 302 detects this condition and is advanced to the next program step at which time halogen lamp 85 (FIG. 2) is turned on and motors Mf, Mg, Ms are turned on to initiate document handling and counting operations.

The tests to be performed are selected by appropriate operation of the mode switches 744 through 750 (FIG. 11), causing the CPU 302 to sample those tests which have been selected. CPU 302 constantly monitors each sheet during the time in which a sheet moves between the sensor array and the output stacker. As was previously described, when the feed motor Mf is energized, timing gear 118 (FIG. 2) modulates light from source 114 directed towards sensor 120. The modulated light is converted into electrical pulses by sensor 120, which pulses are applied to clock input 860a of bistable flip-flop 860 (FIG. 3). The Q output 860b of flip-flop 860 is coupled to input 802a of microprocessor 800 through inverter 864 and is simultaneously coupled to clock input 862a of flip-flop 862. The Q output of 862b of flip-flop 862 is coupled to the clock input 320a of counter 320 and to input 802b of microprocessor 800 through inverter 866.

Timing pulses are developed at a rate which is a direct function of the rotating speed of timing gear 118 which in turn is controlled by the rotating speed (rpm) of the shaft 112 of feed motor Mf so that the apparatus is directly sensitive to changes in operating speed, which may be caused by either rapid or gradual changes in the local power source, aging of components, and the like.

CPU 302 looks for the presence of a document detect signal from document detect line 312b of the hole detection 312 (FIGS. 2 and 7). The occurrence of this signal causes microprocessor 800 to read the count of counter 320 into a predetermined register in microprocessor 800, (FIG. 3b). Microprocessor 800 is typically provided with a substantial number of such registers, which are comprised of predetermined memory locations within a small capacity memory provided in microprocessor 800, and identified by a six-bit address which may be represented by two octal bits.

Counter 320 starts at a zero count, counts up to a maximum count and, at the next pulse supplied to its clock input 320a, resets to zero and starts a new count. This operation continues in a regular, periodic fashion. In the preferred embodiment, considering FIG. 12, at a machine speed which moves sheets at a linear speed of the order of 100 ips, sheets approaching sensor array 86a–86d move past the array in 35 milliseconds, as shown by waveform 900. Thus the leading edge of the first sheet passes the sensing array to generate the leading edge "1" of waveform 900. The trailing edge of the first sheet passes the same point 35 milliseconds later to develop the trailing edge "2" of waveform 900. The next sheet follows the first-mentioned sheet, and is identified in waveform 900 as having leading and trailing edges "3" and "4" respectively. The gap between trailing edge "2" and leading edge "3" is utilized for counting purposes.

CPU 302 begins tracking each sheet when a document detect signal is generated indicating that the leading edge of a sheet is passing sensor array 86a–86d. CPU 302 looks for a document detect signal and, upon receipt of same, transfers the count in counter 320 through CPU 302 to a first predetermined register location in microprocessor 800. The offset count stored consists of an eight-bit count comprised of six bits from counter 320 plus two bits supplied from the outputs of flip-flops 860 and 862 to inputs 802a and 802b, respectively. Simultaneously therewith, CPU 302 sets an initial "status" count into a second predetermined register location in microprocessor 800, which location is associated with said first predetermined register location in microprocessor 800. The tracking of sheets is continued throughout the movement of a sheet by comparing the offset count stored in said first predetermined memory location in microprocessor 800 against the count developed by the accumulating timing pulses in counter 320.

The length of the document path throughout the document handling and counting apparatus is a known quantity and is based upon the geometry of the apparatus. The speed of each sheet is determined by the speed of feed motor Mf. Thus, it takes a predetermined number of pulses to move each sheet a predetermined distance.

The offset count set into the first predetermined register location in microprocessor 800 is unique to the sheet which it identifies. The eight-bit counter is designed to count to full capacity almost two times during the time it takes a sheet to move from the sensor array to the output stacker, whereby each sheet has a unique count number.

The second number stored in memory in microprocessor 800, identified as the status count, is initially set at zero. The status count in the second predetermined memory location in microprocessor 800 is incremented after the accumulation of a predetermined number of timing pulses. The count pulses occur at intervals within the range from 300 to 500 microseconds, depending upon the rpm of motor Mf. In one example, assuming timing pulses occur at intervals at the order of 333 microseconds, 105 timing pulses will be generated during the time that it takes a single sheet of paper currency to pass the sensor array. This data is utilized in order to track the sheet through the document handling apparatus 10.

As was mentioned hereinabove, the count in counter 320 is transferred into the status register, which is the aforementioned first predetermined memory location in microprocessor 800 as soon as the sheet of paper currency comes "on line." The offset count in the first predetermined location in microprocessor 800 is not changed throughout the movement of the sheet of paper currency through the document handling and counting apparatus 10. Simultaneously therewith, the second memory location associated with the first memory location and identified as the status register, stores a four-bit word which in hexadecimal notation represents the location of the sheet associated therewith as it travels through the sheet handling apparatus 10.

Depending upon the functions being performed by CPU 302, CPU 302 may examine counter 320 as frequently as twice during the same count and as infrequently as only once every two counts. Each time CPU 302 examines counter 320, the contents of the offset register is subtracted from the count in the counter 320 by a two's complement addition operation. The result of the two's complement addition, which in effect is a subtraction operation, provides information which aids in tracking the location of the leading edge of a sheet as it moves through the apparatus. Immediately upon coming "on line", the CPU sets a hexadecimal "03" into the second predetermined memory location in microprocessor 800 which is referred to as the status register. CPU 302 periodically examines the count in the status register and being apprised that this count is hexadecimal "03", knows that the count "03" places the sheet as still within the optics region of the document handling and counting apparatus 10, as a result of which CPU 302 examines the contents of the hole detection bistable flip-flop 810a, 810b, 810c and 810d, and the leading edge fold conditions stored in bistable flip-flops 810o and 810p. This information is transferred into microprocessor 800 through the I/O devices 812 and the input Port group number "1" of microprocessor 800. In the event that any of these conditions are present, a flag bit is inserted into a predetermined bit position provided in the status register to indicate that the document is unfit, i.e. has failed one or more of the tests being performed on the sheet.

As was mentioned hereinabove, the microprocessor 800 periodically samples the contents of counter 320 to determine the difference between the status count for a sheet in process and the count presently in the counter 320. When the difference between the contents of counter 320 and the count in the offset register for the first sheet accepted into the document handling and counting apparatus 10 is a count of 36, this indicates that the leading edge of said sheet has now entered into the limpness detection assembly 142. As a result, CPU 302 alters the hexadecimal word in the status register for said first sheet, to a hexadecimal "06". The CPU 302 then examines the contents of the status register and, finding that the value is "06", examines the contents of the limpness bistable 810q in array 810, to determine if the sheet has failed to meet the desired limpness criteria.

When the difference between the count in counter 320 and the count in the offset register associated with the first sheet indicates a value of the order of 120, this indicates that the first-mentioned sheet has now departed from the optical portion of the document handling and counting apparatus 10, i.e. its trailing edge has passed sensor array 86a–86d. This count causes the CPU 302 to alter the hexadecimal count in the status register associated with the first-mentioned sheet to a hexadecimal count "09". As a result, CPU 302 looks at the registers in data register array 810 which relates to optical examination of the sheet to complete the evaluation. Thus the contents of bistable flip-flops 810f, 810g, 810h, 810j, 810k, 810m and 810n are examined. In the event that the first-said sheet has failed to meet one or more of the established criteria, the bit position in the status register for indicating the status of the sheet being examined will be altered to indicate an unfit sheet, if it has not already been operated to do so.

CPU 302 continues to compare the contents of counter 320 against the offset count associated with the first sheet and when the difference between the contents of the offset register for the first-mentioned sheet and the count in counter 320 equals a count of 141, the contents of the status register associated with the first sheet is converted to hexadecimal "0C", indicating that the first-mentioned sheet has passed through the limpness apparatus 142 and is moving toward the gating roller 250 (FIG. 1). At this time, the contents of the first and second predetermined locations in microprocessor 800 are transferred to second and third predetermined memory locations in microprocessor 800 and, as soon as the leading edge of the next sheet is detected by sensor array 86a–86d, the count in counter 320 is stored in the first-mentioned memory location and the status register (i.e. the second predetermined location in microprocessor 800 is arbitrarily forced to the hexadecimal count "03".

The counterfeit detection apparatus which, when employed, is positioned between the limpness detector apparatus 142 and the sensor array 86, is also examined during the time that the hexadecimal code "09" is stored in the status register associated with the first-mentioned sheet.

The operations performed during the passage of the first-mentioned sheet through the system optics are substantially identically repeated for the second sheet and are also repeated for a third sheet, the geometry of the document handling and counting apparatus 10 being such that up to five sheets can be passing through apparatus 10 at any given time but, obviously, in different locations.

The first-mentioned sheet reaches the gating roller 250 (FIG. 1) after the counter 320 is stepped through a full count plus fourteen counts toward a second full count, for a total of 269 counts. At this time, CPU 302 subtracts the value in the offset register for the first-mentioned sheet from the contents of the counter 320 and, at a count of 269, causes the count in the status register to be converted to a hexadecimal "0F". Any time thereafter which CPU 302 examines the contents of the status register, the postgate sensors 260 and 262 are examined to ascertain whether a sheet has passed by said postgate sensors 260 or 262 to be assured that the sheet has been diverted to the proper output stacker.

The fit/unfit status is available at the time that the trailing edge of the first sheet has passed the limpness detector apparatus 142 (FIG. 1). The apparatus 10 has approximately 40 milliseconds to operate the gating roller motor Mg to rotate the gating roller 250 in the proper direction and at the desired speed (rpm). Since the gating motor Mg is capable of switching from the maximum rpm in a first direction to maximum rpm in the reverse direction within an interval of significantly less than 40 milliseconds, the switching of the gating roller 250 presents no timing problem.

As the leading edge of a third sheet passes the sensor array 86a–86d, the contents of counter 320 are inserted into the first predetermined memory location in microprocessor 800 and its associated status register is altered to present a hexadecimal count of "03". The contents of the third and fourth predetermined memory locations in microprocessor 800 constituting the second pair of status and offset registers are respectively shifted to fifth and sixth predetermined memory locations in microprocessor 800 while the contents of the first and second memory locations are shifted to said third and fourth predetermined memory locations just prior to the third sheet coming on line. Thus, CPU 302 continuously examines and updates three pairs of status and offset registers for three sheets associated therewith and occupying different positions within the document handling and counting apparatus 10.

A visually observable count of the sheets being examined are presented at the control panel 340 shown in FIG. 11. The apparatus 10 offers the feature of processing sheets in batches. For example, it may be desired to batch fit sheets in groups of 100. As a result, the document handling and counting apparatus 10 will temporarily stop operation when the output stacker 216 for fit sheets contains a number of sheets equal to the batch amount. The desired batch amount is set into CPU 302 by operating thumb wheel switches 736a through 736c until the decimal number representing the desired batch count is displayed by the number wheels of 736a-1, 736b-1 and 736c-1 associated with the thumb wheel switches 736a through 736c respectively. When the desired batch number is selected, "set" push button 738 is depressed and is entered into CPU 302 which then examines the count of the number of sheets stacked and compares it with the set batch number to temporarily halt document handling and counting apparatus 10 as soon as the desired batch quantity is delivered to the output stacker 216 containing fit sheets.

It is also possible to batch unfit sheets, which is accomplished in a similar manner by operating thumb wheel switch assembly 736 and depressing set button 740 to set the number of rejected or unfit sheets which constitutes a batch. In a similar fashion, CPU 302 examines the unfit batch number comparing it with the count of unfit sheets delivered to the output stacker receiving unfit sheets and temporarily halting operation when the unfit batch quantity is reached.

Display 720 displays the number of fit sheets while display 722 displays the number of unfit sheets. A separate count of the total number of sheets fed into the system optics is presented at display 724.

Each batch count resets automatically when the batch amount is reached and the batch count is transferred to the grand total, whereby display unit 726 is utilized to present a count representative of the grand total of sheets accepted, sheets rejected and total number of sheets inputted into the equipment.

The displays are operated in a multiplex fashion by CPU 302 which presents the data to be displayed on data lines, Data $2^0$ through Data $2^5$ and applies this data to the data input lines ID0 through ID7 of the interface circuits 770, 772 and 774 as shown in FIG. 10. The particular interface device selected is controlled by the decoder 778 which receives the data on the Add $2^0$ and Add $2^1$ lines and selects one of the interface devices 772 or 774 for operation. Each interface device converts the input information into a digit selection signal appearing at output lines D0 through D7, and a group of segment selection signals a through g. These segment selection signals, in the case of interface 770, are simultaneously applied to all six segmented display positions 720a through 720c and 722a through 722c, the particular display being illuminated at any given time being determined by the digit selection signal applied thereto. Interfaces 772 and 774 operate in a similar manner. The binary codes representing the decimal digits to be displayed are applied to the interfaces in a repetitive fashion. The displayed digits are applied at a rapid enough refresh rate to give the observer the impression that the segmented display devices are on constantly, when in fact they are being operated in a multiplexed fashion.

As was noted hereinabove, the data registers in data register array 810 are cleared after they are sampled in readiness for receipt of subsequent condition or status data, the sampling speed of the CPU being more than adequate to clear said registers well in readiness for their receipt of such data due to examination of the next sheet.

FIGS. 13-29 are flow diagrams which indicate the operations performed by microprocessor 800.

Figure 13:
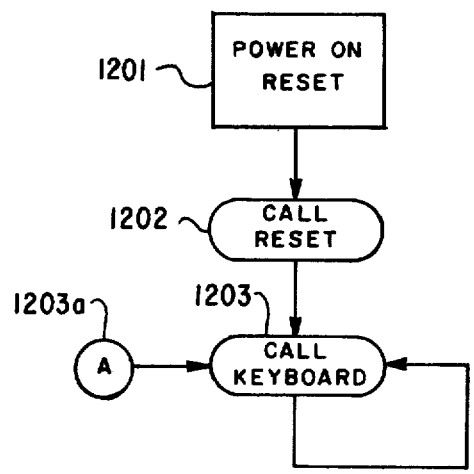

In FIG. 13 the power button 766 (FIG. 11) is turned on (1201), resetting the registers, clearing RAM 826, etc. (1202). Upon completion of the reset routine, the keyboard routine is selected (1203).

Figure 14:
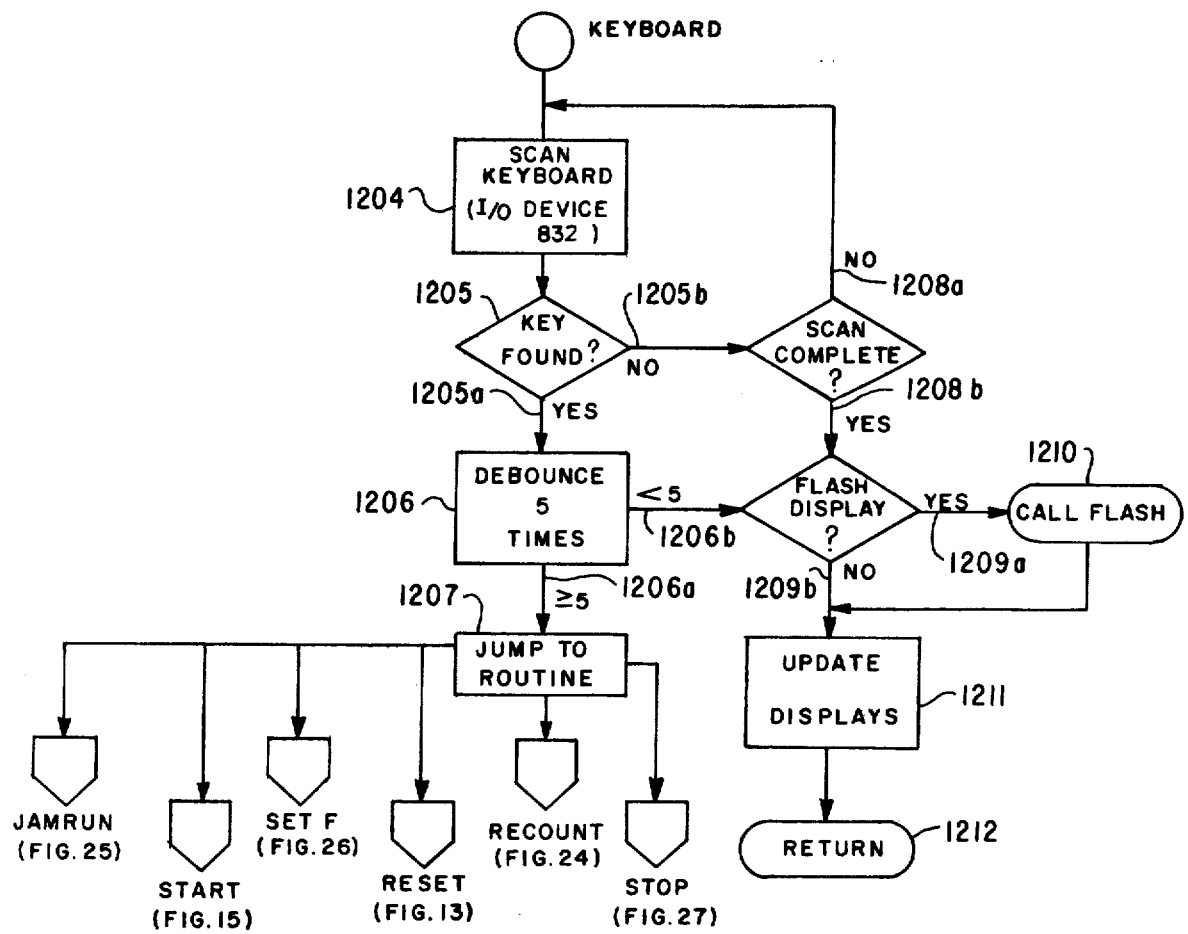

FIG. 14 shows the keyboard routine in which I/O device 832 is scanned (1204). If an operated key (see buttons on keyboard, FIG. 11) is found (1205a), it is examined five successive times (1206). If the key is still closed after the fifth time, the program jumps to the routine associated with the operated key (1207).

If no operated key is found (1205b) and the scan is not complete (1208a), the keyboard I/O 832 is scanned again.

If the scan is complete (1208b), the display is flashed (1209a). If the debounce reading indicates that the closed switch remained closed for less than five successive scans (1206b), the display is flashed by calling the flash routine (1210). If the display is not to be flashed (1209b), the displays are updated (1211) and the program returns to the point which it occupied prior to performing the flash routine.

Figure 15:
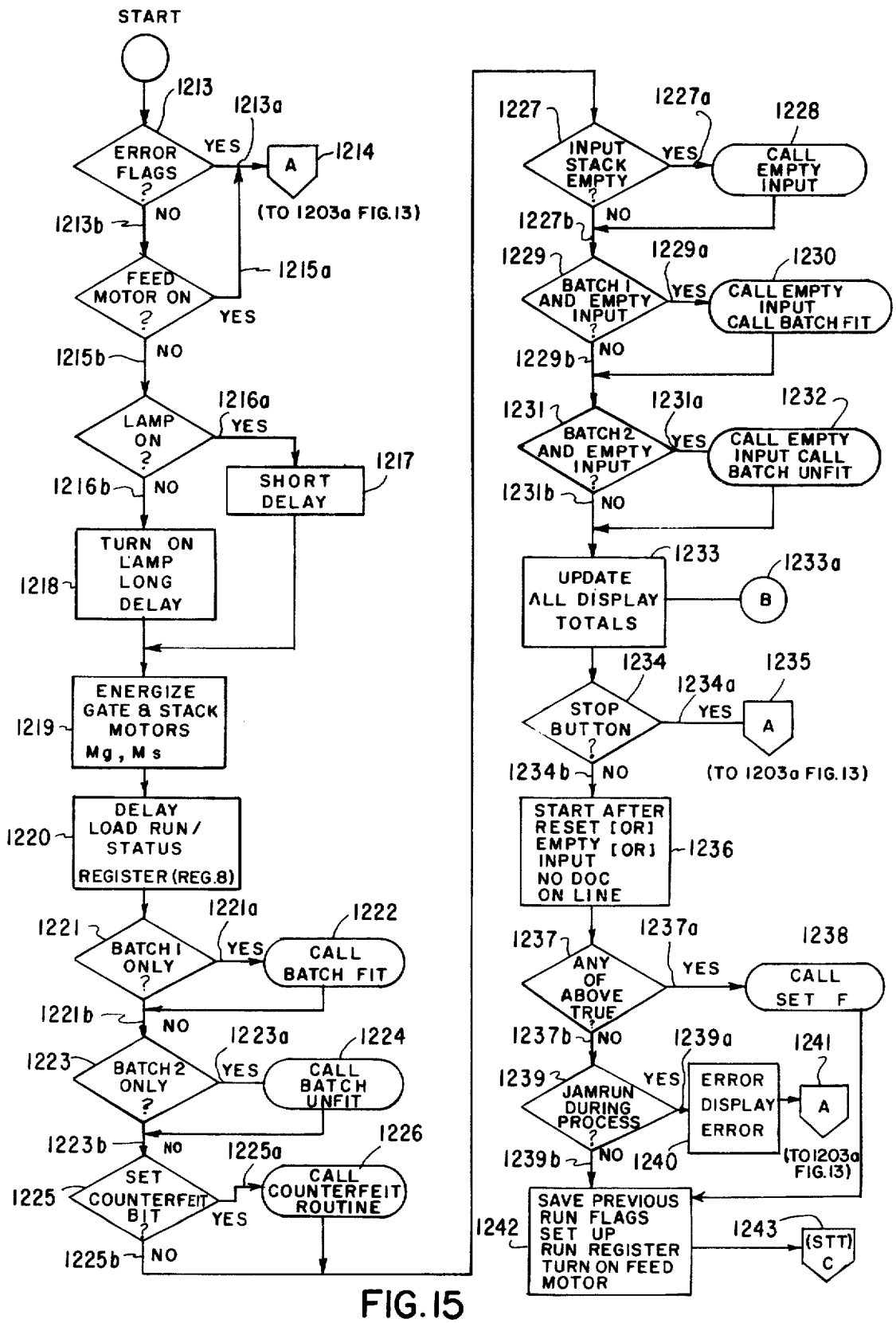

The start routine is shown in FIG. 15. The presence of an error flag (1213a) causes a return (1214) to the keyboard routine (1203) through (1203a, FIG. 13). If there are no error flags (1213b) and the feed motor is on (1215a) the program returns to the keyboard routine (1203). If the feed motor is off (1215b) and the lamp is on, after a short delay (1217) the gate ($M_g$) and stack ($M_s$) motors are turned on (1219). If the lamp is off (1216b) it is turned on and after a longer delay (1218) the motors are turned on (1219). The loading of the run/status registers is delayed (1220) until the status of the machine 10 is examined to determine why the machine stopped. If a batch is contained in the fit stacker ("Batch 1"-1221a), the batch fit routine is called (1222) to load the proper bit in memory. If there is no fit batch (1221b) and the batch is unfit ("Batch 2"-1223a), the unfit batch routine is selected (1224). If there is no unfit batch (1223b), the counterfeit bit is examined (1225). If it is set (1225a), the counterfeit routine is called (1226). If the counterfeit bit is not set (1225b), the input stack is examined. If empty (1227a), the empty input program is called (1228) typically to provide an indication to the operator. If not empty (1227b), the fit batch and input are both examined (1229) and thereafter the unfit batch and input are examined (1231) to determine if the routines (1230) or (1232) should be selected, after which all display totals are updated (1233).

If the stop button has been depressed (1234a), the keyboard scan routine is called (1235). If not, the conditions of (1236) are examined. If none are true (1237b) and a jam runout is in process (1239a), an error condition is displayed and the program returns to the keyboard scan routine (1241). If no jam run is in process, previous run flags are retained, the run register is set up and the feed motor $M_f$ is turned on (1242) and the routine of FIG. 16 is called.

Figure 17:
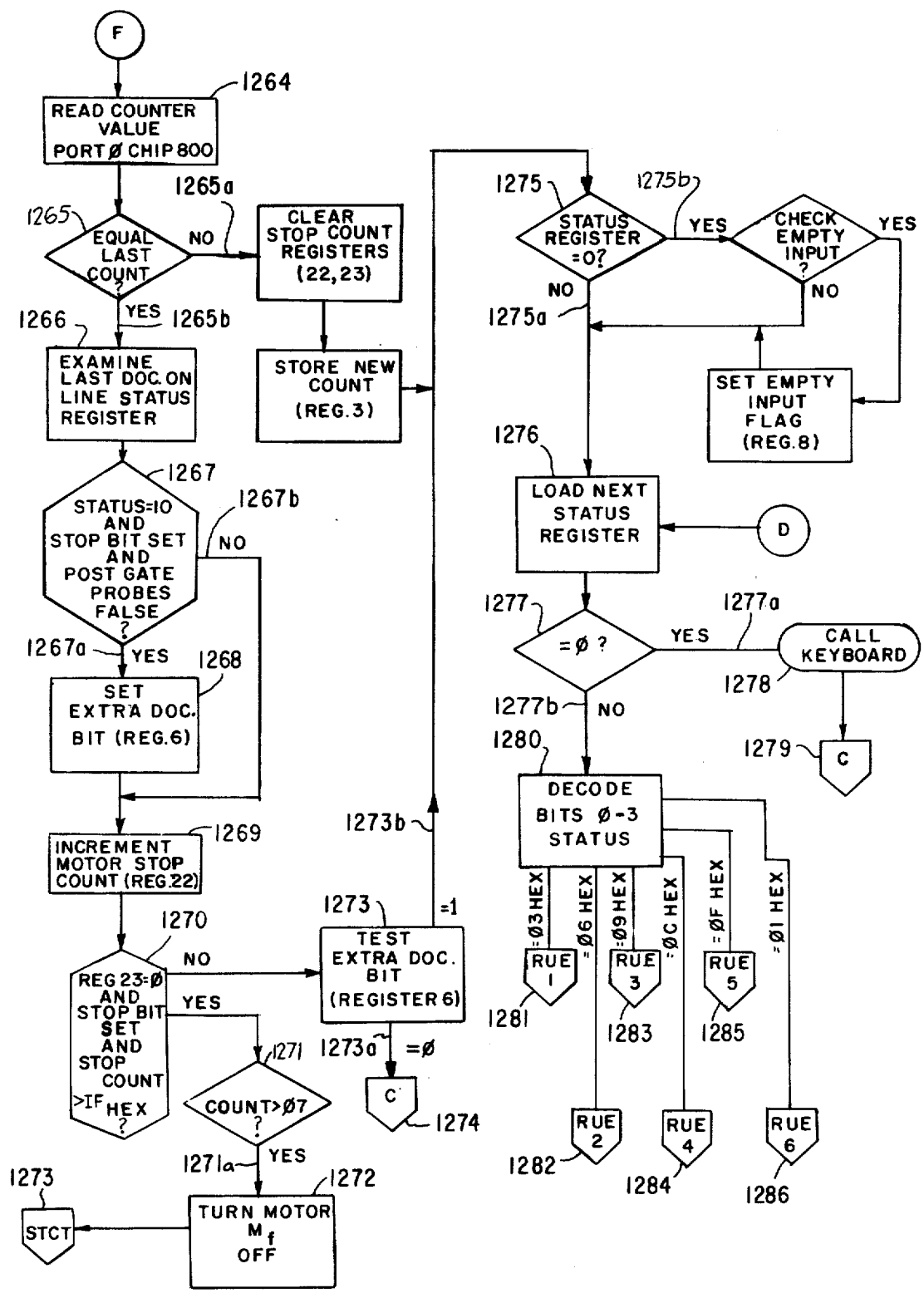

If any of the conditions examined at (1236) are true (1237a), the routine of FIG. 17 is called which reads the switches and loads the values read in the proper registers. The program then proceeds to (1242) et seq.

Figure 16:
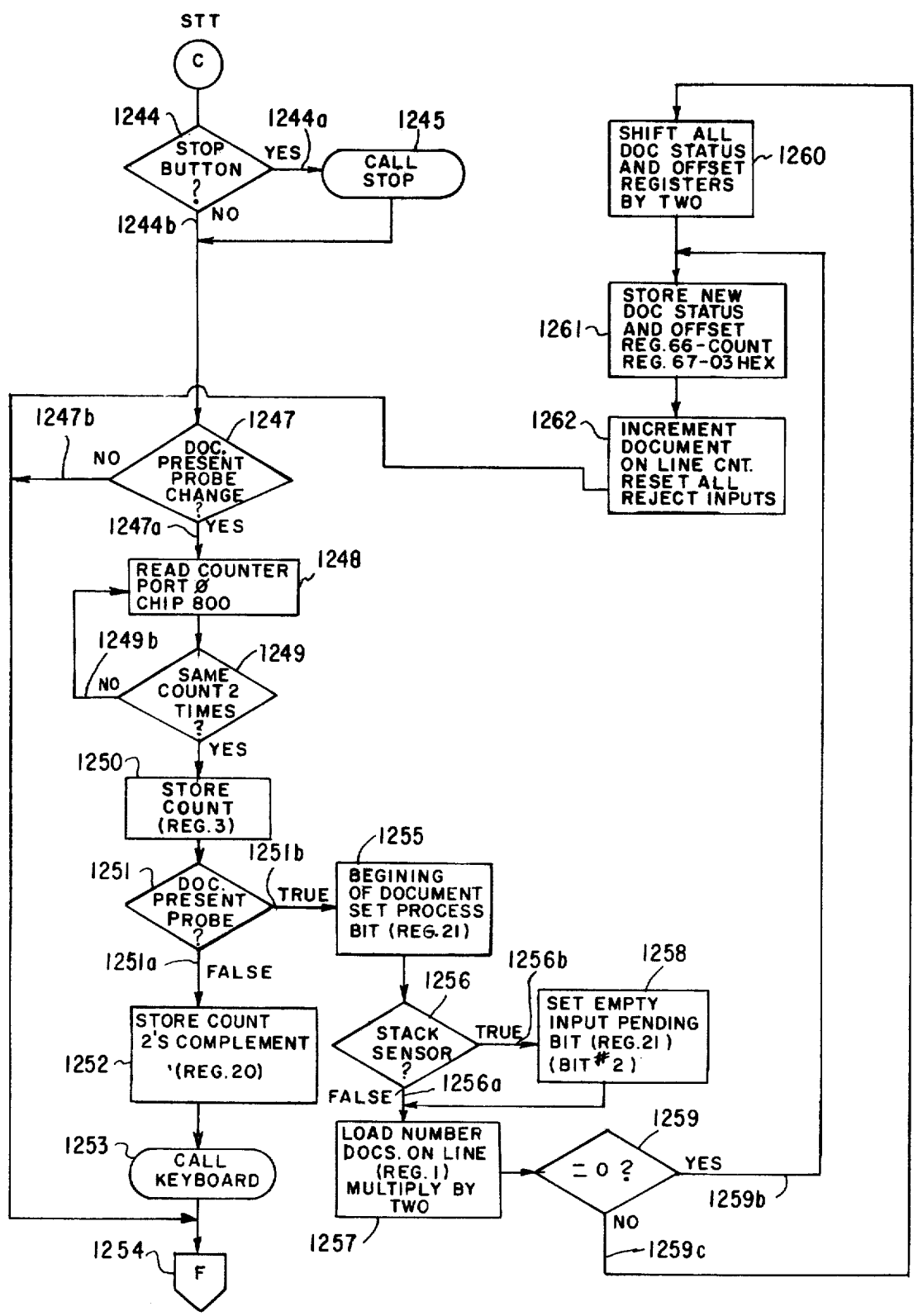

The routine FIG. 16 is employed when running sheets through apparatus 10. If the stop button is on (1244a), the stop routine (1245) is performed and the program then moves to step (1247). If the stop button is off (1244b) the sheet present probe is examined to assure operation of the feed motor (1247). If a change occurs (1247a), the count in counter 320 is read into microprocessor two times (1249). If the count is the same both times, indicating that both readings were not taken on opposite sides of a transition, the count is stored in microprocessor register $3_{Hex}$ (1250). This is the offset count. If a sheet is detected by sensor 97 (FIG. 2), the "in process" bit in register 21 is set (1255). If no sheets are in the infeed, as determined by stack sensor 25b (FIG. 2), the empty input bit in Register 21 is set (1258) and the count of the number of documents on line in apparatus 10 is doubled (1257). If the count is not zero (1259c), all of the status and offset registers in microprocessor 800 are each shifted twice (1260) the number of shifts being determined by the number of sheets already on line. The new document status and offset counts are respectively stored in microprocessor registers $66_{Hex}$ and $67_{Hex}$ (1261). The on-line count in register No. 1 is incremented and all reject inputs are reset (1262). The program then proceeds to the routine of FIG. 17.

If the sheet present probe indicates no sheet present (1251a), the count of counter 320 (FIG. 3a) representing the count when the trailing edge of the sheet has passed the system optics 86, is stored in two-s complement form (1252), the keyboard is called and the program jumps to the routine of FIG. 17 (1254).

As shown in FIG. 17, the value of counter 320 is loaded in port O of microprocessor 800 (1264) if equal to the last count (1265b) indicating that the feed motor is not running, the on-line status register $1_{Hex}$ is examined to determine the number of sheets in process (1266). If the conditions of (1267) are met (i.e. 1267a), the extra document bit is set (1268) and the motor stop count is incremented (1269). When the count in register 23 is zero the stop bit is set and the stop count is greater than $1F_{Hex}$ the motor $M_f$ is reversed (1270). When a count of $07_{Hex}$ is reached, indicating that the motor has just about stopped but has not reversed, power to the motor $M_f$ is turned off (1272), and the program jumps to the Stop-Continue routine of FIG. 29 (1273).

If the conditions of (1270) are not met, the extra document bit is examined. If zero (1273a) the routine returns to the start continue routine of FIG. 16 (1274).

If the extra document bit is set (1273b), the status register is not 0 (1275a), the next status register is loaded (1276). If zero (1277a) the keyboard routine is called (1278) and then the program returns to the start-continue routine of FIG. 16 (1278).

If not zero (1277b), bits 0 through 3 are decoded to determine what RUE (routine) (1281–1286) is selected.

Figures 18, 19:
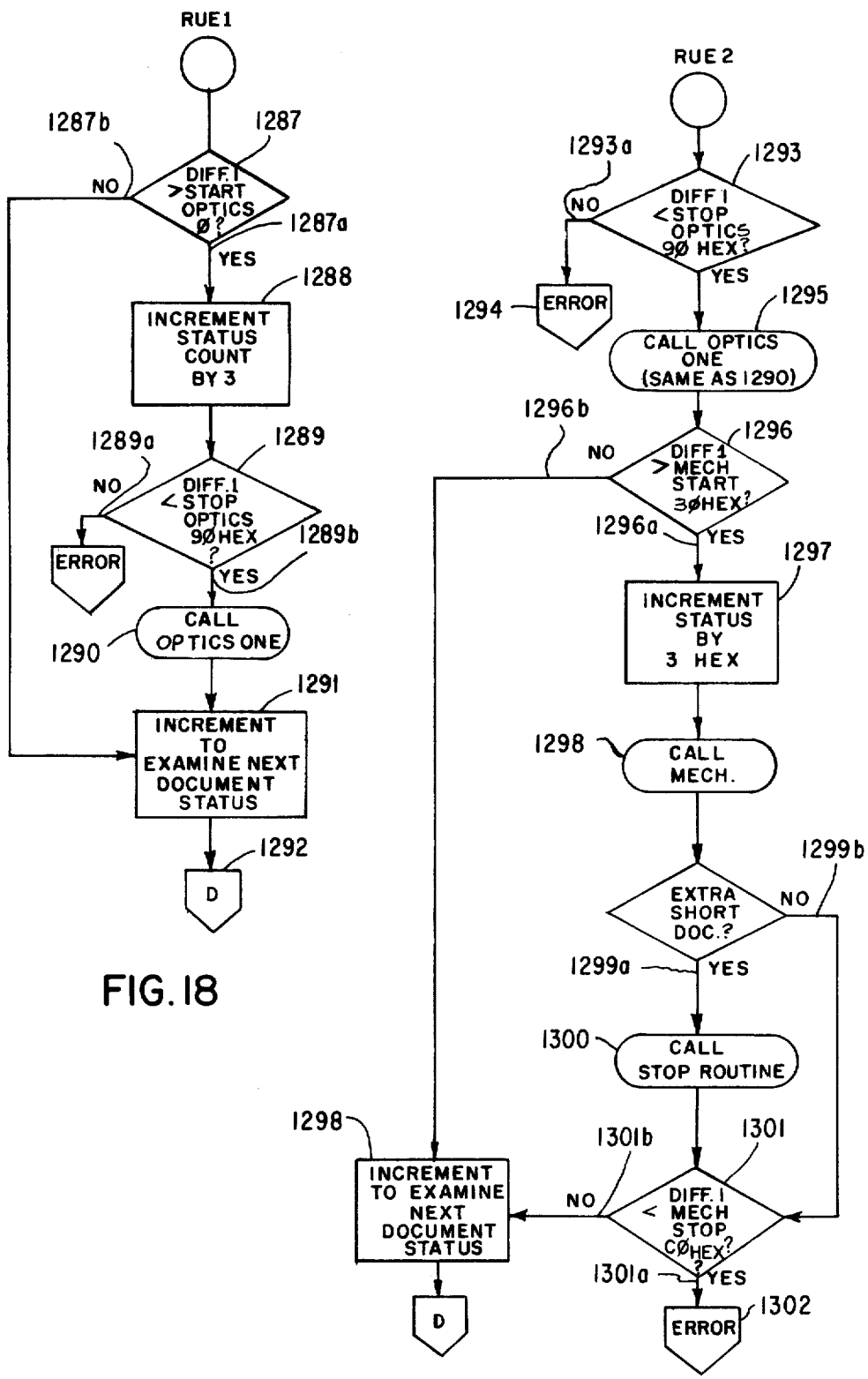

In RUE 1 shown in FIG. 18, the optics tests are examined. If the difference between the present count in counter 320 and the offset count is greater than the start optics (1287a) the associated status count is incremented by $3_{Hex}$ (1288). If not (1287b), the status register of the next document is examined (1291) and the program returns to (1276) of FIG. 17 (1292).

Once the status counter is incremented (1288), if the difference is greater than $90_{Hex}$ (the stop optics count) an error signal is created (1289a) since the microprocessor 800 has allowed too much time to elapse before examining this register. If less than $90_{Hex}$ (1289b), the optics tests are examined and the results are stored in the appropriate registers in array 810 (FIG. 3a). The routine then advances to (1291) described above and then returns to (1276) of FIG. 17 (1292).

In RUE 2 of FIG. 19, the results of the mechanics (limpness) tests are examined. If DIFF $1 > 90_{Hex}$, (1293a) an error signal is developed for the same reason as set forth above in connection with (1289a). If not, the optics test results are again examined (1295). If DIFF $1 > 30_{Hex}$, i.e. start of mechanics (1296a), the sheet has passed the mechanics and the status register is increased by $3_{Hex}$ (1297). If not (1296b), status register for the next sheet is called (1298) and program returns to (1276) of FIG. 17. The results of the limpness test are then stored (1298). If the sheet is $< \frac{1}{3}$ the length of a normal sheet (1299a) the stop routine is called. If $>$ than $\frac{1}{3}$ of normal length, the sheet can be processed in the normal manner (1299b) and, if the difference is now less than mechanical stop (i.e. end of mechanics) (1301a), an error is indicated (1302). If less than $CO_{Hex}$ (1301b), the next status register is called and program returns to (1276) of FIG. 17.

Figures 20, 21:
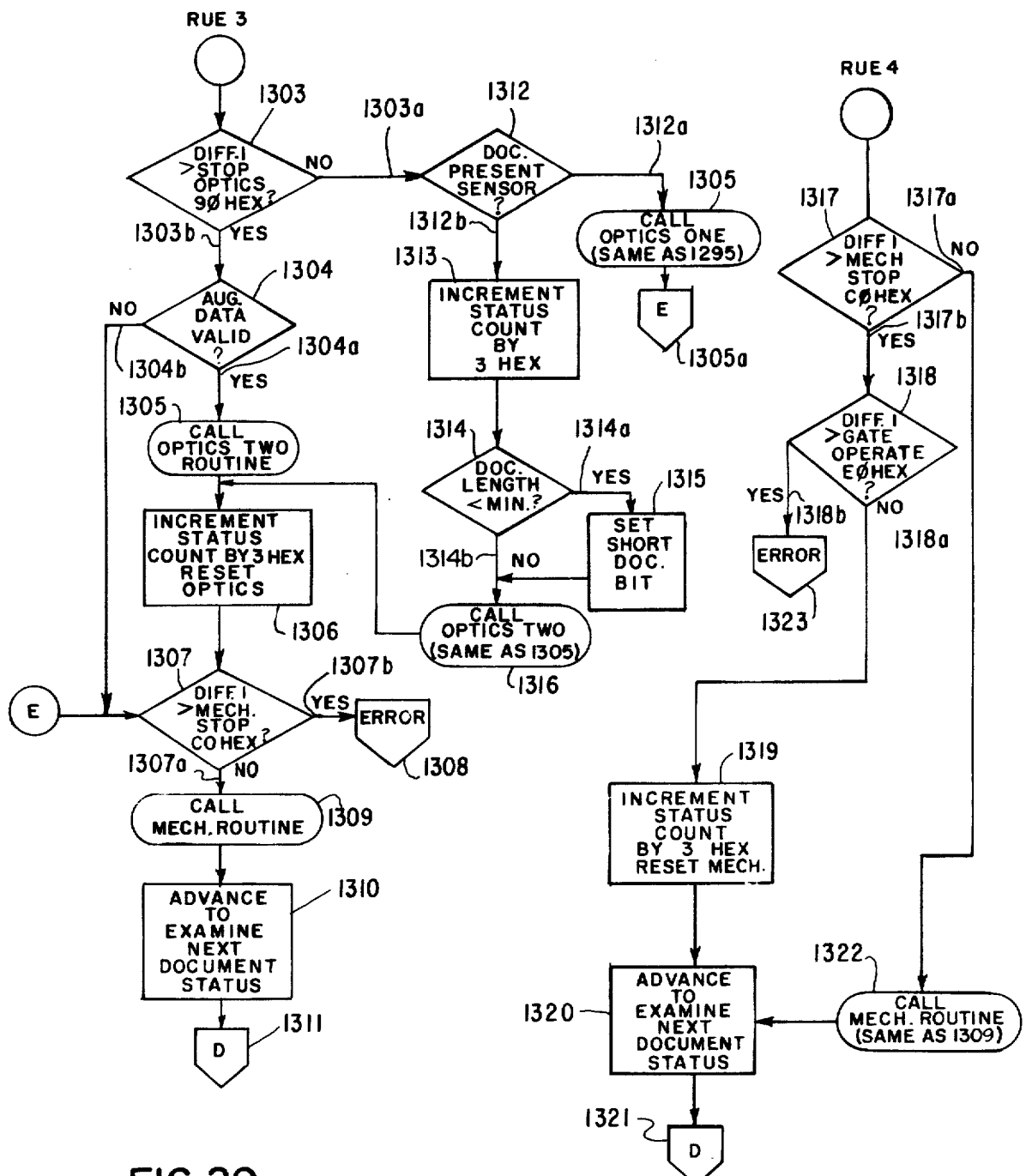
Figure 24:
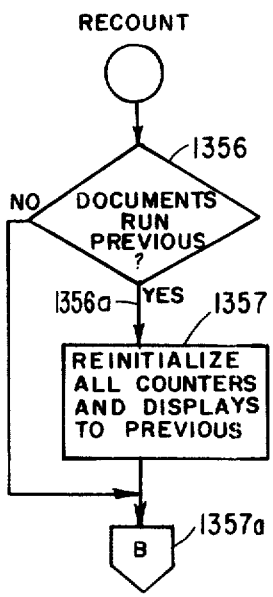

RUE 3 of FIG. 20 examines the results of the average density and length tests. If DIFF $1 > 90_{Hex}$ (1303b) and the average data is valid (1304a) per register 684 of FIG. 9, the results are stored in RAM memory 826 (1305) and the status count is increased by $3_{Hex}$ (1306). If DIFF $1 > CO_{HEX}$ (1307b) i.e. microprocessor 800 took too long to reach this step, an error is indicated (1308). If not (1307a), the mechanics routine is called (1309), the next status register is called (1310) and the program returns to (1276), FIG. 17 (1311).

If the average data is not valid, the program jumps from (1304b) to (1307) and continues as described.

If DIFF 1 is not greater than $90_{Hex}$ (1303a), the sheet present sensor looks for a sheet (1312). If a sheet is present (1312a) the optics routine (1305') and then jumps to (1305a'). If no sheet is present (1312b) the status count is increased by $3_{Hex}$ (1313), and sheet length is examined (1314). If the sheet $< \frac{1}{3}$ normal length (1314a) the short bit is set (1315). If not (1314b), the optics two routine (1316) is called and routine then proceeds to (1306).

In RUE 4 in FIG. 21, if DIFF $> CO_{Hex}$ (1317b) and if DIFF $1 > EO_{Hex}$, the gate operate count, (1318a), the status count is increased by $3_{Hex}$ (1319), the next status register is called (1320) and the routine returns to (1276) of FIG. 17.

If DIFF $1 < CO_{Hex}$ the mechanical routine (1322) is called and then the program returns to 1320. If DIFF- $> EO_{Hex}$ (1318b) an error signal is created (1323).

RUE 5 of FIG. 22 is employed to operate the gating roller 250 of FIG. 1 to route the sheet approaching the gating roller 250 to the correct stacker, i.e. fit (216-FIG. 2) or unfit (218-FIG. 1).

RUE 6 of FIG. 23 is employed to: examine post gate sensors 260 and 262 of FIG. 1 (1334–1340); to set new values in their proper storage devices such as the counterfeit (CDA) bit (1343a and 1344), batch count (1345a and 1346), stack count, fit count, unfit count (1347); to clear status registers for processing new sheets (1351);

display results (1354); and return to the start continue routine (1244-FIG. 16).

The recount routine (FIG. 24) clears the appropriate displays (1357) if the sheets were run previously (1356a), and returns to 1233 of FIG. 15.

Figure 25:
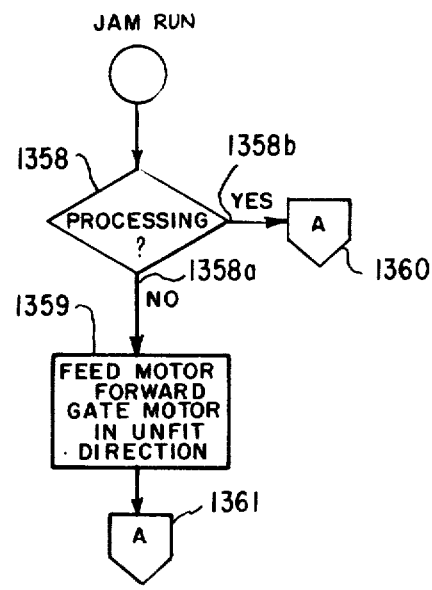

The Jam Run routine of FIG. 25 directs sheets being moved by the feed motor $M_f$ to the unfit stacker (218-FIG. 1) if not processing (1358a) and returns to the Call Keyboard routine (1203-FIG. 13). If processing (1358b) the program returns directly to the Call Keyboard routine (1360).

Figure 26:
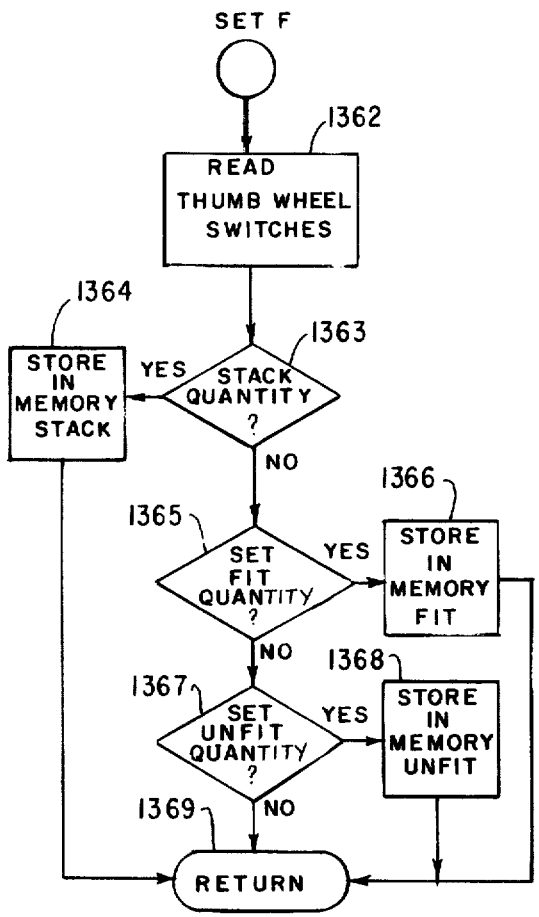

The Set F routine of FIG. 26 reads the thumbwheels (736-FIG. 11) and stores the settings in RAM memory 826 (FIG. 3b) for storing fit and unfit quantities and returns to the program location that it left when it was called to read the thumbwheel switches.

Figure 27:
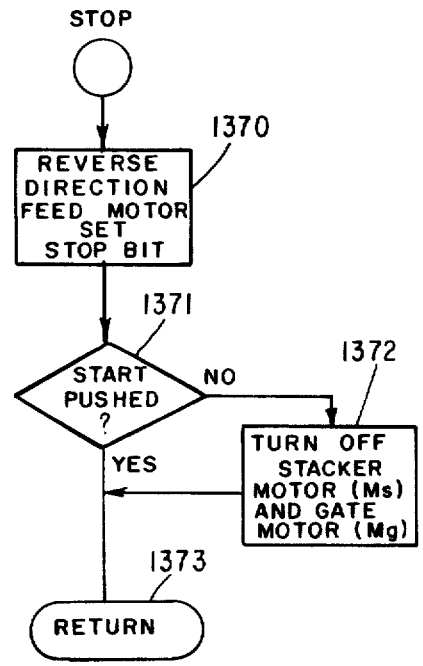

The Stop routine of FIG. 27 responds to a stop condition by turning off the motors $M_s$ and $M_g$ (1372) unless the start button was pushed (1371a) and returns to the program location it was at when the stop condition occurred.

Figure 28:
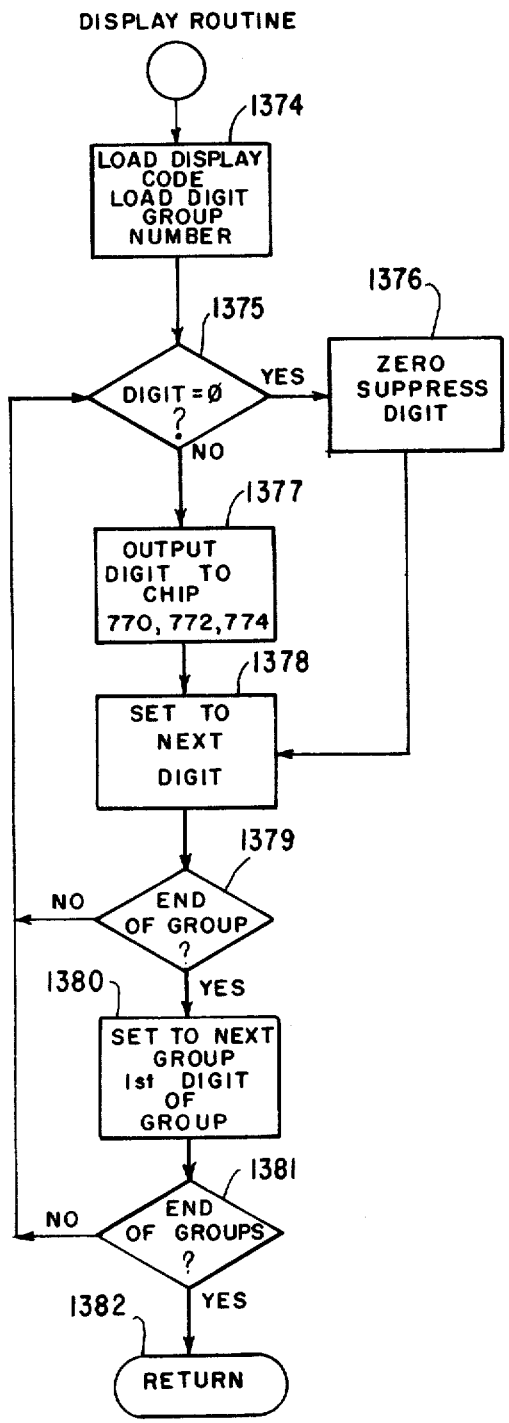

The Display Routine of FIG. 28 operates the displays in accordance with the data last stored. Each digit display position of each display 720–726 (FIG. 11) is handled one at a time (1374, 1375, 1377, 1378) until all display groups are examined (1381). A zero suppression is performed (1376) to reduce the number of LED's illuminated to only those which are necessary to correctly display the counts. The program then returns to the point from which it was called to execute the display routine.

Figure 29:
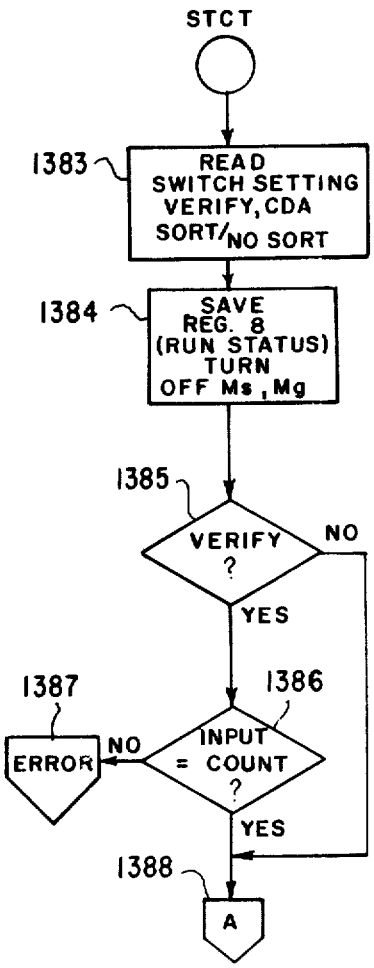

The Stop-Continue routine of FIG. 29 is utilized to perform the verify operation already explained above.

It can thus be seen from the foregoing description that the present invention describes a novel document handling and counting apparatus capable of performing a significant number of evaluations upon sheets as they move through the apparatus at high speed and further divert sheets to either a fit or an unfit output stacker in accordance with the criteria being examined. The apparatus has a novel batching capability in which it is possible to batch both fit and unfit sheets, at which time the equipment is temporarily halted to remove a completed fit (or unfit) batch, the sensory equipment being capable of indefinitely storing whatever conditions have been examined until restart of the equipment after removal of the completed batch. It is thus possible with the equipment of the present invention to evaluate and collate sheets into fit and unfit stacks at operating speeds commensurate with devices capable only of counting sheets at high speed.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. Microprocessor-based control means for operating document handling apparatus comprising means for moving sheets in a first direction at spaced intervals along a predetermined path;

sensing means for detecting the passage of sheets and for detecting predetermined characteristics of said sheets;

at least one of said sensing means being adapted to generate a signal upon the passage of the leading edge of each sheet at the location of said one sensing means;

means for generating timing pulses at a rate which is a function of the velocity of said sheets moving along said predetermined path;

multi-stage counter means being pulsed by said timing means;

memory storage means;

means responsive to a leading edge signal for transferring the contents of said multi-stage counter means to a predetermined location in said memory storage means;

said microprocessor-based control means further including means for periodically sampling the contents of said counter means and for determining the difference between the count stored in said predetermined location in said memory storage means and the count developed by said multi-stage counter means at the time said counter means is sampled wherein the difference in said count represents the location of said sheet along said predetermined path;

document condition examining means positioned at spaced intervals along said path;

means for temporarily storing examined conditions;

means responsive to predetermined difference values between the status count stored in said predetermined location in said memory storage means and the count sampled from said multi-stage counter means for examining the conditions in said temporary storing means.

2. The apparatus of claim 1 further comprising means adjacent to the output end of said predetermined path for diverting sheets meeting predetermined criteria toward a first outfeed stacking location and for diverting sheets failing to meet said predetermined criteria toward a second outfeed stacking location;

said microprocessor-based control means further comprising means responsive to a predetermined difference between said status count in said first predetermined location in said memory storage means and the count in said counter means for operating said diverting means in accordance with said evaluated data whereby operation of said diverting means is initiated sufficiently prior to the leading edge of the sheet in question arriving at said diverting means to be assured that said sheet is diverted to the proper outfeed location.

3. The apparatus of claim 2 wherein said microprocessor-based control means further comprises means responsive to a leading edge of a sheet passing said sensing means for shifting the status count in said first predetermined location to a second predetermined location in said memory storage means and for shifting the status count of the sheet whose leading edge is now passing said sensing means from said multistage counting means into said first predetermined location in said memory storage means;

said microprocessor-based control means including means for periodically determining the difference between the status counts stored in said first and second predetermined memory locations and the status count presently in said multi-stage counter means for determining the time at which the outputs of said sheet evaluation means should be transferred to said memory storage means.

4. A method for evaluating sheets to determine their fitness including plural sheet evaluating means arranged at predetermined spaced locations comprising the steps of;
moving sheets at spaced intervals in a first direction along a predetermined path which moves said sheets past said sheet evaluating means;
generating pulses at a rate representative of the velocity of the sheets moving in said predetermined direction;
counting said pulses;
automatically restarting said count when said count reaches a predetermined maximum value;
storing said count at a predetermined location in a memory when the leading edge of a sheet passes a predetermined location;
periodically comparing the present count being developed against the count stored in said predetermined location for determining the difference therebetween;
examining the results of one of said sheet evaluating means when said difference lies within a predetermined range;
examining the results of a second one of said sheet evaluating means when said count lies within a second predetermined range different from said first range.

5. The method of claim 4 comprising the steps of operating a diverting means when said difference lies within a third predetermined range, said range being selected to assure operation of said diverting means prior to the time that the leading edge of the sheet to be diverted reaches said diverting means to provide sufficient time to operate said diverting means.

6. The method of claim 5 further comprising the step of operating said diverting means to divert sheets toward a fit stacking location when the evaluation of the sheet indicates that it has met certain criteria and for diverting the sheet to an unfit output stacking location when the data evaluated indicates that the sheet has failed to meet the aforesaid criteria.

7. The method of claim 4 further comprising the steps of:
counting the number of fit sheets;
counting the number of unfit sheets, and displaying said counts.

8. The method of claim 4 further comprising the steps of:
counting the number of fit sheets;
counting the number of unfit sheets;
comparing the number of fit sheets against an adjustable setting; and
halting the movement of sheets when the number of fit sheets reaches said setting.

9. The method of claim 4 further comprising the steps of:
counting the number of fit sheets;
counting the number of unfit sheets;
comparing the number of unfit sheets against an adjustable setting; and
halting the movement of sheets when the number of unfit sheets reaches said setting.

10. The method of claim 4 further comprising detecting for the presence of genuine sheets;
diverting the sheet which is other than genuine to a location for receiving unfit sheets; and
halting the further feeding of sheets.

11. The method of claim 4 further comprising the steps of detecting the presence of sheets at the input end of said predetermined path to halt the apparatus in the absence of sheets at said input end.

12. A method for operating document handling, counting and evaluating apparatus comprising the steps of:
moving sheets at spaced intervals in a first direction along a predetermined path;
detecting the presence of the leading edge of the sheets as they pass a predetermined location;
generating pulses at a rate which is a function of the velocity of the sheets moving along said path;
counting said pulses;
beginning a new count each time the count reaches a predetermined maximum value;
storing, in a first predetermined memory location, the count present at the time a leading edge of a sheet passes a first predetermined location;
transferring the count stored in said first predetermined memory location to a second predetermined memory location when the leading edge of the next sheet passes said first predetermined location along said path and storing the count being developed at that time in said first predetermined memory location;
periodically determining the difference between the counts in said first and second predetermined memory locations and the aforesaid instantaneous count;
sampling the results of one of the evaluation means when said difference lies within a first predetermined range;
sampling the results of a second one of said evaluation devices when said difference lies within the second predetermined range different from said first predetermined range;
diverting said sheets to a first output stacking location when the sheet meets the evaluation criteria and diverting the sheet to a second output location when the sheet fails to meet the evaluation criteria.

* * * * *